United States Patent
Bendall

(10) Patent No.: US 10,019,812 B2
(45) Date of Patent: Jul. 10, 2018

(54) GRAPHIC OVERLAY FOR MEASURING DIMENSIONS OF FEATURES USING A VIDEO INSPECTION DEVICE

(71) Applicant: General Electric Company, Schenectady, NY (US)

(72) Inventor: Clark Alexander Bendall, Skaneateles, NY (US)

(*) Notice: Subject to any disclaimer, the term of this patent is extended or adjusted under 35 U.S.C. 154(b) by 0 days.

(21) Appl. No.: 15/648,010

(22) Filed: Jul. 12, 2017

(65) Prior Publication Data

US 2017/0337705 A1    Nov. 23, 2017

Related U.S. Application Data

(63) Continuation-in-part of application No. 15/018,628, filed on Feb. 8, 2016, which is a continuation-in-part (Continued)

(51) Int. Cl.
*G01R 33/12* (2006.01)
*G06T 7/62* (2017.01)
(Continued)

(52) U.S. Cl.
CPC ............ *G06T 7/62* (2017.01); *G01B 11/24* (2013.01); *G06F 3/04845* (2013.01); *G06T 7/0004* (2013.01)

(58) Field of Classification Search
CPC ............ G01R 31/2891; G01R 35/005; G01R 31/2887; G01R 1/06794; G01R 31/2808;
(Continued)

(56) References Cited

U.S. PATENT DOCUMENTS 4,375,320 A * 3/1983 Smirmaul ............ A61B 3/107
                                                        351/212
4,493,105 A    1/1985 Beall et al.
(Continued)

FOREIGN PATENT DOCUMENTS

CN    1158684 A    9/1997
EP    00549182 A2  6/1993
(Continued)

OTHER PUBLICATIONS

Unofficial English translation of Office Action issued in connection with related CN Application No. 201210063764.6 dated Sep. 2, 2015.
(Continued)

*Primary Examiner* — Jermele M Hollington
*Assistant Examiner* — Taqi Nasir
(74) *Attorney, Agent, or Firm* — Mintz Levin Cohn Ferris Glovsky and Popeo, P.C.

(57) ABSTRACT

A method and device for providing a graphic overlay for measuring dimensions of features using a video inspection device. One or more measurement cursors are placed on pixels of an image of the object. One or more planes are determined parallel or normal to a reference surface or line and passing through surface points associated with the measurement cursors. A semi-transparent graphic overlay is placed on pixels with associated surface points having three-dimensional surface coordinates less than a predetermined distance from the plane(s) to help the user place the measurement cursors.

20 Claims, 34 Drawing Sheets

Related U.S. Application Data of application No. 14/660,464, filed on Mar. 17, 2015, which is a continuation-in-part of application No. 14/108,976, filed on Dec. 17, 2013, now Pat. No. 9,875,574, and a continuation-in-part of application No. 13/040,678, filed on Mar. 4, 2011, now Pat. No. 9,013,469.

(60) Provisional application No. 62/232,866, filed on Sep. 25, 2015.

(51) Int. Cl.
    *G06T 7/00* (2017.01)
    *G06F 3/0484* (2013.01)
    *G01B 11/24* (2006.01)

(58) Field of Classification Search
    CPC ............ G01R 31/2851; G01R 31/3191; G06T 2207/10012; G06T 2207/10016; G06T 2207/30196; G06T 7/11; G06T 7/73; G06T 2207/30244
    USPC ............ 324/750.02, 750.13, 750.17, 750.23, 324/754.19, 237, 238, 239, 240, 456, 718; 382/108, 103, 199, 141, 119, 154, 106
    See application file for complete search history.

(56) References Cited

U.S. PATENT DOCUMENTS

| | | | |
|---|---|---|---|
| 4,980,763 A | 12/1990 | Lia | |
| 4,988,886 A | 1/1991 | Palum et al. | |
| 5,066,119 A | 11/1991 | Bertrand | |
| 5,175,601 A | 12/1992 | Fitts | |
| 5,302,999 A | 4/1994 | Oshida et al. | |
| 5,307,152 A | 4/1994 | Boehnlein et al. | |
| 5,434,669 A | 7/1995 | Tabata et al. | |
| 5,510,833 A | 4/1996 | Webb et al. | |
| 5,581,352 A | 12/1996 | Zeien | |
| 5,633,675 A | 5/1997 | Danna et al. | |
| 5,810,719 A | 9/1998 | Toida | |
| 5,822,066 A | 10/1998 | Jeong et al. | |
| 5,823,942 A | 10/1998 | Toida | |
| 6,011,624 A | 1/2000 | de Groot | |
| 6,064,759 A | 5/2000 | Buckley et al. | |
| 6,083,162 A | 7/2000 | Vining | |
| 6,201,541 B1 | 3/2001 | Shalom et al. | |
| 6,291,991 B1* | 9/2001 | Schnell | B65G 43/02 198/810.02 |
| 6,323,952 B1 | 11/2001 | Yomoto et al. | |
| 6,359,434 B1* | 3/2002 | Winslow | G01N 27/9046 324/220 |
| 6,438,272 B1 | 8/2002 | Huang et al. | |
| 6,459,481 B1 | 10/2002 | Schaack | |
| 6,670,962 B2 | 12/2003 | Perry et al. | |
| 6,717,578 B1 | 4/2004 | Deering | |
| 6,945,931 B2 | 9/2005 | Ogawa | |
| 6,956,576 B1 | 10/2005 | Deering et al. | |
| 6,990,228 B1* | 1/2006 | Wiles | G06T 17/10 345/419 |
| 7,030,996 B2 | 4/2006 | De Groot et al. | |
| 7,286,246 B2 | 10/2007 | Yoshida | |
| 7,372,558 B2 | 5/2008 | Kaufman et al. | |
| 7,388,679 B2 | 6/2008 | Yoshino et al. | |
| 7,453,456 B2 | 11/2008 | Petrov et al. | |
| 7,474,803 B2 | 1/2009 | Petrov et al. | |
| 7,486,805 B2 | 2/2009 | Krattiger | |
| 7,518,632 B2 | 4/2009 | Konomura | |
| 7,551,293 B2 | 6/2009 | Yelin et al. | |
| 7,564,626 B2 | 7/2009 | Bendall et al. | |
| 7,570,363 B2 | 8/2009 | Petrov et al. | |
| 7,570,370 B2 | 8/2009 | Steinbichler et al. | |
| 7,755,817 B2 | 7/2010 | Ho et al. | |
| 7,782,453 B2 | 8/2010 | Bendall et al. | |
| 7,804,295 B2* | 9/2010 | Brandstrom | G01N 27/82 324/225 |
| 7,812,968 B2 | 10/2010 | Bendall et al. | |
| 7,821,649 B2 | 10/2010 | Bendall et al. | |
| 7,855,732 B2 | 12/2010 | Williams et al. | |
| 7,899,598 B2 | 3/2011 | Woon et al. | |
| 8,107,083 B2 | 1/2012 | Bendall et al. | |
| 8,165,351 B2 | 4/2012 | Bendall | |
| 8,300,920 B2 | 10/2012 | Chang et al. | |
| 8,411,083 B2 | 4/2013 | Bendall | |
| 8,422,030 B2 | 4/2013 | Bendall et al. | |
| 8,760,447 B2 | 6/2014 | Bendall et al. | |
| 8,810,636 B2 | 8/2014 | Bendall | |
| 8,960,012 B2* | 2/2015 | Dunford | G01M 5/0025 324/209 |
| 9,013,469 B2 | 4/2015 | Bendall | |
| 9,074,868 B2 | 7/2015 | Bendall et al. | |
| 2001/0018644 A1 | 8/2001 | Schwalb et al. | |
| 2002/0163573 A1 | 11/2002 | Bieman et al. | |
| 2003/0218607 A1* | 11/2003 | Baumberg | G06T 15/20 345/419 |
| 2004/0189799 A1 | 9/2004 | Spencer | |
| 2005/0052452 A1* | 3/2005 | Baumberg | G06T 15/20 345/419 |
| 2006/0150124 A1 | 7/2006 | Hornegger et al. | |
| 2006/0232583 A1 | 10/2006 | Petrov et al. | |
| 2006/0282009 A1 | 12/2006 | Oberg et al. | |
| 2007/0171220 A1* | 7/2007 | Kriveshko | A61C 13/0004 345/419 |
| 2007/0206204 A1 | 9/2007 | Jia et al. | |
| 2008/0198159 A1 | 8/2008 | Liu et al. | |
| 2009/0059242 A1 | 3/2009 | Fujieda et al. | |
| 2009/0158315 A1 | 6/2009 | Bendall et al. | |
| 2009/0225320 A1 | 9/2009 | Bendall et al. | |
| 2009/0225321 A1 | 9/2009 | Bendall et al. | |
| 2009/0225329 A1 | 9/2009 | Bendall et al. | |
| 2009/0225333 A1 | 9/2009 | Bendall et al. | |
| 2010/0284607 A1 | 11/2010 | Van Den Hengel et al. | |
| 2011/0187824 A1 | 8/2011 | Hori | |
| 2011/0205552 A1 | 8/2011 | Bendall et al. | |
| 2011/0210961 A1 | 9/2011 | Bendall et al. | |
| 2011/0221877 A1 | 9/2011 | Hori et al. | |
| 2012/0069012 A1 | 3/2012 | Facchin et al. | |
| 2012/0126803 A1* | 5/2012 | Goldfine | G01R 33/0064 324/239 |
| 2012/0223937 A1 | 9/2012 | Bendall | |
| 2012/0256901 A1 | 10/2012 | Bendall | |
| 2012/0314058 A1 | 12/2012 | Bendall et al. | |
| 2013/0009948 A1* | 1/2013 | Berger | G06T 19/00 345/419 |
| 2013/0287288 A1 | 10/2013 | Bendall | |
| 2015/0170352 A1 | 6/2015 | Bendall | |
| 2015/0170412 A1 | 6/2015 | Bendall et al. | |
| 2015/0187067 A1 | 7/2015 | Bendall et al. | |
| 2015/0302652 A1* | 10/2015 | Miller | G06F 3/011 345/419 |
| 2015/0317816 A1 | 11/2015 | Bendall et al. | |

FOREIGN PATENT DOCUMENTS

| | | |
|---|---|---|
| EP | 00888522 A1 | 1/1999 |
| GB | 2328280 A | 2/1999 |
| GB | 2505926 A | 3/2014 |
| JP | 11213177 A | 8/1999 |
| JP | 2001149319 A | 6/2001 |
| JP | 2005331488 A | 12/2005 |
| JP | 2007029460 A | 2/2007 |
| JP | 3898945 B2 | 3/2007 |
| JP | 2009053147 A | 3/2009 |
| WO | WO-2006056614 A1 | 6/2006 |
| WO | WO-2010107434 A1 | 9/2010 |

OTHER PUBLICATIONS

Unofficial English translation of Office Action issued in connection with related JP Application No. 2012-044901 dated Feb. 2, 2016.

(56) References Cited

OTHER PUBLICATIONS

Unofficial English translation of Office Action issued in connection with related CN Application No. 201210063764.6 dated Apr. 18, 2016.
International Search Report and Written Opinion issued in connection with related Application No. PCT/US2016/022312 dated Jul. 5, 2016.
Yerex et al. "Predictive Display Models for Tele-Manipulation from Uncalibrated Camera-Capture of Scene Geometry and Appearance", IEEE 2003.
Cobzas et al. "A Panoramic Model for Remote Robot Environment Mapping and Predictive Display", Published 2005.
Search Report and Written Opinion from EP Application No. 12157924.7 dated Jun. 22, 2012.
Miniaturized three-dimensional endoscopic imaging system based on active sterovision, Authors: Manhong Chan; Wumei Lin; Changehe Zhou; Qu Jianan Y, Applied Optics ISSN 003-6935 Coden Apopai, 2003, vol. 42, n10, pp. 1888-1898 (11 page article).
List of Related Cases; 1 page.

\* cited by examiner

GRAPHIC OVERLAY FOR MEASURING DIMENSIONS OF FEATURES USING A VIDEO INSPECTION DEVICE

CROSS-REFERENCE TO RELATED APPLICATIONS

This application is a Continuation-in-Part of, and claims priority to, U.S. patent application Ser. No. 15/018,628, filed Feb. 8, 2016, and entitled METHOD AND DEVICE FOR MEASURING FEATURES ON OR NEAR AN OBJECT, the entirety of which is incorporated herein by reference, which claimed the benefit of U.S. Provisional Patent Application No. 62/232,866, entitled METHOD AND SYSTEM FOR MEASURING FEATURES ON OR NEAR AN OBJECT, filed Sep. 25, 2015, the entirety of which is incorporated by reference herein by reference, and which is a Continuation-in-Part of, and claims priority to, U.S. patent application Ser. No. 14/660,464, filed Mar. 17, 2015, and entitled METHOD AND DEVICE FOR DISPLAYING A TWO-DIMENSIONAL IMAGE OF A VIEWED OBJECT SIMULTANEOUSLY WITH AN IMAGE DEPICTING THE THREE-DIMENSIONAL GEOMETRY OF THE VIEWED OBJECT, the entirety of which is incorporated herein by reference, and which is a Continuation-in-Part of, and claims priority to, both (1) U.S. patent application Ser. No. 14/108,976, filed Dec. 17, 2013, and entitled METHOD AND DEVICE FOR AUTOMATICALLY IDENTIFYING THE DEEPEST POINT ON THE SURFACE OF AN ANOMALY, the entirety of which is incorporated herein by reference, and (2) U.S. patent application Ser. No. 13/040,678, filed Mar. 4, 2011, and entitled METHOD AND DEVICE FOR DISPLAYING A THREE-DIMENSIONAL VIEW OF THE SURFACE OF A VIEWED OBJECT, now U.S. Pat. No. 9,013,469, the entirety of which is incorporated herein by reference.

BACKGROUND

The subject matter disclosed herein relates to a graphic overlay for measuring dimensions of features using a video inspection device.

Video inspection devices (or optical devices), such as video endoscopes or borescopes, can be used to inspect a surface of an object to identify and analyze anomalies (e.g., pits or dents) on the object that may have resulted from, e.g., damage, wear, corrosion, or improper installation. A video inspection device can be used to capture and display a two-dimensional image of the surface of a viewed object showing the anomaly to determine the dimensions of an anomaly on the surface. This two-dimensional image of the surface can be used to generate three-dimensional data of the surface that provides the three-dimensional coordinates (e.g., (x, y, z)) of a plurality of points on the surface.

In some instances, however, it may be difficult for a user to accurately place a cursor at a desired location on the two-dimensional image to take a measurement. For example, in a depth measurement, it may be difficult to visually determine, and place a cursor at, the deepest point in a dent or pit simply by viewing the two-dimensional image or even a three-dimensional point cloud view. Similarly, in making a length measurement across, e.g., a slot or weld, it may be difficult to visually determine, and place cursors at, points on each side of the slot or weld where the line formed between the points is normal (e.g., not diagonal) to each of the walls to provide an accurate width of the slot or weld. Likewise, it may be difficult for a user to accurately place cursors on the edge of a rounded turbine blade edge.

SUMMARY

A graphic overlay for measuring dimensions of features using a video inspection device is disclosed. An advantage that may be realized in the practice of some disclosed embodiments is that accurate measurements of object features can be taken.

In one embodiment, a method for measuring a feature is disclosed. The method includes the steps of displaying on a monitor an image of a viewed object, determining three-dimensional coordinates of a plurality of points on a surface of the viewed object using a central processor unit, placing one or more measurement cursors on the image using a pointing device, determining a measurement point corresponding to the location of at least one measurement cursor using the central processor unit, determining an edge plane using the central processor unit, wherein the edge plane passes through the measurement point, determining a distance between the plurality of points on a surface of the viewed object and the edge plane using a central processor unit, comparing the distance between the plurality of points on a surface of the viewed object and the edge plane to a predetermined distance threshold using the central processor unit, and displaying an edge plane graphical overlay on pixels in the image associated with the plurality of points on a surface of the viewed object having a distance to the edge plane that is below the predetermined distance threshold.

In another embodiment, the method includes the steps of displaying on a monitor an image of a viewed object, determining three-dimensional coordinates of a plurality of points on a surface of the viewed object using a central processor unit, placing a first measurement cursor and a second measurement cursor on the image using a pointing device, determining a first measurement point corresponding to the location of the first measurement cursor using the central processor unit, determining a second measurement point corresponding to the location of the second measurement cursor using the central processor unit, determining a three-dimensional line between the first measurement point and the second measurement point using the central processor unit, determining a first edge plane using the central processor unit, wherein the first edge plane is normal to the three-dimensional line and passes through the first measurement point, determining a distance between the plurality of points on a surface of the viewed object and the first edge plane using a central processor unit, comparing the distance between the plurality of points on a surface of the viewed object and the first edge plane to a predetermined distance threshold using the central processor unit, and displaying a first edge plane graphical overlay on pixels in the image associated with the plurality of points on a surface of the viewed object having a distance to the first edge plane that is below the predetermined distance threshold.

In yet another embodiment, the method includes the steps of displaying on a monitor an image of a viewed object, determining three-dimensional coordinates of a plurality of points on a surface of the viewed object using a central processor unit, placing a first measurement cursor, a second measurement cursor, and a third measurement cursor on the image using a pointing device, determining a first measurement point corresponding to the location of the first measurement cursor using the central processor unit, determining a second measurement point corresponding to the location of the second measurement cursor using the central processor unit, determining a third measurement point corresponding to the location of the third measurement cursor using the central processor unit, determining a three-dimensional reference line between the first measurement point and the second measurement point using the central processor unit, determining a three-dimensional length line between the third measurement point and the three-dimensional reference line using the central processor unit, determining a first edge plane using the central processor unit, wherein the first edge plane is normal to the three-dimensional length line and passes through the first measurement point and the second measurement point, determining a distance between the plurality of points on a surface of the viewed object and the first edge plane using a central processor unit, comparing the distance between the plurality of points on a surface of the viewed object and the first edge plane to a predetermined distance threshold using the central processor unit, and displaying a first edge plane graphical overlay on pixels in the image associated with the plurality of points on a surface of the viewed object having a distance to the first edge plane that is below the predetermined distance threshold.

In still another embodiment, the method includes the steps of displaying on a monitor an image of a viewed object, determining three-dimensional coordinates of a plurality of points on a surface of the viewed object using a central processor unit, selecting one or more reference surface points from the plurality of points on the surface of the viewed object using a pointing device, determining a reference surface using the central processor unit, wherein the reference surface is determined based on the one or more of the reference surface points, placing a measurement cursor on the image using the pointing device, determining a measurement point corresponding to the location of the measurement cursor using the central processor unit, determining a depth plane using the central processor unit, wherein the depth plane is parallel to the reference surface and passes through the measurement point, determining a distance between the plurality of points on a surface of the viewed object and the depth plane using the central processor unit, comparing the distance between the plurality of points on a surface of the viewed object and the depth plane to a predetermined distance threshold using the central processor unit, and displaying a depth plane graphical overlay on pixels in the image associated with the plurality of points on a surface of the viewed object having a distance to the depth plane that is below the predetermined distance threshold.

The above embodiments are exemplary only. Other embodiments are within the scope of the disclosed subject matter.

BRIEF DESCRIPTION OF THE SEVERAL VIEWS OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the disclosed subject matter encompasses other embodiments as well. The drawings are not necessarily to scale, emphasis generally being placed upon illustrating the features of certain embodiments of the invention. In the drawings, like numerals are used to indicate like parts throughout the various views.

FIG. 30B is a side-by-side image displaying a two-dimensional image of an edge of a turbine blade and a three-dimensional point cloud view of the edge of the turbine blade illustrating edge plane graphic overlays where the measurement cursors are located on the edge of the turbine blade; and.

DETAILED DESCRIPTION

Embodiments of the disclosed subject matter relate to graphic overlays for measuring dimensions of features on or near an object using a video inspection device. For example, an inspector using a video inspection device to identify and measure the dimensions of anomalies on an object (e.g., a crack in a turbine blade) places measurement cursors on the pixels of the image of the object to measure the dimensions of the anomaly in order to determine whether maintenance is required to repair the anomaly. In order to facilitate accurate measurements, a semi-transparent graphic overlay can be placed on pixels of the image of the object associated with the location of the measurement cursors. The semi-transparent graphic overlays give a visual indication to a user when conducting a measurement of an anomaly on the object whether the measurement cursors are placed in the correct locations to take an accurate measurement of the anomaly. For example, if the measurement cursors are not placed in the correct location, the semi-transparent graphic overlays will clearly indicate to the user that the cursors must be relocated to obtain an accurate measurement of the dimensions of the anomaly. Other embodiments are within the scope of the disclosed subject matter.

Figure 1:
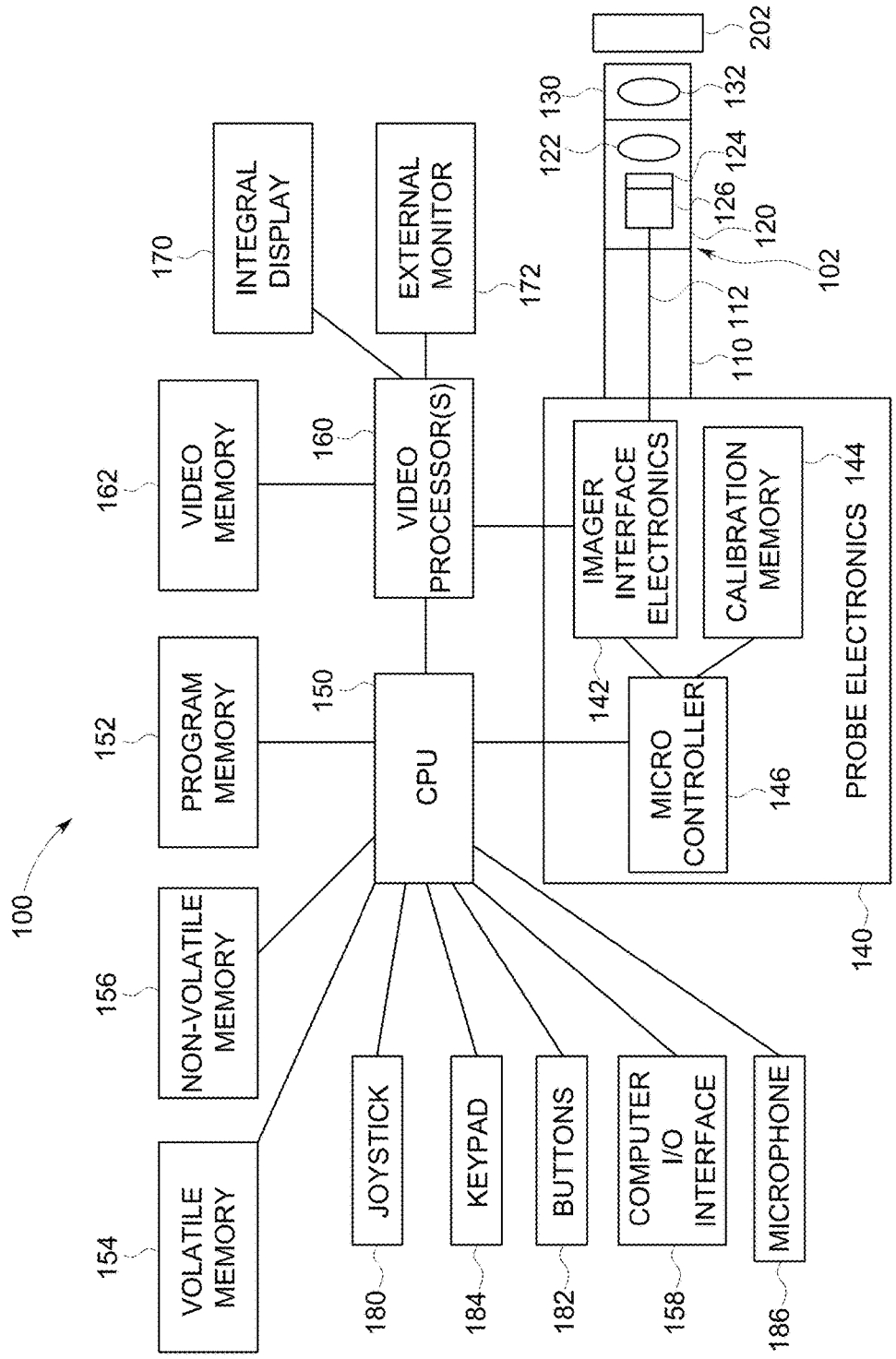
FIG. 1 is a block diagram of an exemplary video inspection device.

FIG. 1 is a block diagram of an exemplary video inspection device 100. It will be understood that the video inspection device 100 shown in FIG. 1 is exemplary and that the scope of the invention is not limited to any particular video inspection device 100 or any particular configuration of components within a video inspection device 100.

Video inspection device 100 can include an elongated probe 102 comprising an insertion tube 110 and a head assembly 120 disposed at the distal end of the insertion tube 110. Insertion tube 110 can be a flexible, tubular section through which all interconnects between the head assembly 120 and probe electronics 140 are passed. Head assembly 120 can include probe optics 122 for guiding and focusing light from the viewed object 202 onto an imager 124. The probe optics 122 can comprise, e.g., a lens singlet or a lens having multiple components. The imager 124 can be a solid state CCD or CMOS image sensor for obtaining an image of the viewed object 202.

A detachable tip or adaptor 130 can be placed on the distal end of the head assembly 120. The detachable tip 130 can include tip viewing optics 132 (e.g., lenses, windows, or apertures) that work in conjunction with the probe optics 122 to guide and focus light from the viewed object 202 onto an imager 124. The detachable tip 130 can also include illumination LEDs (not shown) if the source of light for the video inspection device 100 emanates from the tip 130 or a light passing element (not shown) for passing light from the probe 102 to the viewed object 202. The tip 130 can also provide the ability for side viewing by including a waveguide (e.g., a prism) to turn the camera view and light output to the side. The tip 130 may also provide stereoscopic optics or structured-light projecting elements for use in determining three-dimensional data of the viewed surface. The elements that can be included in the tip 130 can also be included in the probe 102 itself The imager 124 can include a plurality of pixels formed in a plurality of rows and columns and can generate image signals in the form of analog voltages representative of light incident on each pixel of the imager 124. The image signals can be propagated through imager hybrid 126, which provides electronics for signal buffering and conditioning, to an imager harness 112, which provides wires for control and video signals between the imager hybrid 126 and the imager interface electronics 142. The imager interface electronics 142 can include power supplies, a timing generator for generating imager clock signals, an analog front end for digitizing the imager video output signal, and a digital signal processor for processing the digitized imager video data into a more useful video format.

The imager interface electronics 142 are part of the probe electronics 140, which provide a collection of functions for operating the video inspection device 10. The probe electronics 140 can also include a calibration memory 144, which stores the calibration data for the probe 102 and/or tip 130. A microcontroller 146 can also be included in the probe electronics 140 for communicating with the imager interface electronics 142 to determine and set gain and exposure settings, storing and reading calibration data from the calibration memory 144, controlling the light delivered to the viewed object 202, and communicating with a central processor unit (CPU) 150 of the video inspection device 100.

In addition to communicating with the microcontroller 146, the imager interface electronics 142 can also communicate with one or more video processors 160. The video processor 160 can receive a video signal from the imager interface electronics 142 and output signals to various monitors 170, 172, including an integral display 170 or an external monitor 172. The integral display 170 can be an LCD screen built into the video inspection device 100 for displaying various images or data (e.g., the image of the viewed object 202, menus, cursors, measurement results) to an inspector. The external monitor 172 can be a video monitor or computer-type monitor connected to the video inspection device 100 for displaying various images or data.

The video processor 160 can provide/receive commands, status information, streaming video, still video images, and graphical overlays to/from the CPU 150 and may be comprised of FPGAs, DSPs, or other processing elements which provide functions such as image capture, image enhancement, graphical overlay merging, distortion correction, frame averaging, scaling, digital zooming, overlaying, merging, flipping, motion detection, and video format conversion and compression.

The CPU 150 can be used to manage the user interface by receiving input via a joystick 180, buttons 182, keypad 184, and/or microphone 186, in addition to providing a host of other functions, including image, video, and audio storage and recall functions, system control, and measurement processing. The joystick 180 can be manipulated by the user to perform such operations as menu selection, cursor movement, slider adjustment, and articulation control of the probe 102, and may include a push-button function. The buttons 182 and/or keypad 184 also can be used for menu selection and providing user commands to the CPU 150 (e.g., freezing or saving a still image). The microphone 186 can be used by the inspector to provide voice instructions to freeze or save a still image.

The video processor 160 can also communicate with video memory 162, which is used by the video processor 160 for frame buffering and temporary holding of data during processing. The CPU 150 can also communicate with CPU program memory 152 for storage of programs executed by the CPU 150. In addition, the CPU 150 can be in communication with volatile memory 154 (e.g., RAM), and non-volatile memory 156 (e.g., flash memory device, a hard drive, a DVD, or an EPROM memory device). The non-volatile memory 156 is the primary storage for streaming video and still images.

The CPU 150 can also be in communication with a computer I/O interface 158, which provides various interfaces to peripheral devices and networks, such as USB, Firewire, Ethernet, audio I/O, and wireless transceivers. This computer I/O interface 158 can be used to save, recall, transmit, and/or receive still images, streaming video, or audio. For example, a USB "thumb drive" or CompactFlash memory card can be plugged into computer I/O interface 158. In addition, the video inspection device 100 can be configured to send frames of image data or streaming video data to an external computer or server. The video inspection device 100 can incorporate a TCP/IP communication protocol suite and can be incorporated in a wide area network including a plurality of local and remote computers, each of the computers also incorporating a TCP/IP communication protocol suite. With incorporation of TCP/IP protocol suite, the video inspection device 100 incorporates several transport layer protocols including TCP and UDP and several different layer protocols including HTTP and FTP.

It will be understood that, while certain components have been shown as a single component (e.g., CPU 150) in FIG. 1, multiple separate components can be used to perform the functions of the CPU 150.

Figure 2:
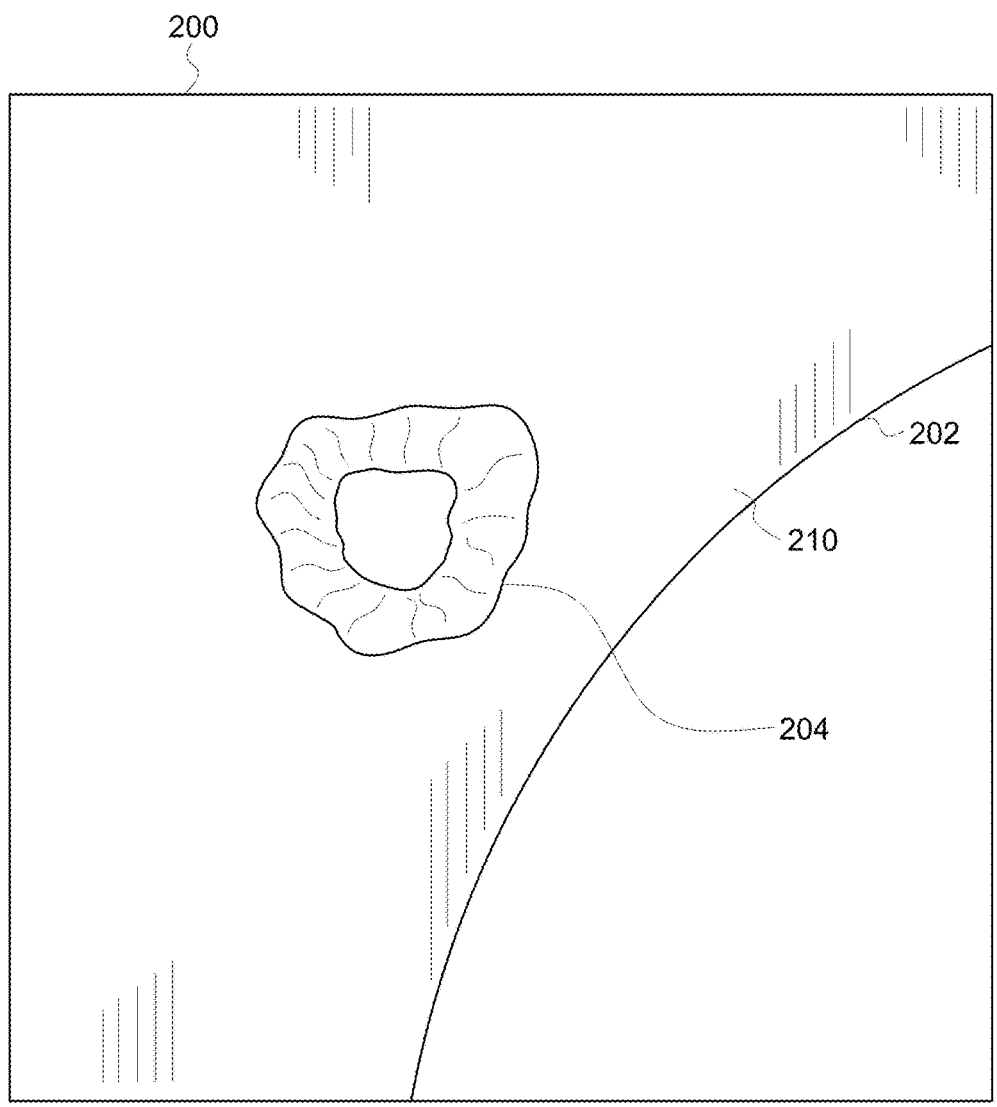
FIG. 2 is an exemplary image obtained by the video inspection device of the object surface of a viewed object having an anomaly in an exemplary embodiment.

FIG. 2 is an exemplary image 200 obtained by the video inspection device 100 of the object surface 210 of a viewed object 202 having an anomaly 204 in an exemplary embodiment of the invention. In this example, the anomaly 204 is shown as a dent, where material has been removed from the object surface 210 of the viewed object 202 in the anomaly 204 by damage or wear. It will be understood that the anomaly 204 shown in this exemplary embodiment is just an example and that the inventive method applies to other types of irregularities (e.g., cracks, corrosion pitting, coating loss, surface deposits, etc.). Once the image 200 is obtained, and the anomaly 204 is identified, the image 200 can be used to determine the dimensions of the anomaly 204 (e.g., height or depth, length, width, area, volume, point to line, profile slice, etc.). In one embodiment, the image 200 used can be a two-dimensional image 200 of the object surface 210 of the viewed object 202, including the anomaly 204.

Figure 3:
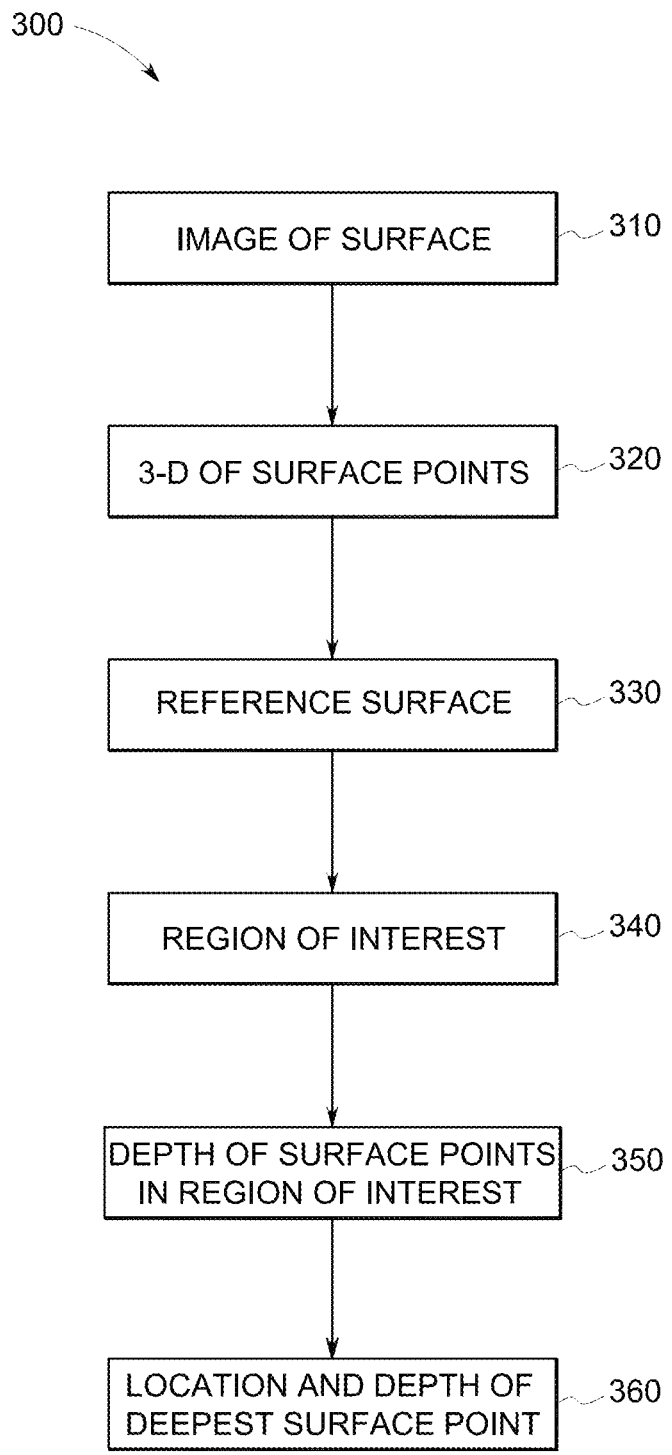
FIG. 3 is a flow diagram of an exemplary method for automatically identifying the deepest point on the surface of an anomaly on a viewed object shown in the image of FIG. 2 in an exemplary embodiment.

FIG. 3 is a flow diagram of an exemplary method 300 for automatically identifying the deepest point on the object surface 210 of an anomaly 204 on a viewed object 202 shown in the image 200 of FIG. 2 in an exemplary embodiment of the invention. It will be understood that the steps described in the flow diagram of FIG. 3 can be performed in a different order than shown in the flow diagram and that not all of the steps are required for certain embodiments.

At step 310 of the exemplary method 300 (FIG. 3) and as shown in FIG. 2, the user can use the video inspection device 100 (e.g., the imager 124) to obtain at least one image 200 of the object surface 210 of a viewed object 202 having an anomaly 204 and display it on a video monitor (e.g., an integral display 170 or external monitor 172). In one embodiment, the image 200 can be displayed in a measurement mode of the video inspection device.

At step 320 of the exemplary method 300 (FIG. 3), the video inspection device 100 (e.g., the CPU 150) can determine the three-dimensional coordinates (e.g., (x, y, z)) of a plurality of surface points on the object surface 210 of the viewed object 202, including surface points of the anomaly 204. In one embodiment, the video inspection device can generate three-dimensional data from the image 200 in order to determine the three-dimensional coordinates. Several different existing techniques can be used to provide the three-dimensional coordinates of the surface points in the image 200 (FIG. 2) of the object surface 210 (e.g., stereo, scanning systems, stereo triangulation, structured light methods such as phase shift analysis, phase shift moire, laser dot projection, etc.).

Most such techniques comprise the use of calibration data, which, among other things, includes optical characteristic data that is used to reduce errors in the three-dimensional coordinates that would otherwise be induced by optical distortions. With some techniques, the three-dimensional coordinates may be determined using one or more images captured in close time proximity that may include projected patterns and the like. It is to be understood that references to three-dimensional coordinates determined using image 200 may also comprise three-dimensional coordinates determined using one or a plurality of images 200 of the object surface 210 captured in close time proximity, and that the image 200 displayed to the user during the described operations may or may not actually be used in the determination of the three-dimensional coordinates.

Figure 4:
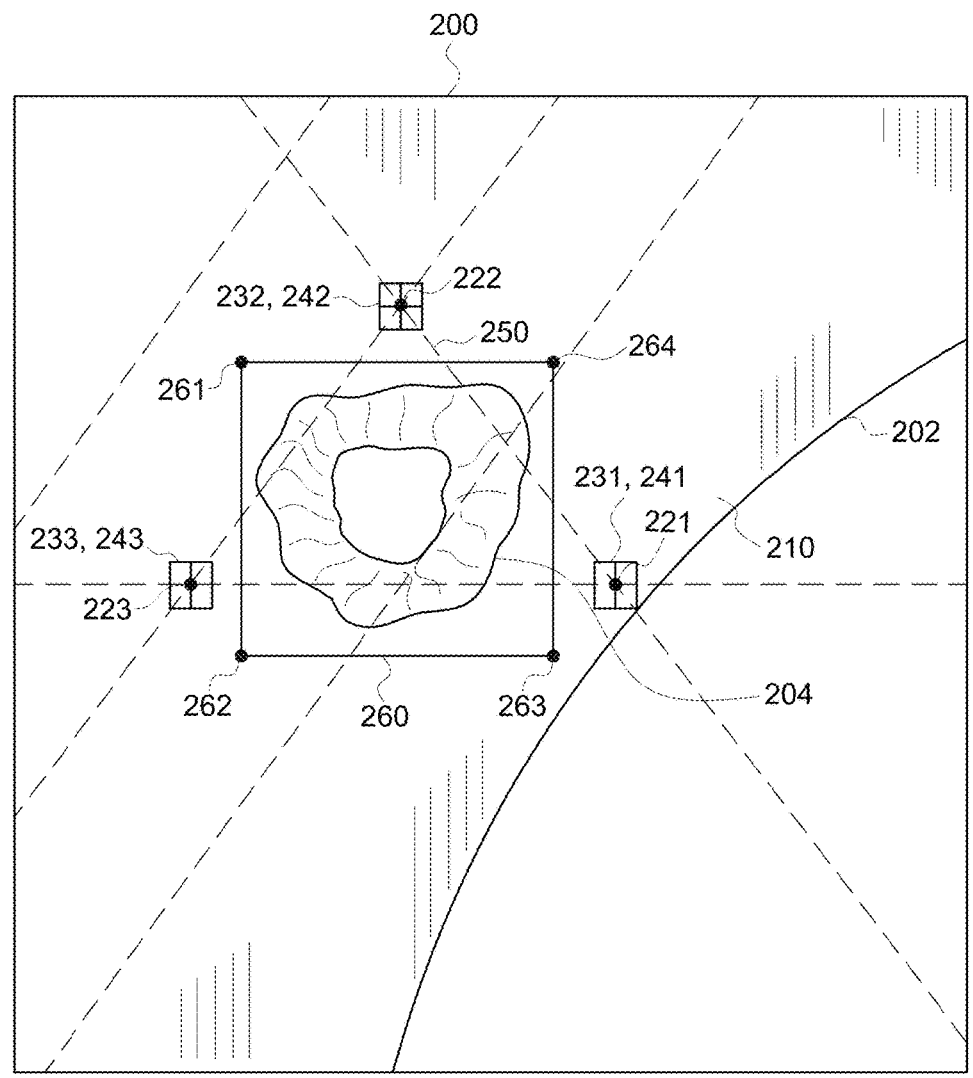
FIG. 4 illustrates an exemplary reference surface determined by the video inspection device.

At step 330 of the exemplary method 300 (FIG. 3), and as shown in FIG. 4, the video inspection device 100 (e.g., the CPU 150) can determine a reference surface 250. In some embodiments, the reference surface 250 can be flat, while in other embodiments the reference surface 250 can be curved. Similarly, in one embodiment, the reference surface 250 can be in the form of a plane, while in other embodiments, the reference surface 250 can be in the form of a different shape (e.g., cylinder, sphere, etc.). For example, a user can use the joystick 180 (or other pointing device (e.g., mouse, touch screen, etc.)) of the video inspection device 100 to select one or more reference surface points on the object surface 210 of the viewed object 202 proximate to the anomaly 204 to determine a reference surface.

In one embodiment and as shown in FIG. 4, a total of three reference surface points 221, 222, 223 are selected on the object surface 210 of the viewed object 202 proximate to the anomaly 204 to conduct a depth measurement of the anomaly 204, with the three reference surface points 221, 222, 223 selected on the object surface 210 proximate to the anomaly 204. In one embodiment, the plurality of reference surface points 221, 222, 223 on the object surface 210 of the viewed object 202 can be selected by placing reference surface cursors 231, 232, 233 (or other pointing devices) on pixels 241, 242, 243 of the image 200 corresponding to the plurality of reference surface points 221, 222, 223 on the object surface 210. In the exemplary depth measurement, the video inspection device 100 (e.g., the CPU 150) can determine the three-dimensional coordinates of each of the plurality of reference surface points 221, 222, 223.

The three-dimensional coordinates of three or more surface points proximate to one or more of the three reference surface points 221, 222, 223 selected on the object surface 210 proximate to the anomaly 204 can be used to determine a reference surface 250 (e.g., a plane). In one embodiment, the video inspection device 100 (e.g., the CPU 150) can perform a curve fitting of the three-dimensional coordinates of the three reference surface points 221, 222, 223 to determine an equation for the reference surface 250 (e.g., for a plane) having the following form:

$$k_{0RS} + k_{1RS1} \cdot x_{iRS} + k_{2RS} \cdot y_{iRS1} = z_{iRS} \quad (1)$$

where ($x_{iRS}$, $y_{iRS}$, $z_{iRS}$) are coordinates of any three-dimensional point on the defined reference surface 250 and $k_{0RS}$, $k_{1RS}$, and $k_{2RS}$ are coefficients obtained by a curve fitting of the three-dimensional coordinates.

It should be noted that a plurality of reference surface points (i.e., at least as many points as the number of k coefficients) are used to perform the curve fitting. The curve fitting finds the k coefficients that give the best fit to the points used (e.g., least squares approach). The k coefficients then define the plane or other reference surface 250 that approximates the three-dimensional points used. However, if more points are used in the curve fitting than the number of k coefficients, when you insert the x and y coordinates of the points used into the plane equation (1), the z results will generally not exactly match the z coordinates of the points due to noise and any deviation from a plane that may actually exist. Thus, the $x_{iRS1}$ and $y_{iRS1}$ can be any arbitrary values, and the resulting $z_{iRS}$ tells you the z of the defined plane at $x_{iRS}$, $y_{iRS}$. Accordingly, coordinates shown in these equations can be for arbitrary points exactly on the defined surface, not necessarily the points used in the fitting to determine the k coefficients.

In other embodiments, there are only one or two reference surface points selected, prohibiting the use of curve fitting based only on the three-dimensional coordinates of those reference surface points since three points are needed to determine $k_{0RS}$, $k_{1RS}$, and $k_{2RS}$. In that case, the video inspection device 100 (e.g., the CPU 150) can identify a plurality of pixels proximate to each of the pixels of the image corresponding to a plurality of points on the object surface 210 proximate to the reference surface point(s), and determine the three-dimensional coordinates of the proximate point(s), enabling curve fitting to determine a reference surface 250.

While the exemplary reference surface 250 has been described as being determined based on reference surface points 221, 222, 223 selected by reference surface cursors 231, 232, 233, in other embodiments, the reference surface 250 can be formed by using a pointing device to place a reference surface shape 260 (e.g., circle, square, rectangle, triangle, etc.) proximate to anomaly 204 and using the reference surface points 261, 262, 263, 264 of the shape 260 to determine the reference surface 250. It will be understood that the reference surface points 261, 262, 263, 264 of the shape 260 can be points selected by the pointing device or be other points on or proximate to the perimeter of the shape that can be sized to enclose the anomaly 204.

Figure 5:
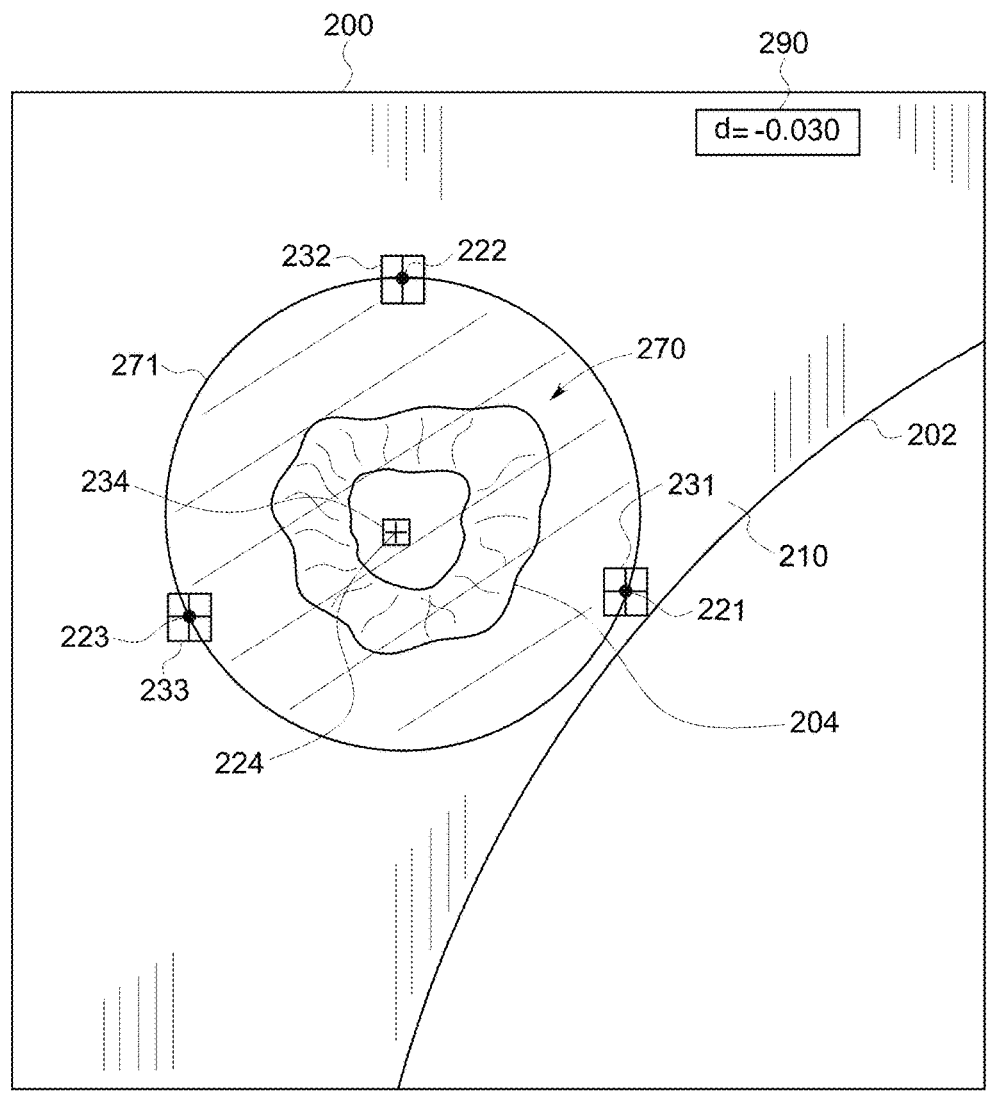
FIG. 5 illustrates an exemplary region of interest determined by the video inspection device.

At step 340 of the exemplary method 300 (FIG. 3), and as shown in FIG. 5, the video inspection device 100 (e.g., the CPU 150) determines a region of interest 270 proximate to the anomaly 204 based on the reference surface points of the reference surface 250. The region of interest 270 includes a plurality of surface points of the anomaly 204. In one embodiment, a region of interest 270 is formed by forming a region of interest shape 271 (e.g., a circle) based on two or more of the reference surface points 221, 222, 223. In another embodiment, the region of interest 270 can be determined by forming a cylinder perpendicular to the reference surface 260 and passing it through or proximate to two or more of the reference surface points 221, 222, 223. Referring again to FIG. 4, a region of interest could be formed within the reference surface shape 260 and reference surface points 261, 262, 263, 264.

Figure 6:
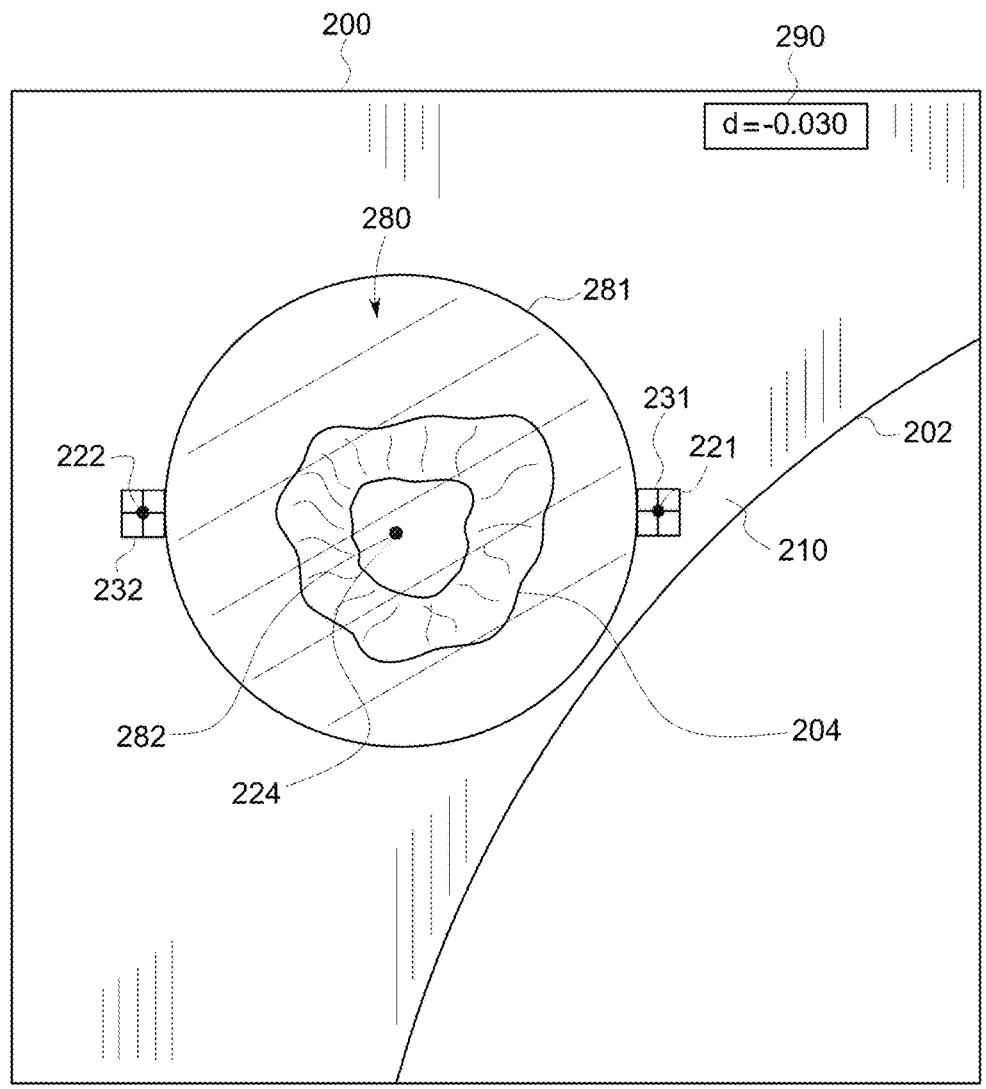
FIG. 6 illustrates another exemplary region of interest determined by the video inspection device.

Although the exemplary region of interest shape 271 in FIG. 5 is formed by passing through the reference surface points 221, 222, 223, in another embodiment, a smaller diameter reference surface shape can be formed by passing only proximate to the reference surface points. For example, as shown in FIG. 6, a region of interest 280 is formed by passing a region of interest shape 281 (e.g., a circle) proximate to two of the reference surface points 221, 222, where the diameter of the circle 281 is smaller than the distance between the two reference surface points 221, 222. It will be understood that region of interest shapes 271, 281 and the regions of interest 270, 280 may or may not be displayed on the image 200.

After the region of interest 270, 280 is determined, at step 350 of the exemplary method 300 (FIG. 3), the video inspection device 100 (e.g., the CPU 150) determines the distance (i.e., depth) from each of the plurality of surface points in the region of interest to the reference surface 250. In one embodiment, the video inspection device 100 (e.g., the CPU 150) determines the distance of a line extending between the reference surface 250 and each of the plurality of surface points in the region of interest 270, 280, wherein the line perpendicularly intersects the reference surface 250.

At step 360 of the exemplary method 300 (FIG. 3), the video inspection device determines the location of the deepest surface point 224 in the region of interest 270, 280 by determining the surface point that is furthest from the reference surface 250 (e.g., selecting the surface point with the longest line extending to the reference surface 250). It will be understood that, as used herein, the "deepest point" or "deepest surface point" can be a furthest point that is recessed relative to the reference surface 250 or a furthest point (i.e., highest point) that is protruding from the references surface 250. The video inspection device 100 can identify the deepest surface point 224 in the region of interest 270, 280 on the image by displaying, e.g., a cursor 234 (FIG. 5) or other graphic identifier 282 (FIG. 6) on the deepest surface point 224. In addition and as shown in FIGS. 5 and 6, the video inspection device 100 can display the depth 290 (in inches or millimeters) of the deepest surface point 224 in the region of interest 270, 280 on the image 200 (i.e., the length of the perpendicular line extending from the deepest surface point 224 to the reference surface 250. By automatically displaying the cursor 234 or other graphic identifier 282 (FIG. 6) at the deepest surface point 224 in the region of interest 270, 280, the video inspection device 100 reduces the time required to perform the depth measurement and improves the accuracy of the depth measurement since the user does not need to manually identify the deepest surface point 224 in the anomaly 204.

Once the cursor 234 has been displayed at the deepest surface point 224 in the region of interest 270, 280, the user can select that point to take and save a depth measurement. The user can also move the cursor 234 within the region of interest 270, 280 to determine the depth of other surface points in the region of interest 270, 280. In one embodiment, the video inspection device 100 (e.g., CPU 150) can monitor the movement of the cursor 234 and detect when the cursor 234 has stopped moving. When the cursor 234 stops moving for a predetermined amount of time (e.g., 1 second), the video inspection device 100 (e.g., the CPU 150) can determine the deepest surface point proximate to the cursor 234 (e.g., a predetermined circle centered around the cursor 234) and automatically move the cursor 234 to that position.

Figure 7:
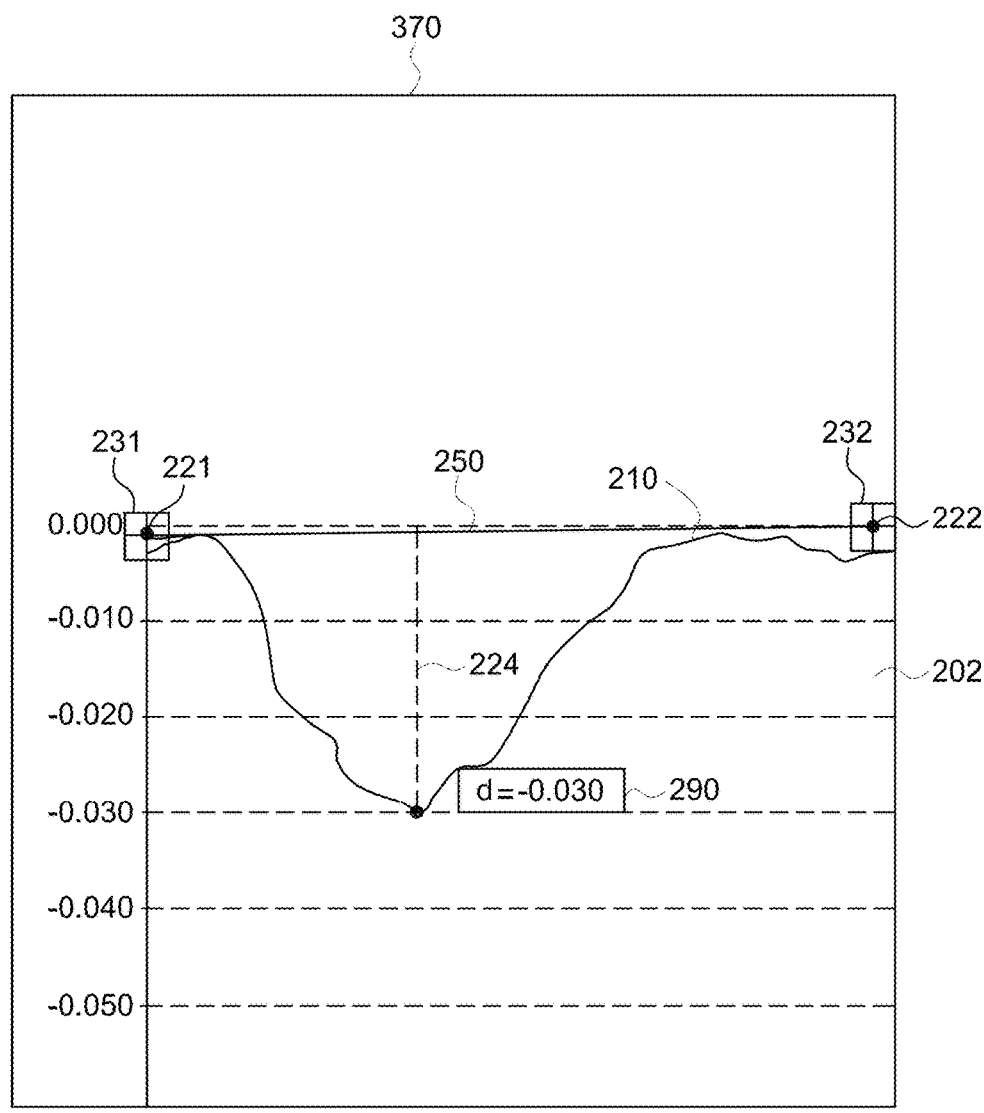
FIG. 7 is a graphical representation of an exemplary profile of the object surface of the viewed object shown in the image of FIG. 1 in an exemplary embodiment.

FIG. 7 is a graphical representation of an exemplary profile 370 of the object surface 210 of the viewed object 202 shown in the image 200 of FIG. 1. In this exemplary profile 370, the reference surface 250 is shown extending between two reference surface points 221, 222 and their respective reference surface cursors 231, 232. The location and depth 290 of the deepest surface point 224 in the region of interest is also shown in the graphical representation. In another embodiment, a point cloud view can also be used to show the deepest surface point 224.

Figure 8:
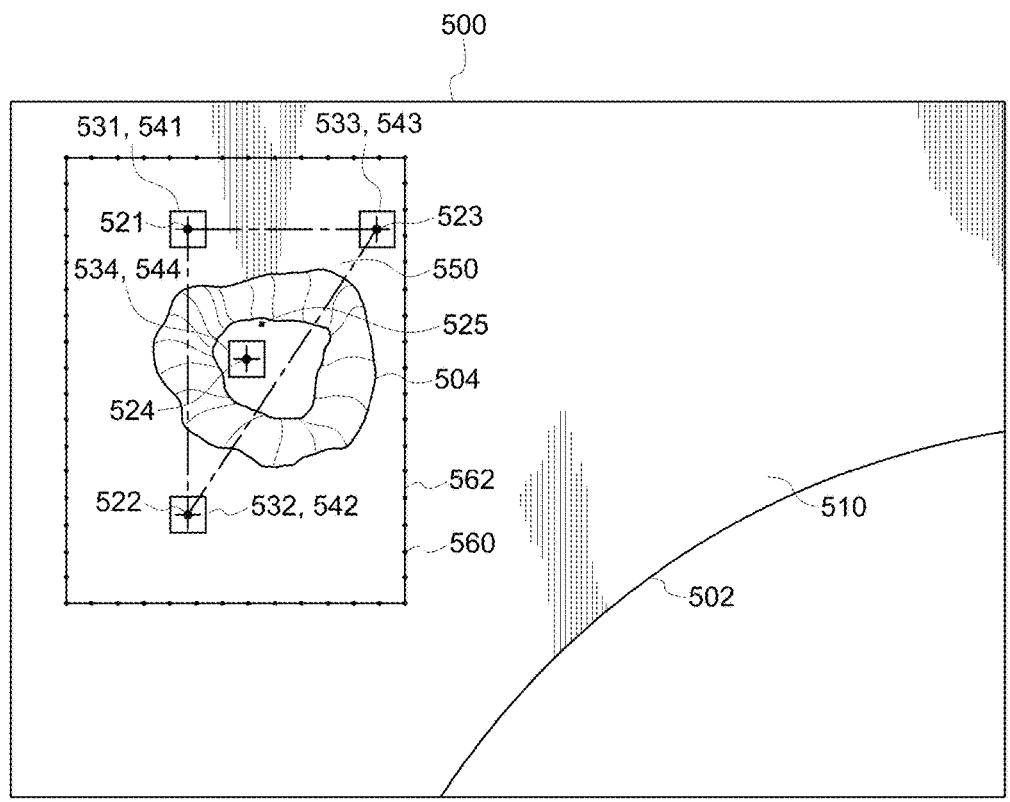
FIG. 8 is another image obtained by the video inspection device of the surface of a viewed object having an anomaly in an exemplary embodiment.

FIG. 8 is another image 500 obtained by the video inspection device 100 of the object surface 510 of a viewed object 502 having an anomaly 504 in an exemplary embodiment of the invention. Once again, in this example, the anomaly 504 is shown as a dent, where material has been removed from the object surface 510 of the viewed object 502 in the anomaly 504 by damage or wear. It will be understood that the anomaly 504 shown in this exemplary embodiment is just an example and that the inventive method applies to other types of irregularities (e.g., cracks, corrosion pitting, coating loss, surface deposits, etc.). Once the image 500 is obtained, and the anomaly 504 is identified, the image 500 can be used to determine the dimensions of the anomaly 504 (e.g., height or depth, length, width, area, volume, point to line, profile slice, etc.). In one embodiment, the image 500 used can be a two-dimensional image 500 of the object surface 510 of the viewed object 502, including the anomaly 504.

Figure 9:
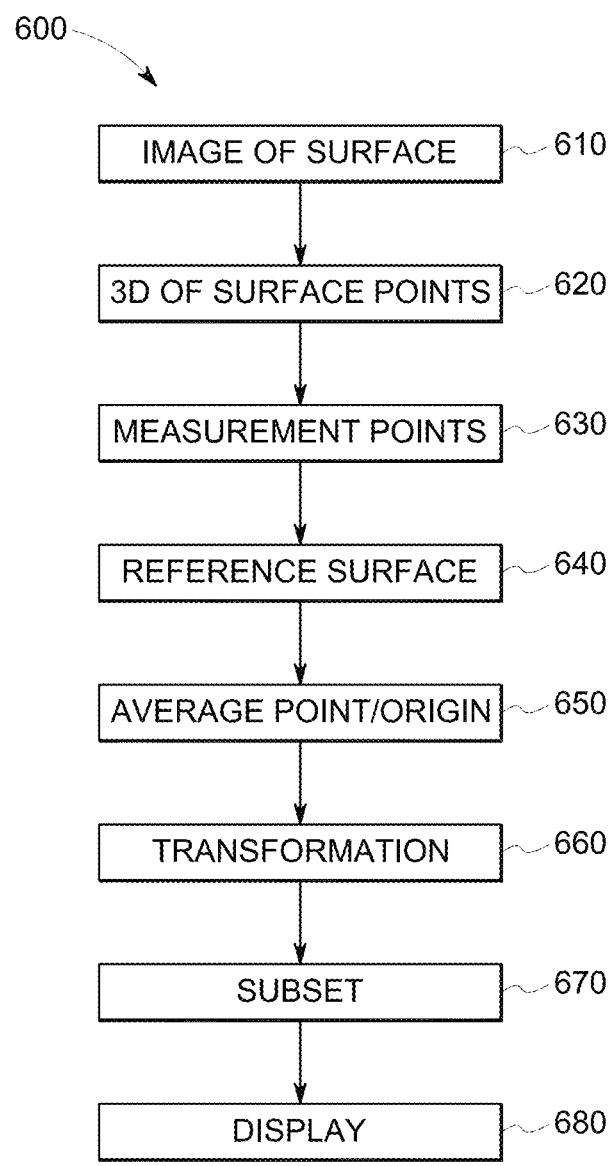
FIG. 9 is a flow diagram of a method for displaying three-dimensional data for inspection of the surface of the viewed object shown in the image of FIG. 8 in an exemplary embodiment.

FIG. 9 is a flow diagram of a method 600 for displaying three-dimensional data for inspection of the object surface 510 of the viewed object 502 shown in the image 500 of FIG. 8 in an exemplary embodiment of the invention. It will be understood that the steps described in the flow diagram of FIG. 9 can be performed in a different order than shown in the flow diagram and that not all of the steps are required for certain embodiments.

At step 610, and as shown in FIG. 8, the operator can use the video inspection device 100 to obtain an image 500 of the object surface 510 of a viewed object 502 having an anomaly 504 and display it on a video monitor (e.g., an integral display 170 or external monitor 172). In one embodiment, the image 500 can be displayed in a measurement mode of the video inspection device.

At step 620, the CPU 150 of the video inspection device 100 can determine the three-dimensional coordinates ($x_{iS1}$, $y_{iS1}$, $z_{iS1}$) in a first coordinate system of a plurality of surface points on the object surface 510 of the viewed object 502, including the anomaly 504. In one embodiment, the video inspection device can generate three-dimensional data from the image 500 in order to determine the three-dimensional coordinates. As discussed above, several different existing techniques can be used to provide the three-dimensional coordinates of the points on the image 500 of the object surface 510 (e.g., stereo, scanning systems, structured light methods such as phase shifting, phase shift moire, laser dot projection, etc.).

At step 630, and as shown in FIG. 8, an operator can use the joystick 180 (or other pointing device (e.g., mouse, touch screen)) of the video inspection device 100 to select a plurality of measurement points on the object surface 510 of the viewed object 502 proximate the anomaly 504 to conduct a particular type of measurement. The number of measurement points selected is dependent upon the type measurement to be conducted. Certain measurements can require selection of two measurement points (e.g., length, profile), while other measurements can require selection of three or more measurement points (e.g., point-to-line, area, multi-segment). In one embodiment and as shown in FIG. 8, a total of four measurement points 521, 522, 523, 524 are selected on the object surface 510 of the viewed object 502 proximate the anomaly 504 to conduct a depth measurement of the anomaly 504, with three of the measurement points 521, 522, 523 selected on the object surface 510 proximate the anomaly 504, and the fourth measurement point 524 selected to be at the deepest point of the anomaly 504. In one embodiment, the plurality of measurement points 521, 522, 523, 524 on the object surface 510 of the viewed object 502 can be selected by placing cursors 531, 532, 533, 534 (or other pointing devices) on pixels 541, 542, 543, 544 of the image 500 corresponding to the plurality of measurement points 521, 522, 523, 524 on the object surface 510. In the exemplary depth measurement, the video inspection device 100 can determine the three-dimensional coordinates in the first coordinate system of each of the plurality of measurement points 521, 522, 523, 524. It will be understood that the inventive method is not limited to depth measurements or measurements involving four selected measurement points, but instead applies to various types of measurements involving different numbers of points, including those discussed above.

At step 640, and as shown in FIG. 8, the CPU 150 of the video inspection device 100 can determine a reference surface 550. In the exemplary depth measurement of the anomaly 504 shown in FIG. 8, the three-dimensional coordinates of three or more surface points proximate one or more of the three measurement points 521, 522, 523 selected on the object surface 510 proximate the anomaly 504 can be used to determine a reference surface 550 (e.g., a plane). In one embodiment, the video inspection device 100 can perform a curve fitting of the three-dimensional coordinates in the first coordinate system of the three measurement points 521, 522, 523 ($x_{iM1}$, $y_{iM1}$, $z_{iM1}$) to determine an equation for the reference surface 550 (e.g., for a plane) having the following form:

$$k_{0RS1}+k_{1RS1}\cdot x_{iRS1}+k_{2RS1}\cdot y_{iRS1}=z_{iRS1} \quad (2)$$

where ($x_{iRS1}$, $y_{iRS1}$, $z_{iRS1}$) are coordinates of any three-dimensional point in the first coordinate system on the defined reference surface 550 and $k_{0RS1}$, $k_{iRS1}$, and $k_{1RS1}$ are coefficients obtained by a curve fitting of the three-dimensional coordinates in the first coordinate system.

It should be noted that a plurality of measurement points (i.e., at least as many points as the number of k coefficients) are used to perform the curve fitting. The curve fitting finds the k coefficients that give the best fit to the points used (e.g., least squares approach). The k coefficients then define the plane or other reference surface 550 that approximates the three-dimensional points used. However, if more points are used in the curve fitting than the number of k coefficients, when you insert the x and y coordinates of the points used into the plane equation (2), the z results will generally not exactly match the z coordinates of the points due to noise and any deviation from a plane that may actually exist. Thus, the $x_{iRS1}$ and $y_{iRS1}$ can be any arbitrary values, and the resulting $z_{iRS1}$ tells you the z of the defined plane at $x_{iRS1}$, $y_{iRS1}$. Accordingly, coordinates shown in these equations can be for arbitrary points exactly on the defined surface, not necessarily the points used in the fitting to determine the k coefficients.

In another embodiment, there are only two measurement points selected for a particular measurement (e.g., length, profile), prohibiting the use of curve fitting based only on the three-dimensional coordinates of those two measurement points since three points are needed to determine $k_{0RS1}$, $k_{1RS1}$, and $k_{2RS1}$. In that case, the video inspection device 100 can identify a plurality of pixels proximate each of the pixels of the image corresponding to a plurality of points on the object surface 510 proximate each of the measurement points, and determine the three-dimensional coordinates of those points, enabling curve fitting to determine a reference surface 550.

In one embodiment and as shown in FIG. 8, the video inspection device 100 can determine the three-dimensional coordinates in the first coordinate system of a plurality of frame points 560 ($x_{iF1}$, $y_{iF1}$, $z_{iF1}$) forming a frame 562 (e.g., a rectangle) on the reference surface 550 around the anomaly 504 and the measurement points 521, 522, 523, 524, which can be used later to display the location of the reference surface 550.

Once the reference surface 550 is determined, in the exemplary embodiment shown in FIG. 8, the video inspection device 100 can conduct a measurement (e.g., depth) of the anomaly 504 by determining the distance between the fourth measurement point 524 selected to be at the deepest point of the anomaly 504 and the reference surface 550. The accuracy of this depth measurement is determined by the accuracy in selecting the plurality of measurement points 521, 522, 523, 524 on the object surface 510 of the viewed object 502. In many instances as discussed previously, the contour of the anomaly 504 in the image 500 is difficult to assess from the two-dimensional image and may be too small or otherwise insufficient to reliably locate the plurality of measurement points 521, 522, 523, 524. Accordingly, in many cases, an operator will want further detail in the area of the anomaly 504 to evaluate the accuracy of the location of these measurement points 521, 522, 523, 524. So while some video inspection devices 100 can provide a point cloud view of the full image 500, that view may not provide the required level of detail of the anomaly 504 as discussed previously. In order to provide a more meaningful view of the object surface 510 in the area around the measurement points 521, 522, 523, 524 than offered by a point cloud view of the three-dimensional data of the entire image 500, the inventive method creates a subset of the three-dimensional data in the region of interest.

At step 650, the CPU 150 of the video inspection device 100 can establish a second coordinate system different from the first coordinate system. In one embodiment, the second coordinate system can be based on the reference surface 550 and the plurality of measurement points 521, 522, 523, and 524. The video inspection device 100 can assign the origin of the second coordinate system ($x_{O2}$, $y_{O2}$, $z_{O2}$)=(0, 0, 0) to be located proximate the average position 525 of the three-dimensional coordinates of points on the reference surface 550 corresponding to two or more of the plurality of measurement points 521, 522, 523, 524 on the object surface 510 (e.g., by projecting the measurement points 521, 522, 523, and 524 onto the reference surface 550 and determining an average position 525 on the reference surface 550). In some cases, the three-dimensional coordinates of the points on the reference surface 550 corresponding to the measurement points 521, 522, 523 can be the same. However, in some circumstances, due to noise and/or small variations in the object surface 510, the measurement points 521, 522, 523 do not fall exactly on the reference surface 550, and therefore have different coordinates.

When determining points on the reference surface 550 that correspond to measurement points 521, 522, 523, 524 on the object surface 510, it is convenient to apply the concept of line directions, which convey the relative slopes of lines in the x, y, and z planes, and can be used to establish perpendicular or parallel lines. For a given line passing through two three-dimensional coordinates (x1, y1, z1) and (x2,y2,z2), the line directions (dx, dy, dz) may be defined as:

$$dx = x2 - x1 \quad (3)$$

$$dy = y2 - y1 \quad (4)$$

$$dz = z2 - z1 \quad (5)$$

Given a point on a line (x1, y1, z1) and the line's directions (dx, dy, dz), the line can be defined by:

$$\frac{(x - x1)}{dx} = \frac{(y - y1)}{dy} = \frac{(z - z1)}{dz} \quad (6)$$

Thus, given any one of an x, y, or z coordinate, the remaining two can be computed. Parallel lines have the same or linearly scaled line directions. Two lines having directions (dx1, dy1, dz1) and (dx2, dy2, dz2) are perpendicular if:

$$dx1 \cdot dx2 + dy1 \cdot dy2 + dz1 \cdot dz2 = 0 \quad (7)$$

The directions for all lines normal to a reference plane defined using equation (2) are given by:

$$dx_{RSN} = -k_{1RS} \quad (8)$$

$$dy_{RSN} = -k_{2RS} \quad (9)$$

$$dz_{RSN} = 1 \quad (10)$$

Based on equations (6) and (8) through (10), a line that is perpendicular to the reference surface 550 and passing through a surface point $(x_s, y_s, z_s)$ can be defined as:

$$\frac{x - x_S}{-k_{1RS}} = \frac{y - y_S}{-k_{2RS}} = z - z_S \quad (11)$$

In one embodiment, the coordinates of a point on the reference surface 550 $(x_{iRS1}, y_{iRS1}, z_{iRS1})$ corresponding to a point on the object surface 510 $(x_{iS1}, y_{iS1}, z_{iS1})$ (e.g. three-dimensional coordinates in a first coordinate system of points on the reference surface 550 corresponding to the measurement points 521, 522, 523, 524), can be determined by defining a line normal to the reference surface 550 having directions given in equations (8)-(10) and passing through $(x_{iS1}, y_{iS1}, z_{iS1})$, and determining the coordinates of the intersection of that line with the reference surface 550. Thus, from equations (2) and (11):

$$z_{iRS} = \frac{(k_{1RS}^2 \cdot z_{iS1} + k_{1RS} \cdot x_{iS1} + k_{2RS}^2 \cdot z_{iS1} + k_{2RS} \cdot y_{iS1} + k_{ORS})}{(1 + k_{1RS}^2 + k_{2RS}^2)} \quad (12)$$

$$x_{iRS1} = k_{1RS1} \cdot (z_{iS1} - z_{iRS1}) + x_{iS1} \quad (13)$$

$$y_{iRS1} = k_{2RS} \cdot (z_{iS1} - z_{iRS1}) + y_{iS1} \quad (14)$$

In one embodiment, these steps (equations (3) through (14)) can be used to determine the three-dimensional coordinates of points on the reference surface 550 corresponding to the measurement points 521, 522, 523, 524. Then the average position 525 of these projected points of the measurement points on the reference surface 550 $(x_{M1avg}, y_{m1avg}, z_{M1avg})$ can be determined. The origin of the second coordinate system $(x_{O2}, y_{O2}, z_{O2}) = (0, 0, 0)$ can then be assigned and located proximate the average position 525 $(x_{M1avg}, y_{M1avg}, z_{M1avg})$.

Locating the origin of the second coordinate system proximate the average position 525 in the area of the anomaly 504 with the z values being the perpendicular distance from each surface point to the reference surface 550 allows a point cloud view rotation to be about the center of the area of the anomaly 504 and permits any depth map color scale to indicate the height or depth of a surface point from the reference surface 550.

In order to take advantage of this second coordinate system, at step 660, the CPU 150 of the video inspection device 100 transforms the three-dimensional coordinates in the first coordinate system $(x_{i1}, y_{i1}, z_{i1})$ determined for various points (e.g., the plurality of surface points, the plurality of measurement points 521, 522, 523, 524, the points on the reference surface 550 including the frame points 560, etc.) to three-dimensional coordinates in the second coordinate system $(x_{i2}, y_{i2}, z_{i2})$.

In one embodiment, a coordinate transformation matrix ([T]) can be used to transform the coordinates according to the following:

$$([x_{i1}\, y_{i1}\, z_{i1}] - [x_{M1avg}\, y_{M1avg}\, z_{M1avg}]) * [T] = [x_{i2}\, y_{i2}\, z_{i2}] \quad (15)$$

where [T] is a transformation matrix.

In non-matrix form, the three-dimensional coordinates in the second coordinate system can be determined by the following:

$$x_{i2} = (x_{i1} - x_{M1avg}) * T_{00} + (y_{i1} - y_{M1avg}) * T_{10} + (z_{i1} - z_{M1avg}) * T_{20} \quad (16)$$

$$y_{i2} = (x_{i1} - x_{M1avg}) * T_{01} + (y_{i1} - y_{M1avg}) * T_{11} + (z_{i1} - z_{M1avg}) * T_{21} \quad (17)$$

$$z_{i2} = (x_{i1} - x_{M1avg}) * T_{02} + (y_{i1} - y_{M1avg}) * T_{120} + (z_{i1} - z_{M1avg}) * T_{22} \quad (18)$$

where the transformation matrix values are the line direction values of the new x, y, and z axes in the first coordinate system.

At step 670, the CPU 150 of the video inspection device 100 determines a subset of the plurality of surface points that are within a region of interest on the object surface 510 of the viewed object 502. In one embodiment, the region of interest can be a limited area on the object surface 510 of the viewed object 502 surrounding the plurality of selected measurement points 521, 522, 523, 524 to minimize the amount of three-dimensional data to be used in a point cloud view. It will be understood that the step of determining of the subset 660 can take place before or after the transformation step 660. For example, if the determination of the subset at step 670 takes place after the transformation step 660, the video inspection device 100 may transform the coordinates for all surface points, including points that are outside the region of interest, before determining which of those points are in the region of interest. Alternatively, if the determination of the subset at step 670 takes place before the transformation step 660, the video inspection device 100 may only need to transform the coordinates for those surface points that are within the region of interest.

In one embodiment, the region of interest can be defined by determining the maximum distance ($d_{MAX}$) between each of the points on the reference surface 550 corresponding to the measurement points 521, 522, 523, 524 and the average position 525 of those points on the reference surface 550 (the origin of the second coordinate system $(x_{O2}, y_{O2}, z_{O2}) = (0, 0, 0)$ if done after the transformation, or $(x_{M1avg}, y_{M1avg}, z_{M1avg})$ in the first coordinate system if done before the transformation). In one embodiment, the region of interest can include all surface points that have corresponding points on the reference surface 550 (i.e., when projected onto the reference surface) that are within a certain threshold distance ($d_{ROI}$) of the average position 525 of the measurement points 521, 522, 523, 524 on the reference surface 550 (e.g., less than the maximum distance ($d_{ROI}=d_{MAX}$) or less than a distance slightly greater (e.g. twenty percent greater) than the maximum distance ($d_{ROI}=1.2*d_{MAX}$)). For example, if the average position 525 in the second coordinate system is at ($x_{O2}$, $y_{O2}$, $Z_{O2}$)=(0, 0, 0), the distance (d) from that position to a point on the reference surface 550 corresponding to a surface point ($x_{iRS2}$, $y_{iRS2}$, $z_{iRS2}$) is given by:

$$d_{iRS2} = \sqrt{(x_{iRS2}-x_{O2})^2 + (y_{iRS2}-y_{O2})^2} \quad (19)$$

Similarly, if the average position 525 in the first coordinate system is at ($x_{M1avg}$, $y_{M1avg}$, $z_{M1avg}$), the distance (d) from that position to a point on the reference surface 550 corresponding to a surface point ($x_{iRS1}$, $Y_{iRS1}$, $z_{iRS1}$) is given by:

$$d_{iRS1} = \sqrt{(x_{iRS1}-x_{M1avg})^2 + (y_{iRS1}-y_{M1avg})^2} \quad (20)$$

If a surface point has a distance value ($d_{iRS1}$ or $d_{iRS2}$) less than the region of interest threshold distance ($d_{ROI}$) and therefore in the region of interest, the video inspection device 100 can write the three-dimensional coordinates of that surface point and the pixel color corresponding to the depth of that surface point to a point cloud view file. In this exemplary embodiment, the region of interest is in the form of a cylinder that includes surface points falling within the radius of the cylinder. It will be understood that other shapes and methods for determining the region of interest can be used.

The region of interest can also be defined based upon the depth of the anomaly 504 on the object surface 510 of the viewed object 502 determined by the video inspection device 100 in the first coordinate system. For example, if the depth of the anomaly 504 was measured to be 0.005 inches (0.127 mm), the region of interest can be defined to include only those points having distances from the reference surface 550 (or z dimensions) within a certain range (±0.015 inches (0.381 mm)) based on the distance of one or more of the measurement points 521, 522, 523, 524 to the reference surface 550. If a surface point has a depth value inside the region of interest, the video inspection device 100 can write the three-dimensional coordinates of that surface point and the pixel color corresponding to the depth of that surface point to a point cloud view file. If a surface point has a depth value outside of the region of interest, the video inspection device 100 may not include that surface point in a point cloud view file.

Figure 10:
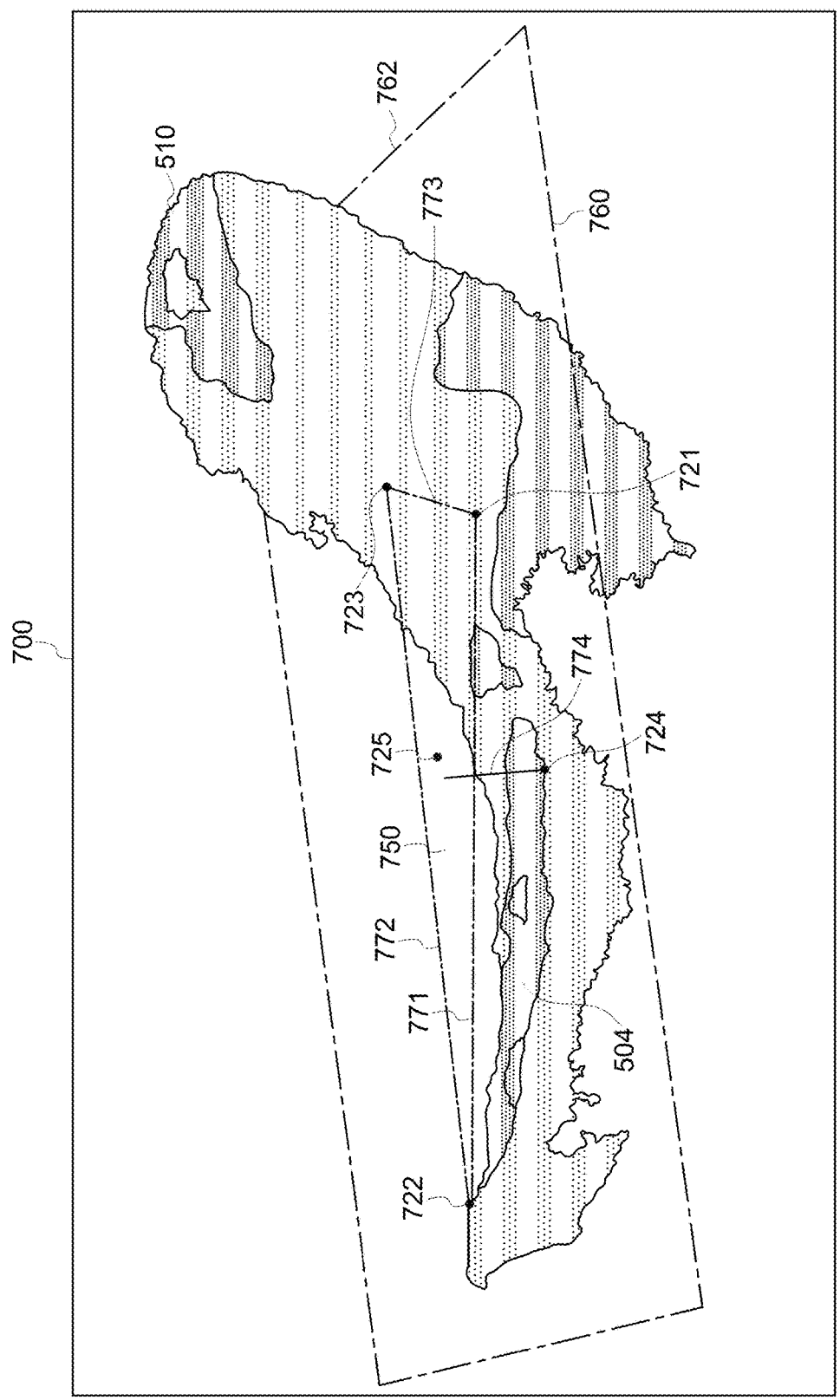
FIG. 10 is a display of a subset of a plurality of surface points in a point cloud view.

At step 680, and as shown in FIG. 10, the monitor 170, 172 of the video inspection device 100 can display a rendered three-dimensional view (e.g., a point cloud view) 700 of the subset of the plurality of surface points in the three-dimensional coordinates of the second coordinate system, having an origin 725 at the center of the view. In one embodiment (not shown), the display of the point cloud view 700 can include a color map to indicate the distance between each of the surface points and the reference surface 750 in the second coordinate system (e.g., a first point at a certain depth is shown in a shade of red corresponding that depth, a second point at a different depth is shown in a shade of green corresponding to that depth). The displayed point cloud view 700 can also include the location of the plurality of measurement points 721, 722, 723, 724. To assist the operator in viewing the point cloud view 700, the video inspection device 100 can also determine three-dimensional line points 771, 772, 773 along straight lines between two or more of the plurality of measurement points 721, 722, 723 in the three-dimensional coordinates of the second coordinate system, and display those line points 771, 772, 773 in the point cloud view 700. The point cloud view 700 can also include a depth line 774 from the measurement point 724 intended to be located at the deepest point of the anomaly 504 to the reference surface 750. In one embodiment, the video inspection device 100 can determine if the depth line 774 exceeds a tolerance specification or other threshold and provide a visual or audible indication or alarm of such an occurrence.

The displayed point cloud view 700 can also include a plurality of frame points 760 forming a frame 762 on the reference surface 750 in the second coordinate system to indicate the location of the reference surface 750. In another embodiment, the displayed point cloud view 700 can also include a scale indicating the perpendicular distance from the reference surface 750.

As shown in FIG. 10, by limiting the data in the point cloud view 700 to those points in the region of interest and allowing the view to be rotated about a point 725 in the center of the region of interest (e.g., at the origin), the operator can more easily analyze the anomaly 504 and determine if the depth measurement and placement of the measurement points 721, 722, 723, 724 was accurate. In one embodiment, the operator can alter the location of one or more of the measurement points 721, 722, 723, 724 in the point cloud view 700 if correction is required. Alternatively, if correction is required, the operator can return to the two-dimensional image 500 of FIG. 8 and reselect one or more of the measurement points 521, 522, 523, 524, and repeat the process.

In another embodiment, the monitor 170, 172 of the video inspection device 100 can display a rendered three-dimensional view 700 of the subset of the plurality of surface points in the three-dimensional coordinates of the first coordinate system without ever conducting a transformation of coordinates. In this embodiment, the point cloud view 700 based on the original coordinates can also include the various features described above to assist the operator, including displaying a color map, the location of the plurality of measurement points, three-dimensional line points, depth lines, frames, or scales.

Figure 11:
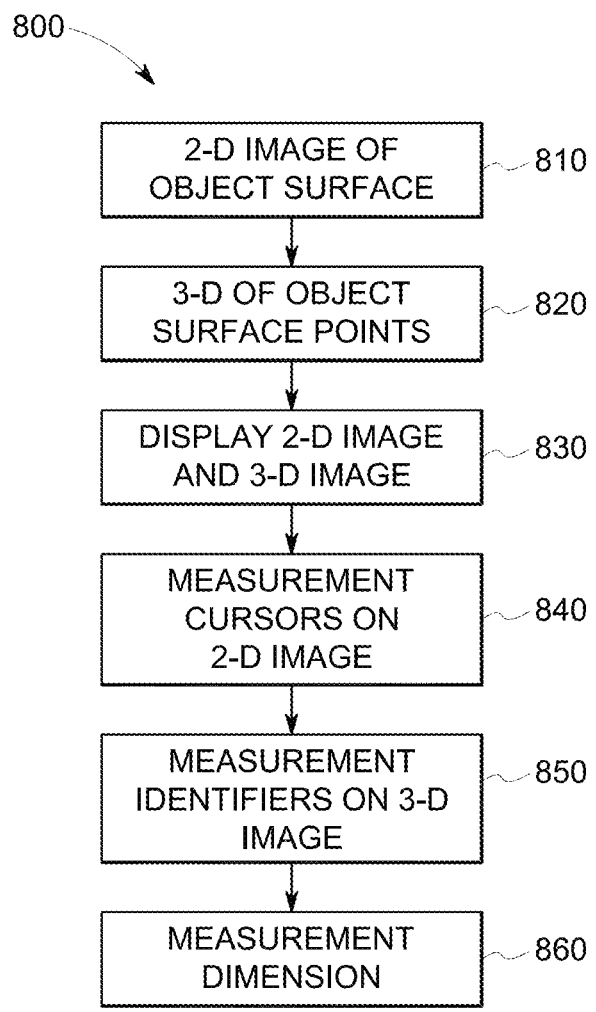
FIG. 11 is a flow diagram of an exemplary method for displaying a two-dimensional image of viewed object simultaneously with an image depicting the three-dimensional geometry of the viewed object in another exemplary embodiment.

FIG. 11 is a flow diagram of an exemplary method 800 for displaying a two-dimensional image of viewed object simultaneously with an image depicting the three-dimensional geometry of the viewed object in another exemplary embodiment. It will be understood that the steps described in the flow diagram of FIG. 11 can be performed in a different order than shown in the flow diagram and that not all of the steps are required for certain embodiments.

Figure 12:
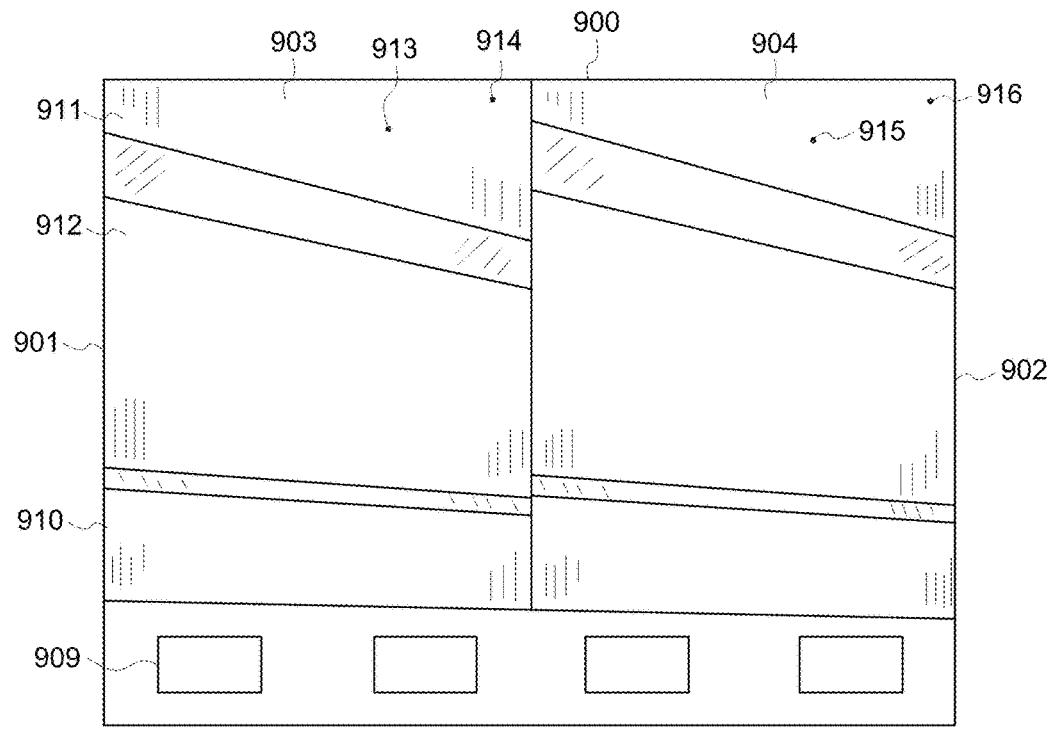
FIG. 12 is a display of a two-dimensional image and a stereo image of the viewed object.

At step 810 of the exemplary method (FIG. 8), and as shown in FIG. 12, the video inspection device 100 (e.g., the imager 124 of FIG. 1) obtains at least one two-dimensional image 903 of the object surface 911 of a viewed object 910 having an anomaly 912 and displays it on a first side 901 of the display 900 (e.g., an integral display 170, external monitor 172, or touch screen of a user interface). In one embodiment, the two-dimensional image 903 is displayed in a measurement mode of the video inspection device 100.

At step 820 of the exemplary method 800 (FIG. 11), and as shown in FIG. 12, the video inspection device 100 (e.g., the CPU 150 of FIG. 1) determines the three-dimensional coordinates (e.g., (x, y, z)) of a plurality of surface points 913, 914 on the object surface 911 of the viewed object 910. In one embodiment, the video inspection device generates three-dimensional data from the two-dimensional image 903 in order to determine the three-dimensional coordinates.

FIG. 12 is a display 900 of a two-dimensional first stereo image 903 of the viewed object 910 on the first side 901 of the display 900, and a corresponding two-dimensional second stereo image 904 of the viewed object 910 on the second side 902 of the display 900. In one embodiment, the video inspection device 100 (e.g., the CPU 150) employs stereo techniques to determine the three-dimensional coordinates (e.g., (x, y, z)) of a plurality of surface points 913, 914 on the two-dimensional first stereo image 903 by finding matching surface points 915, 916 on the corresponding two-dimensional second stereo image 904 and then computing the three-dimensional coordinates based on the pixel distance disparity between the plurality of surface points 913, 914 on the two-dimensional first stereo image 903 (or an area of pixels (e.g., 4×4 area)) and the matching surface points 915, 916 on the corresponding two-dimensional second stereo image 904. It will be understood and as shown in FIGS. 12-14, the reference herein to a two-dimensional image with respect to stereo image 903, 904 can include both or either of the first (left) stereo image 903 and the second (right) stereo image 904.

Several different existing techniques can be used to provide the three-dimensional coordinates of the surface points 913, 914 in the two-dimensional image 903 (FIG. 12) of the object surface 911 (e.g., stereo, scanning systems, stereo triangulation, structured light methods such as phase shift analysis, phase shift moire, laser dot projection, etc.). Most such techniques comprise the use of calibration data, which, among other things, includes optical characteristic data that is used to reduce errors in the three-dimensional coordinates that would otherwise be induced by optical distortions. With some techniques, the three-dimensional coordinates may be determined using one or more two-dimensional images captured in close time proximity that may include projected patterns and the like. It is to be understood that references to three-dimensional coordinates determined using two-dimensional image 903 may also comprise three-dimensional coordinates determined using one or a plurality of two-dimensional images of the object surface 911 captured in close time proximity, and that the two-dimensional image 903 displayed to the operator during the described operations may or may not actually be used in the determination of the three-dimensional coordinates.

Figure 13:
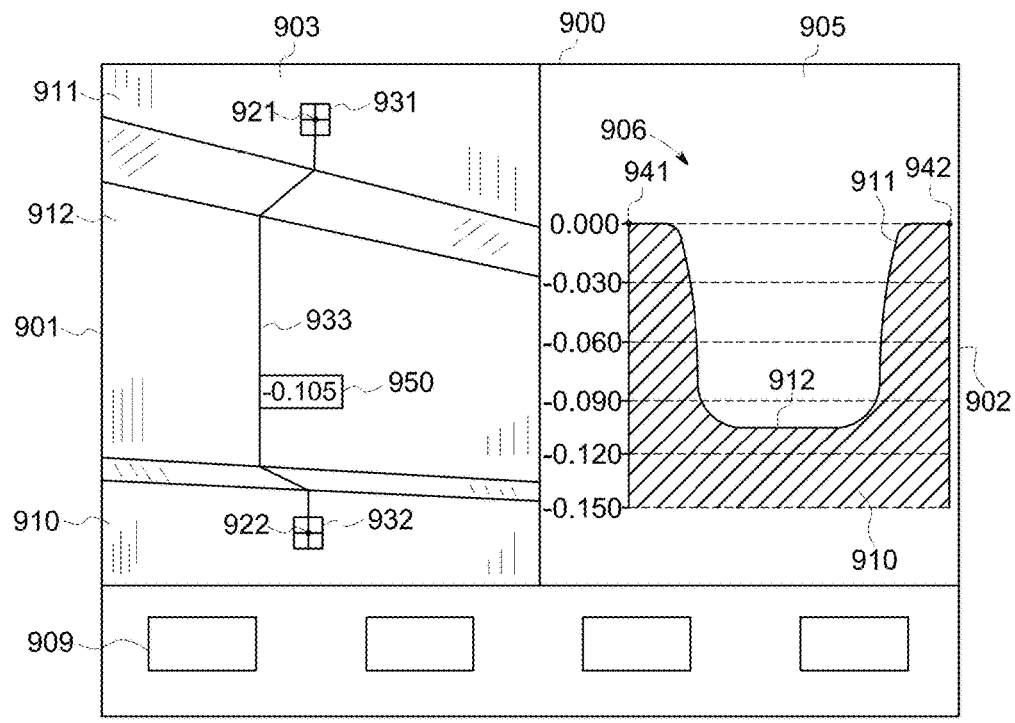
FIG. 13 is a display of a two-dimensional image of the viewed object with measurement cursors and a rendered image of the three-dimensional geometry of the viewed object in the form of a depth profile image with measurement identifiers.
Figure 14:
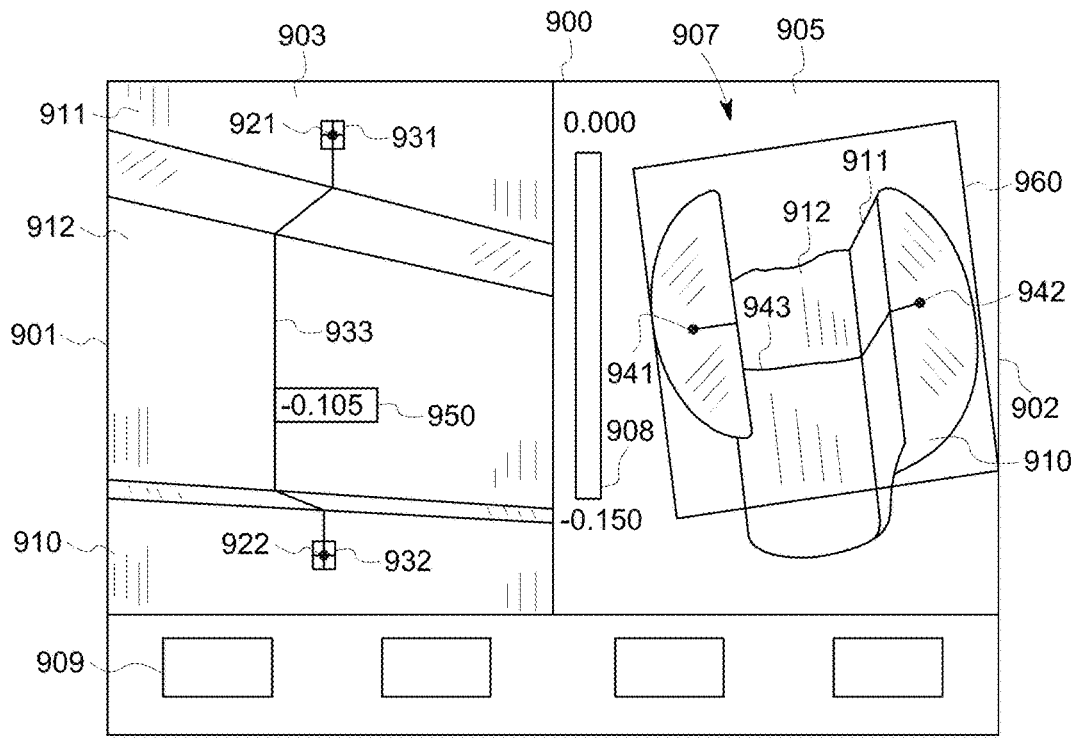
FIG. 14 is a display of a two-dimensional image of the viewed object with measurement cursors and a rendered image of the three-dimensional geometry of the viewed object in the form of a point cloud view with measurement identifiers.

At step 830 of the exemplary method 800 (FIG. 11), and as shown in FIGS. 13 and 14, at least a portion of the two-dimensional image 903 of the viewed object 910 with measurement cursors 931, 932 is displayed on a first side 901 of the display 900 and a rendered image 905 of the three-dimensional geometry of at least a portion of the object surface 911 of the viewed object 910 is displayed on the second side 902 of the display 900. As compared to FIG. 12, the rendered image 905 replaces the second (right) stereo image 904 in the display 900. In one embodiment, the video inspection device 100 (e.g., the CPU 150) begins (and, in one embodiment, completes) the process of determining the three-dimensional coordinates (e.g., (x, y, z)) of the plurality of surface points 913, 914 on the object surface 911 of the viewed object 910 before the placement and display of the measurement cursors 931, 932. Although the exemplary embodiments shown in FIGS. 13 and 14 show a single rendered image 905 of the three-dimensional geometry of the object surface 911 of the viewed object 910 displayed on the second side 902 of the display 900, it will be understood that more than one rendered image 905 can be shown simultaneously with or without the two-dimensional image 903.

In an exemplary embodiment shown in FIG. 13, the rendered image 905 is a depth profile image 906 showing the three-dimensional geometry of the object surface 911 of the viewed object 910, including the anomaly 912. In another exemplary embodiment shown in FIG. 14, the rendered image 905 is a point cloud view 907 showing the three-dimensional geometry of the object surface 911 of the viewed object 910, including the anomaly 912. In the exemplary point cloud view 907 shown in FIG. 14, only a subset of the three-dimensional coordinates of the surface points 913, 914 on the object surface 911 of the viewed object 910 are displayed in a region of interest based on the location of the measurement cursors 931, 932. In another embodiment, the point cloud view 907 displays all of the computed three-dimensional coordinates of the surface points 913, 914 on the object surface 911 of the viewed object 910. In one embodiment, e.g., when the display is a user-interface touch screen, the user can rotate the point cloud view 907 using the touch screen.

In one embodiment and as shown in FIG. 14, the point cloud view 907 may be colorized to indicate the distance between the surface points of the object surface 911 of the viewed object 910 and a reference surface 960 (e.g., reference plane determined using three-dimensional coordinates proximate to one or more of the plurality of measurement cursors 931, 932). For example, a first point at a certain depth is shown in a shade of red corresponding that depth, a second point at a different depth is shown in a shade of green corresponding to that depth. A color depth scale 908 is provided to show the relationship between the colors shown on the point cloud view 907 and their respective distances from the reference surface 960. In one embodiment, the point could view 907 may be surfaced to graphically smooth the transition between adjacent points in the point cloud view 907.

Once the three-dimensional coordinates have been determined for a plurality of surface points 913, 914 on the object surface 911 of the viewed object 910, the user can conduct measurements on the two-dimensional image 903.

In one embodiment, the video inspection device 100 saves as an image the split view of the two-dimensional image 903 and the rendered image 905. The video inspection device 100 can also save as metadata the original, full stereo image of the first (left) stereo image 903 and the second (right) stereo image 904 (e.g., grayscale only) as shown in FIG. 11 and the calibration data to allow re-computation of the three-dimensional data and re-measurement from the saved file. Alternatively, the video inspection device 100 can save the computed three-dimensional coordinates and/or disparity data as metadata, which reduces the processing time upon recall but results in a larger file size.

At step 840 of the exemplary method 800 (FIG. 11), and as shown in FIGS. 13 and 14, measurement cursors 931, 932 are placed (using a pointing device) and displayed on the two-dimensional image 903 to allow the video inspection device 100 (e.g., the CPU 150) to determine the dimensions of the anomaly 912 (e.g., height or depth, length, width, area, volume, point to line, profile slice, etc.). In another embodiment where the two-dimensional image is not a stereo image, measurement cursors 931, 932 (as shown in FIGS. 13 and 14) can also be placed on the two-dimensional image 903 to allow the video inspection device 100 (e.g., the CPU 150) to determine the dimensions of the anomaly 912 (e.g., height or depth, length, width, area, volume, point to line, profile slice, etc.). In yet another embodiment, instead of being placed on the two-dimensional image 903, measurement cursors can be placed (using a pointing device) on the rendered image 905 of the three-dimensional geometry of at least a portion of the object surface 911 of the viewed object 910 on the second side 902 of the display 900.

In the exemplary display 900, the first measurement cursor 931 is placed on the first measurement point 921 on the object surface 911 of the viewed object 910 and the second measurement cursor 932 is placed on the second measurement point 922 on the object surface 911 of the viewed object 910. Since the three-dimensional coordinates of the measurement points 921, 922 on the object surface 911 of the viewed object 910 are known, a geometric measurement (e.g., depth or length measurement) of the object surface 911 can be performed by the user and the video inspection device 100 (e.g., the CPU 150) can determine the measurement dimension 950 as shown in FIGS. 13 and 14. In the example shown in FIGS. 13 and 14, a measurement line 933 is displayed on the two-dimensional image 903.

The rendered image 905 of the three-dimensional geometry of the object surface 911 of the viewed object 910 is displayed on the second side 902 of the display 900 in order to assist in the placement of the measurement cursors 931, 932 on the two-dimensional image 903 to conduct the geometric measurement. In a conventional system involving stereo or non-stereo two-dimensional images, these measurement cursors 931, 932 (as shown in FIGS. 13 and 14) are placed based solely on the view provided by the two-dimensional image 903, which may not allow for accurate placement of the measurement cursors 931, 932 and accurate measurements.

At step 850 of the exemplary method 800 (FIG. 11), and as shown in FIGS. 13 and 14, measurement identifiers 941, 942 corresponding to the measurement cursors 931, 932 placed on the two-dimensional image 903 are displayed on the rendered image 905 of the three-dimensional geometry of the object surface 911 of the viewed object 912. For example, the first measurement identifier 941 is shown on the rendered image 905 at the same three-dimensional coordinate of the object surface 911 of the viewed object 912 as the first measurement cursor 931, and the second measurement identifier 942 is shown on the rendered image 905 at the same three-dimensional coordinate of the object surface 911 of the viewed object 912 as the second measurement cursor 932. In the exemplary point cloud view 907 shown in FIG. 14, a measurement line identifier 943 corresponding to the measurement line 933 (e.g., depth measurement line) in the two-dimensional image 901 is displayed. This rendered image 905 of the three-dimensional geometry of the object surface 911 of the viewed object 910 simultaneously displayed with the two-dimensional image 903 of the object surface 911 of the viewed object 912 allows the user to more accurately place the measurement cursors 931, 932 to provide a more accurate geometric measurement. In yet another embodiment, where the measurement cursors are placed (using a pointing device) on the rendered image 905, measurement identifiers corresponding to the measurement cursors are displayed on the two-dimensional image 903.

In one embodiment, as the user changes the location of the measurement cursors 931, 932 in the two-dimensional image 903, the video inspection device 100 (e.g., the CPU 150) automatically updates the location of the measurement identifiers 941, 942 corresponding to the measurement cursors 931, 932 and the rendered image 905 (e.g., region of interest or depth colors of the point cloud view 907 in FIG. 14) of the three-dimensional geometry of the object surface 911 of the viewed object 912 also changes to allow the user to visualize the new measurement virtually in real time. In another embodiment, after the measurement cursors 931, 932 are placed in the two-dimensional image 903, the measurement identifiers 941, 942 can be repositioned in the rendered image 905.

In yet another embodiment, where the measurement cursors are placed (using a pointing device) on the rendered image 905 and measurement identifiers corresponding to the measurement cursors are displayed on the two-dimensional image 903, as the user changes the location of the measurement cursors in the rendered image 905, the video inspection device 100 (e.g., the CPU 150) automatically updates the location of the measurement identifiers corresponding to the measurement cursors and the two-dimensional image also changes to allow the user to visualize the new measurement virtually in real time. In another embodiment, after the measurement cursors are placed on the rendered image 905, the measurement identifiers can be repositioned in the two-dimensional image 903.

At step 860 of the exemplary method 800 (FIG. 11), and as shown in FIGS. 13 and 14, the video inspection device 100 (e.g., the CPU 150) determines the measurement dimension 950 sought by the user for the particular geometric measurement (e.g., depth or length measurement) based on the locations of the measurement cursors 931, 932 and displays that measurement dimension 950 on the display 900. In another embodiment, the measurement dimension can displayed on the display 900 on the rendered image 905.

As shown in FIGS. 12-14, soft keys 909 can be provided on the display 900 to provide various functions to the user in obtaining images and taking measurements (e.g., views, undo, add measurement, next measurement, options, delete, annotation, take image, reset, zoom, full image/measurement image, depth map on/off, etc.). In one embodiment, when a user activates either the two-dimensional image 903 or the rendered image 905, the particular soft keys 909 displayed can change based on the active image.

Figure 15A:
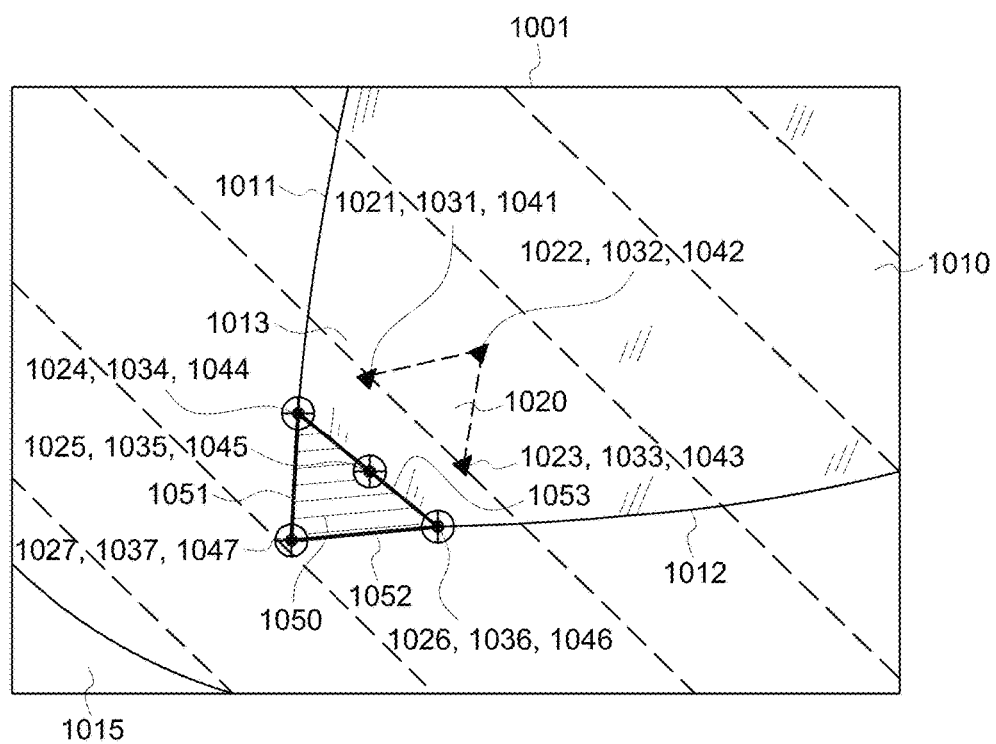
FIG. 15A is another exemplary image obtained by the video inspection device of a turbine blade having a missing corner in another exemplary embodiment.

FIG. 15A is another exemplary image 1001 obtained by the video inspection device 100 of a turbine blade 1010 having a missing corner (shown by polygon 1050) and a shroud 1015 in another exemplary embodiment. In one embodiment, the image 1001 used can be a two-dimensional image 1001 of the surface 1013 of the viewed object (turbine blade 1010). In a further example, the two-dimensional image can be a stereo image. As shown in FIG. 15A, the user can use the video inspection device 100 (e.g., the imager 124) to obtain at least one image 1001 of the surface 1013 of the turbine blade 1010 and display it on a video monitor (e.g., an integral display 170 or external monitor 172). In one embodiment, the image 1001 can be displayed in a measurement mode of the video inspection device 100.

The video inspection device 100 (e.g., the CPU 150) can determine the three-dimensional coordinates (e.g., (x, y, z)) of a plurality of surface points on the object surface 1013 of the viewed object 1010. In one embodiment, the video inspection device can generate three-dimensional data from the image 1001 in order to determine the three-dimensional coordinates. The three-dimensional coordinates of the surface points on the object surface 1013 of the viewed object 1010 can be associated with the pixels of the displayed two-dimensional image 1001. Several different existing techniques can be used to provide the three-dimensional coordinates of the surface points in the image 1001 (FIG. 15A) of the object surface 1013 (e.g., stereo, scanning systems, stereo triangulation, structured light methods such as phase shift analysis, phase shift moire, laser dot projection, etc.). In one embodiment, the video inspection device 100 captures the two-dimensional image 1001 using a diffuse inspection light source with no structured light pattern and the three-dimensional surface coordinates are computed using one or more images captured with a structured light pattern projected onto the object. In such a case, the structured light pattern may be projected with the diffuse inspection light source disabled.

Once again, most such techniques comprise the use of calibration data, which, among other things, includes optical characteristic data that is used to reduce errors in the three-dimensional coordinates that would otherwise be induced by optical distortions. With some techniques, the three-dimensional coordinates may be determined using one or more images captured in close time proximity that may include projected patterns and the like. In one embodiment, video inspection device 100 (e.g., the CPU 150) may use calibration data to compute the object surface point coordinates. In one example, calibration data may be specific to the video inspection device 100 is used, and may include sensor and optics information needed to determine actual dimensions and distances. In another example, calibration data may include ray equations to correlate each pixel of the sensor with a specific point on the viewed object.

It is to be understood that references to three-dimensional coordinates determined using image 1001 may also comprise three-dimensional coordinates determined using one or a plurality of images 1001 of the object surface 1013 captured in close time proximity, and that the image 1001 displayed to the user during the described operations may or may not actually be used in the determination of the three-dimensional coordinates. In one embodiment, the video inspection device 100 (e.g., the CPU 150) may average together multiple captured images in order to generate a composite image with enhanced detail or reduced noise as compared with a single image.

As shown in FIG. 15A, the video inspection device 100 (e.g., the CPU 150) can determine a three-dimensional reference surface 1020 (e.g., measurement plane shown by dashed lines extending across the image). In some embodiments, the reference surface 1020 can be flat, while in other embodiments the reference surface 1020 can be curved. Similarly, in one embodiment, the reference surface 1020 can be in the form of a plane, while in other embodiments, the reference surface 1020 can be in the form of a different shape (e.g., cylinder, sphere, etc.). For example, a user can use the joystick 180 (or other pointing device (e.g., mouse, touch screen)) of the video inspection device 100 to select one or more reference surface points 1021, 1022, 1023 on the image 1001 of the object surface 1013 of the viewed object 1010 (turbine blade).

In one embodiment and as shown in FIG. 15A, a total of three reference surface points 1021, 1022, 1023 are selected on the image 1001 of the object surface 1013 of the viewed object 1010. In one embodiment, the plurality of reference surface points 1021, 1022, 1023 on the object surface 1013 of the viewed object 1010 can be selected by placing reference surface cursors 1031, 1032, 1033 (or other pointing devices) on reference surface pixels 1041, 1042, 1043 of the image 1001 corresponding to the plurality of reference surface points 1021, 1022, 1023 on the object surface 1013.

The video inspection device 100 (e.g., the CPU 150) can determine the three-dimensional coordinates of each of the plurality of reference surface points 1021, 1022, 1023.

As shown in FIG. 15A, the CPU 150 of the video inspection device 100 can determine a reference surface 1020. In the exemplary area measurement shown in FIG. 15A, the three-dimensional coordinates of the three reference surface points 1021, 1022, 1023 or three or more surface points proximate one or more of the three reference surface points 1021, 1022, 1023 can be used to determine a reference surface 1020 (e.g., a plane). As discussed above, in one embodiment, the video inspection device 100 can perform a curve fitting of the three-dimensional coordinates of the three reference surface points 1021, 1022, 1023 to determine an equation for the reference surface 1020 (e.g., for a plane extending indefinitely in all directions). In one embodiment, the video inspection device 100 (e.g., the CPU 150) can perform a curve fitting of the three-dimensional coordinates of the surface points associated with the pixels in the vicinity of reference surface cursors 1031, 1032, 1033 to determine an equation for the reference surface 1020 (e.g., for a plane) as described in equation (1) above. In another embodiment, the curve fitting may use only the three-dimensional coordinates of the surface points associated with the pixels in the vicinity of only one of the reference surface cursors 1031, 1032, 1033 for the reference surface 1020. In another embodiment, the three-dimensional coordinates of a single selected reference surface point can be used by the video inspection device 100 (e.g., the CPU 150) to establish the reference surface to be a plane at z=10 mm (the z axis being along the central optical axis of the borescope view). In another example, a single cursor may be used to define a reference surface, for example, by establishing a plane orthogonal or parallel to the surface or the principal axis of the viewing optical system and passing through the three-dimensional surface coordinate associated with the cursor location. In a further example, four or more selected coordinates can establish various curved reference surfaces, such as spherical, cylindrical, or other surface shapes, as the reference surface. In further examples, numerous cursors may be used to fit curved surfaces, such as spheres, cylinders, etc. In another embodiment, one or more cursors may be used to select regions of pixels, i.e. the region within a circular cursor, and the reference surface may be determined by fitting a plane or other surface to the three-dimensional surface coordinates associated with the selected region or regions.

As shown in FIG. 15A, the turbine blade 1010 has a missing corner (shown by polygon 1050). The present disclosure provides methods and devices for measuring features on or near an object, including features that may have portions that are missing or spaced apart from the object. For instance, a turbine blade 1010 may be inspected to determine if the tip or corner of the blade 1010 has broken off In such a case, the relevant feature to be measured, e.g., dimensions of the missing corner, is not on the surface 1013 of the turbine blade 1010 itself, and instead extends into space beyond the surface 1013 of the turbine blade 1010. Therefore, a measurement using only the three-dimensional coordinates of the points on the surface 1013 of the turbine blade 1010 would not provide the desired information (missing area, lengths of the missing edges, etc.). As will be explained, once the reference surface 1020 is established, the user may perform a measurement of a geometric dimension, such as a length, point to line, area, or multi-length measurement, by positioning measurement cursors 1034, 1035, 1036, 1037 on the image 1001 even in areas that are not on the surface of the viewed object 1010 that do not have surface points on the surface 1013 of the turbine blade 1010 associated with them.

In one embodiment and as shown in FIG. 15A, a total of four measurement cursors 1034, 1035, 1036, 1037 are positioned on measurement cursor pixels 1044, 1045, 1046, 1047 of the image 1001. As will be explained, through calibration, the three-dimensional trajectory associated with each two-dimensional measurement cursor pixel 1044, 1045, 1046, 1047 of the image 1001 is known and used to calculate where the trajectory line from each measurement cursor pixel 1044, 1045, 1046, 1047 of the image 1001 is positioned (e.g., which can be a fractional pixel position in which interpolation would be used) intersects with the reference surface 1020 in three-dimensional space to determine the projected reference surface points 1024, 1025, 1026, 1027 associated with those measurement cursor pixels 1044, 1045, 1046, 1047 on the reference surface 1020. As can be seen in FIG. 15A, once the projected reference surface points 1024, 1025, 1026, 1027 on the reference surface 1020 are known, the user may perform a measurement, such as a length, point to line, area, or multi-length measurement, based on the three-dimensional coordinates of the projected reference surface points 1024, 1025, 1026, 1027 on the reference surface 1020. For example, as shown in FIG. 15A, the user can perform an area measurement forming a polygon 1050 having a first side 1051 (which provides the length of missing portion of the first edge 1011 of the blade), a second side 1052 (which provides the length of missing portion of the second edge 1012 of the blade), and a third side 1053.

Figure 15B:
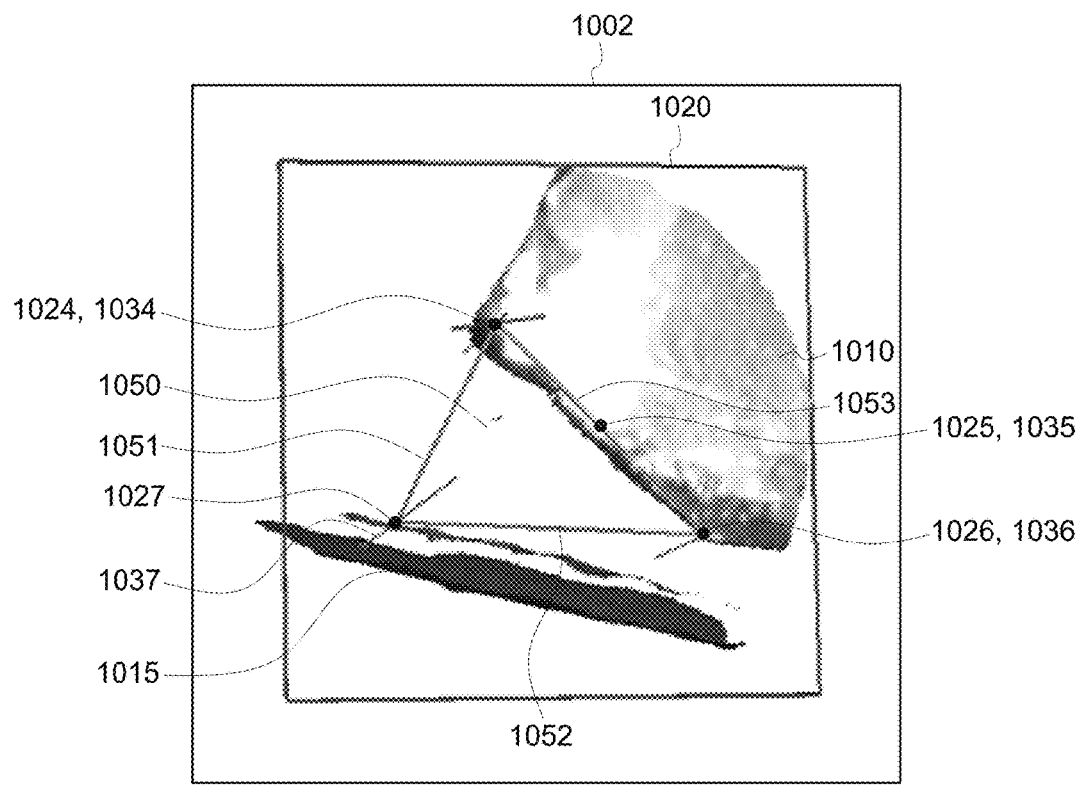
FIG. 15B is a display of a three-dimensional point cloud view of the turbine blade having a missing corner as shown in FIG. 15A in another exemplary embodiment.

FIG. 15B is a display of a three-dimensional point cloud view 1002 of the turbine blade 1010 having a missing corner (shown by polygon 1050) and a shroud 1015 as shown in FIG. 15A in an another exemplary embodiment. The three-dimensional point cloud view 1002 showing the three-dimensional surface points of the turbine blade 1010, the reference surface 1020, and the projected reference surface points 1024, 1025, 1026, 1027 allows the user to better visualize the measurement to ensure that the measurement is being performed properly. As shown in FIG. 15B, the point cloud view 1002 may include the computed three-dimensional surface coordinates on the viewed object 1010, which may be shown as individual points, a mesh, or a continuous surface. The three dimensional coordinates associated with measurement cursors 1034, 1035, 1036, 1037 may be shown as dots, spheres or the like, and interconnecting lines (polygon 1050 with sides 1051, 1052, 1053, 1054) outlining the feature (missing corner) may be included. The reference surface 1020 and its location may also be represented by an additional feature, such as a rectangle or square. Thus, the three-dimensional point cloud view 1002 allows the user to visualize the measurement in three-dimensional space to ensure that it is being performed properly. Such an assessment can be very difficult to make using only a two-dimensional image 1001. In one embodiment the three-dimensional point cloud view 1002 is displayed simultaneously with the two-dimensional image 1001, and the three-dimensional point cloud view 1002 is updated automatically when a measurement cursor is repositioned in the two-dimensional image 1001. In another embodiment the user may select to view either the two-dimensional image 1001 or the three-dimensional point cloud view 1002 individually.

Figure 15C:
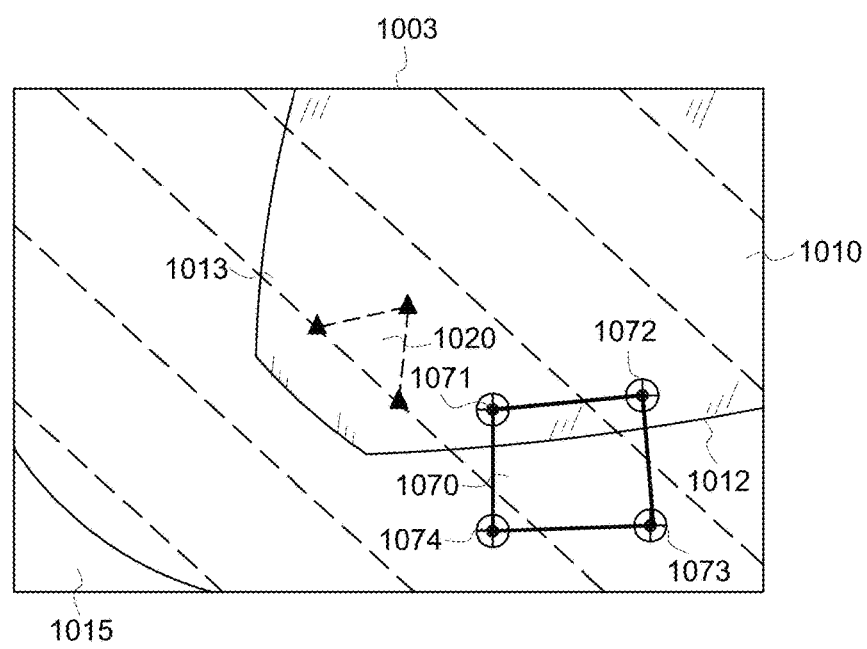
FIG. 15C is another exemplary image obtained by the video inspection device of a turbine blade having a missing corner in another exemplary embodiment.

FIG. 15C is another exemplary image 1003 obtained by the video inspection device 100 of a turbine blade 1010 having a missing corner in an another exemplary embodiment. In some cases, it may be useful to use both three-dimensional coordinates of projected reference surface points (for points off of the viewed object) and three-dimensional coordinates of surface points on the viewed object to perform a measurement. With reference to FIG. 15C, an area measurement (polygon 170) may be performed using reference surface 1020. In the illustrated embodiment, four measurement cursors 1071, 1072, 1073, 1074 may be selected, with two measurement cursors 1071, 1072 located on the surface 1013 of the viewed object 1010, and two measurement cursors 1073, 1074 located off the surface 1013 of the viewed object 1010. The two measurement cursors 1071, 1072 located on the surface 1013 of the viewed object 1010 are located on pixels associated with the three dimensional coordinates of the surface points on the on the surface 1013 of the viewed object 1010 and the three-dimensional coordinates of the projected reference surface points on the reference surface 1020. The two measurement cursors 1073, 1074 located off the surface 1013 of the viewed object 1010 are located on pixels associated with the three dimensional coordinates of the projected reference surface points on the reference surface 1020, but not associated with the three dimensional coordinates of the surface points on the surface 1013 of the viewed object 1010. The measurement may utilize the three-dimensional coordinates of the surface points located on the surface 1013 of the viewed object 1010 associated with the two measurement cursors 1071, 1072 and the three-dimensional coordinates of the projected reference surface points on the reference surface 1020 associated with the two measurement cursors 1073, 1074 located off the surface 1013 of the viewed object 1010. Alternatively, the measurement may utilize the three-dimensional coordinates of the projected reference surface points on the reference surface 1020 associated with all four measurement cursors 1071, 1072, 1073, 1074. In another embodiment, the video inspection device 100 allows the user to choose whether to use the three dimensional coordinates of the surface points on the surface 1013 of the viewed object 1010 or the three-dimensional coordinates of the projected reference surface points on the reference surface 1020 for the two measurement cursors 1071, 1072 located on the surface 1013 of the viewed object 1010. In one example, when measuring the gap between a turbine blade 1010 and the shroud 1015, a plane can be established on the shroud 1015 (using 3 cursors on pixels having associated three-dimensional coordinates), a measurement surface can be established on the blade 1010, a projected point on the edge of the blade 1010 is set using another cursor, and the perpendicular distance from the plane to the point is computed.

Figure 16:
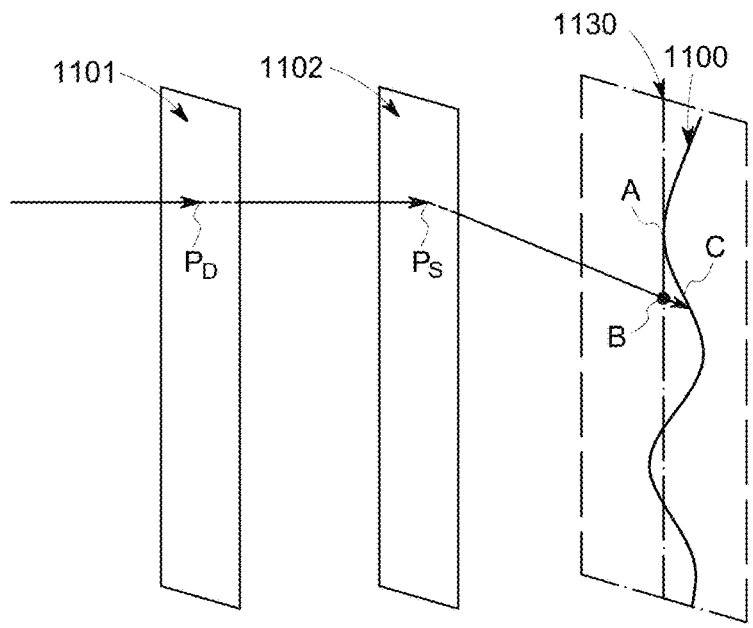
FIG. 16 illustrates relationship between image pixels, sensor pixels, reference surface coordinates, and object surface coordinates.

FIG. 16 illustrates the relationship between image pixels, sensor pixels, reference surface coordinates, and object surface coordinates, in accordance with aspects set forth herein. For example, as described below, pixels on a display 1101 may relate to pixels on a sensor 1102, which may relate, through ray equations, to a point C on the surface of an object 1100. In the illustrated embodiment, a user may establish a reference surface 1130 by choosing at least a point A on the surface of object 1100. For example, reference surface 1130 may be a plane intersecting with object 1100 at point A.

In one example, a user may desire to perform a measurement of a feature of object 1100 using reference surface 1130. In such a case, the user may select a first pixel of the feature, pixel $P_D$, on a display 1101 by positioning a cursor on the two-dimensional image shown on the display 1101. In such a case, pixel $P_D$ on display 1101 may map to pixel $P_S$ on a sensor 1102, using, for example, the displayed image pixel to captured image pixel conversion equations described below. In addition, pixel $P_S$ on sensor 1102 may map to projected three-dimensional reference surface coordinate B on reference surface 1130. In the illustrated example, pixel $P_S$ on sensor 1102 may also be associated with three-dimensional surface coordinate C on object 1100, which is a three-dimensional coordinate of the feature itself computed using the captured images. Thus pixel $P_S$ can have both an associated three-dimensional surface coordinate and a projected three-dimensional reference surface coordinate, either of which may be used to compute a measurement result. In one example, three-dimensional surface coordinate C is affected by three-dimensional data noise and therefore does not accurately represent the surface of object 1100. In this case a measurement result computed using projected three-dimensional reference surface coordinate B may be more accurate than one computed using coordinate C. In another example, coordinate C may accurately represent the surface of object 1100, and the user may select to use coordinate C rather than coordinate B for use in computing the measurement result.

In certain implementations, a measurement system may include a sensor having a certain capture resolution, such as a 640×480 charge-coupled device (CCD). In addition, the measurement system may have a user interface with a different display resolution, such as 1024×768 pixels. In such a case, when a user selects a cursor position on the user interface screen, the selected screen pixel may be mapped to a sensor pixel. With reference to a pinhole camera model, for instance, if the display resolution is 1024×768 and the capture resolution is 640×480, the capture column (col) and row may be calculated as follows:

Capture col=Display col*640/1024=Display col*0.625

Capture row=Display row*480/768=Display row*0.625

For example, a display cursor with {col, row}={15.33, 100.67} is equivalent to capture capture {col, row}={9.581, 62.919}. In such a case, bilinear interpolation may be used between capture pixels (9,62), (10,62), (9,63), (10,63), in order to interpolate the ray equations for the equivalent pixel.

In one example, the ray equations are:

$x_{r,c}(z)=a_{r,c}*z$ and $y_{r,c}(z)=b_{r,c}*z$ where $a_{a,r}$ and $b_{r,c}$ are pixel depdent.

In such a case, the interpolation coefficients may be calculated as:

$k_{c1}$=col−(int)col=9.581−9=0.581

$k_{c0}$=1−$k_{c1}$=0.419

$k_{r1}$=row−(int)row=62.919−62=0.919

$k_{r0}$=1−$k_{r1}$=0.081

$a_{9.581,62.919}=k_{c0}*k_{r0}*a_{9,62}+k_{c1}*k_{r0}*a_{10,62}+k_{c0}*k_{r1}*a_{9,64}+k_{c1}*k_{r1}*a_{10,63}$ $b_{9.581,62.919}=k_{c0}*k_{r0}*a_{9,62}+k_{c1}*k_{r0}*a_{10,62}+k_{c0}*k_{r1}*a_{9,64}+k_{c1}*k_{r1}*a_{10,63}$

A similar bilinear interpolation approach may be used to determine an x,y,z surface coordinate associated with a displayed or captured image pixel coordinate.

In one specific example, the ray equations may be used to map between two-dimensional image pixels and reference surface coordinates as follow.

The equation of a plane may be expressed as:

$z=z0+c*x+d*y$

The equation of a ray may expressed as:

$x=a*z; y=b*z$

In such a case, the intersection may be solved as follows:

$zi=z0+c*a*zi+d*b*zi$ $zi*(1-c*a-d*b)=z0$ $zi=z0/(1-c*a-d*b)$

For example, zi may be substituted into ray equations to get xi, yi. Thus, for a given two-dimensional displayed or captured image pixel coordinate, an associated projected three-dimensional reference surface coordinate, xi, yi, zi, may be computed. For a given measurement, one or more projected three-dimensional reference surface coordinates associated with one or more measurement cursor two-dimensional image pixel coordinates are computed. The one or more projected three-dimensional reference surface coordinates are then used to compute geometric dimensions of a feature of a viewed object.

In view of the foregoing, embodiments of the invention allow for measuring dimensions of features on or near the surface of an object using a video inspection system. A technical effect is to allow for accurate measurements of object features where there is no three-dimensional data or low accuracy three-dimensional data.

As shown in FIGS. 15A and 15C, common measurements performed by a video inspection device 100 of a turbine blade 1010 having a missing corner are the area of the missing corner, the length of missing portion 1051 of the first edge 1011 of the blade 1010, and the length of missing portion 1052 of the second edge 1012 of the blade 1010. However, in order to make the measurement on the reference plane 1020, a user has to visually determine exactly where to place the measurement cursor 1037 at the location where the tip or corner of the missing portion used to be, which can be difficult to extrapolate. In addition, if a user wants to find the area of the missing corner and the two lengths 1051, 1052, the user needs to place cursors to establish a reference surface and then perform an area measurement and two point-to-line measurements, requiring several cursor placements. Furthermore, the point-to-line measurements provide lengths 1051, 1052 of the missing edge portions that assume a right angle corner, which is often not the case.

Figure 17:
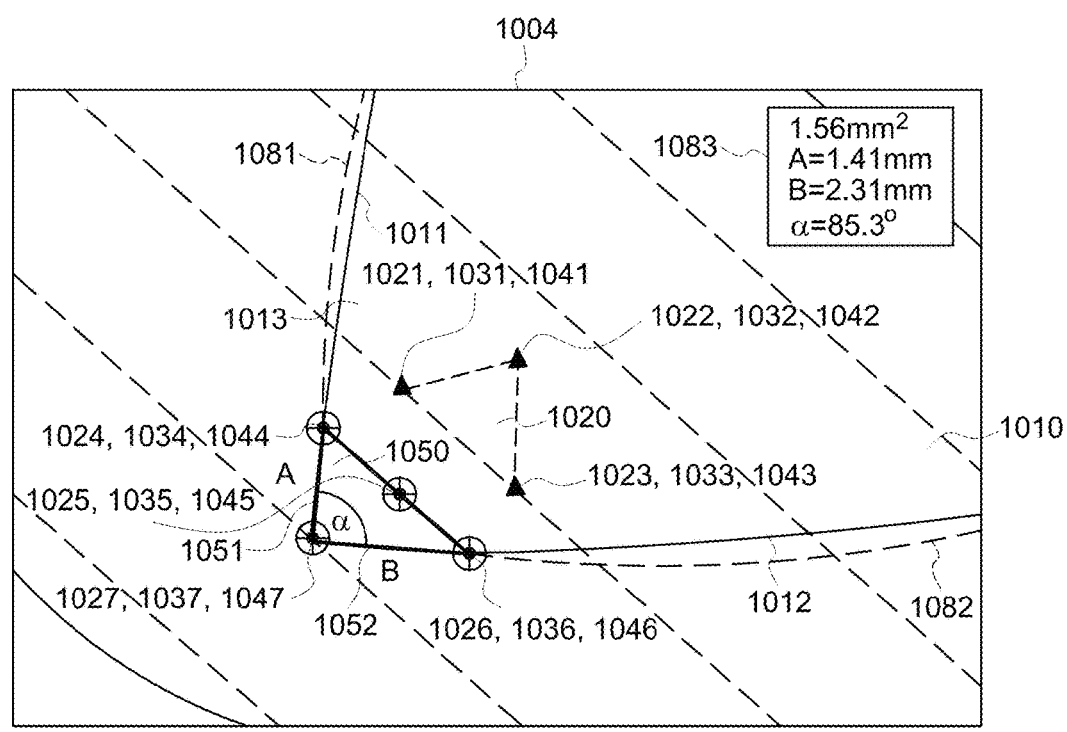
FIG. 17 is another exemplary image obtained by the video inspection device of a turbine blade having a missing corner in another exemplary embodiment.

FIG. 17 is another exemplary image 1004 obtained by the video inspection device 100 of a turbine blade 1010 having a missing corner in another exemplary embodiment. As will be explained, the video inspection device 100 is able to detect when a missing corner area measurement is being performed and simplifies the measurement to automatically obtain the area of the missing corner and the lengths 1051, 1052 of the missing edge portions. As explained above, in one embodiment and as shown in FIGS. 15A and 17, a total of three reference surface points 1021, 1022, 1023 are selected on the image 1004 of the object surface 1013 of the viewed object 1010 by placing reference surface cursors 1031, 1032, 1033 (or other pointing devices) on reference surface pixels 1041, 1042, 1043 of the image 1001 corresponding to the plurality of reference surface points 1021, 1022, 1023 on the object surface 1013. The CPU 150 of the video inspection device 100 can then determine a reference surface 1020 as described above. The user can then select the option to perform an area measurement.

In one embodiment and as shown in FIGS. 15A and 17, a total of four measurement cursors 1034, 1035, 1036, 1037 are positioned on measurement cursor pixels 1044, 1045, 1046, 1047 of the image 1001. The video inspection device 100 can then determine the projected reference surface points 1024, 1025, 1026, 1027 associated with those measurement cursor pixels 1044, 1045, 1046, 1047 on the reference surface 1020.

In one embodiment, when the video inspection device 100 (e.g., CPU 150) determines a reference surface 1020 (e.g., measurement plane) and determines that the user is performing an area measurement as shown in FIGS. 15A and 17, the video inspection device 100 can then determine if the user is performing a missing corner measurement. For example, in one embodiment, the video inspection device 100 (e.g., CPU 150) can determine the total distance between each of the measurement cursors 1034, 1035, 1036, 1037 and all three of the reference surface cursors 1031, 1032, 1033 to identify the measurement cursor 1037 having the greatest distance from the reference surface cursors 1031, 1032, 1033. The video inspection device 100 (e.g., CPU 150) can then determine the angle (α) between the two lines 1051, 1052 going to that measurement cursor 1037 in the area polygon 1050. If the angle (α) is in the range between 45 degrees and 135 degrees, the video inspection device 100 (e.g., CPU 150) determines that the user is conducting a missing corner measurement and automatically determines and displays in, e.g., a text box 1083 the area, the angle (α), and lengths 1051 (A), 1052 (B) of the missing edge portions of the blade edges 1011, 1012. In addition, to assist the user in locating the measurement cursor 1037 at the location where the tip or corner of the missing portion used to be, the video inspection device 100 (e.g., CPU 150) determines and displays a first edge line extension 1081 extending from the measurement cursor 1037 along the turbine blade first edge 1011, and a second edge line extension 1082 extending from the measurement cursor 1037 along the turbine blade second edge 1012 to provide a visual aid to the user to align those edge line extensions 1081, 1082 with the turbine blade edges 1011, 1012 to properly locate the measurement cursor 1037. As shown in FIG. 17, the first edge line extension 1081 and the second edge line extension 1082 are straight lines in three-dimensional space which appear as curved lines in the two-dimensional image 1004.

In view of the foregoing, embodiments of the invention allow for measuring the dimension of a missing corner of the turbine blade using a video inspection system. A technical effect is to allow for accurate measurements of the area and lengths of the missing corner using a minimum number of cursor placements, expediting the measurement.

Figure 19A:
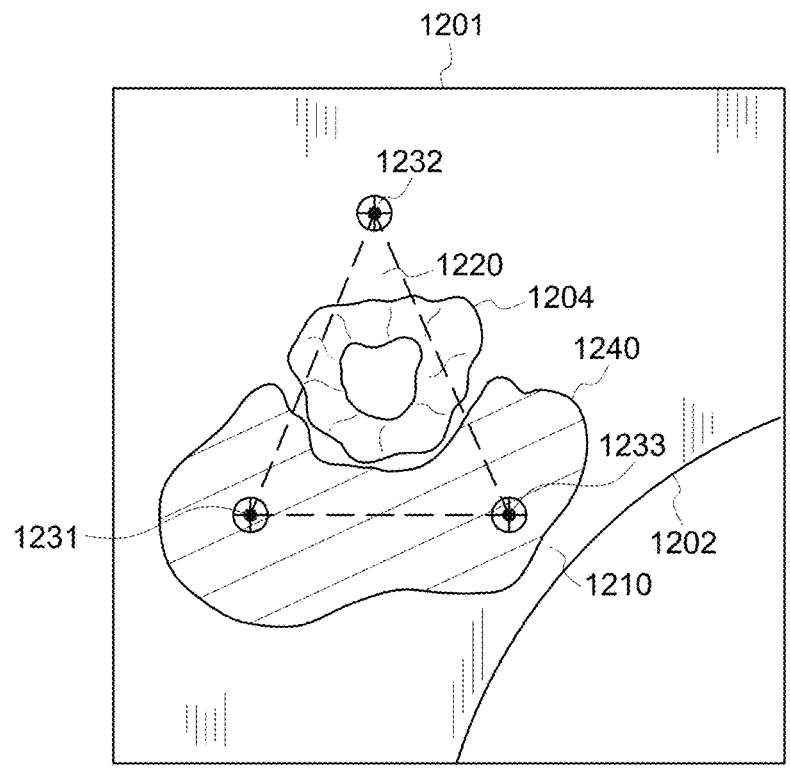
FIGS. 19A and 19B illustrate techniques for marking an image with a graphic overlay (or mask) to visualize a defined reference surface, such as a measurement plane.
Figure 19B:
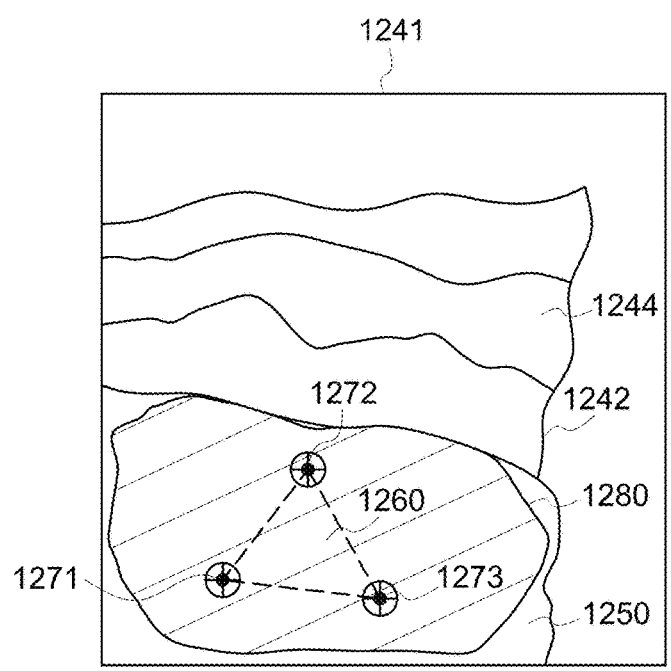

Since the reference surface described herein is used to measure key dimensions in conducting inspections using various measurements relating to the viewed object (e.g., depth, depth profile, or area depth profile measurement), it is important that the reference surface is properly aligned with, and accurately represents, the physical object surface. Noise in the three-dimensional surface coordinates selected as reference surface points can cause the reference surface to be tilted with respect to the actual surface causing poor accuracy of subsequent measurements. As will be discussed and as shown in FIGS. 19A and 19B, a visual indication, such as a semi-transparent graphic overlay 1240, 1280, can be placed on pixels in the two-dimensional image with associated surface points having three-dimensional surface coordinates less than a predetermined distance from the three-dimensional reference surface to help the user assess the matching between the reference surface and the object surface. For example, pixels of the object proximate the reference surface may be highlighted (overlayed) in a contrasting color, such as green, to provide the graphic overlay. In another example, the video inspection device 100 displays on a three-dimensional point cloud view an indication of which surface points have three dimensional coordinates that are less than a predetermined distance from the three-dimensional reference surface that can also help the user assess the matching between the reference surface and the object surface. Surface points of the object proximate the reference surface may be defined by a Cartesian distance, or may be a simplified metric such as z-value distance to allow for ease of computation. FIGS. 19A and 19B illustrate techniques for marking an image with a graphic overlay to visualize a defined reference surface, such as a measurement plane.

FIG. 19A depicts a reference surface 1220 that is poorly aligned to the object surface 1210. As shown in the image 1201 of the surface 1210 of the viewed object 1202 that includes an anomaly 1204, a reference surface 1220 is established based on the placement of reference surface cursors 1231, 1232, 1233 on the image 1201. A semi-transparent graphic overlay 1240 is overlayed on pixels in the two-dimensional image 1201 with associated surface points having three-dimensional surface coordinates less than a predetermined distance from the three-dimensional reference surface 1220. As shown in FIG. 19A, only a small portion of the reference surface 1220 is covered by the graphic overlay 1240, indicating that the reference surface 1220 is tilted or otherwise not aligned well with the object surface 1210. Accordingly, measurements taken of the anomaly 1204 with that reference surface 1220 would likely be inaccurate. The presence of the graphic overlay 1240 would prompt the user to modify the reference cursor locations to find a better matching reference surface 1220 that has better coverage by the graphic overlay 1240.

FIG. 19B depicts a well aligned reference surface 1260 where the reference surface 1260 is almost entirely covered with the graphic overlay 1280. As shown in the image 1241 of the surface 1250 of the viewed object 1242 that includes an anomaly 1244, a reference surface 1260 is established based on the placement of reference surface cursors 1271, 1272, 1273 on the image 1241. A semi-transparent graphic overlay 1280 is overlayed on pixels in the two-dimensional image 1241 with associated surface points having three-dimensional surface coordinates less than a predetermined distance from the three-dimensional reference surface 1260. As shown in FIG. 19A, the entire reference surface 1260 is covered by the graphic overlay 1280 indicating that the reference surface 1260 is properly aligned with the object surface 1250. Accordingly, measurements taken of the anomaly 1244 with that reference surface 1260 would likely be accurate. The presence of the graphic overlay 1280 would inform the user that the cursor locations do not need to modified.

In one example, the graphic overlay may be updated in real time as the cursors are moved by the user. In other examples, e.g., with measurement types such as depth profile and area depth profile measurements, the graphic overlay may be shown temporarily when a cursor is moved and may be removed a few seconds after cursor movement stops. With depth measurements, the graphic overlay may be displayed whenever a reference surface cursor is active and may be hidden if a $4^{th}$ cursor or the result is active. In another example, the graphic overlay may always be displayed whenever the reference surface is active.

In order to determine whether to place a graphic overlay on a pixel in the two-dimensional image, the video inspection device 100 (e.g., CPU 150) determines if that pixel is associated with a surface point having three-dimensional coordinates less than (or within) a predetermined distance from the three-dimensional reference surface. In some embodiments, the distance between the surface point and the reference surface can be determined as a perpendicular distance, while in other embodiments, the distance can be a non-perpendicular distance.

In one embodiment, a pixel can be included in the graphic overlay if its associated surface point is within a distance to the reference surface of +/−1% of the surface point's z value. In one embodiment, the video inspection device 100 (e.g., CPU 150) can perform a coordinate transformation such that the transformed z value for all points on the reference surface is z=0. Then for a given surface point, the video inspection device 100 (e.g., CPU 150) can compare the actual (untransformed) z value of the surface point to the transformed z value. If the absolute value of the transformed z value (which provides the perpendicular distance from the reference surface) is less than 1% of the actual z value, the pixel associated with that surface point can be included in the graphic overlay.

In another embodiment not requiring a coordinate transformation, for each pixel, the video inspection device 100 (e.g., CPU 150) can determine a perpendicular projection onto the reference surface and determine the distance from the surface point to the reference surface in a perpendicular direction. If that perpendicular distance is less than 1% of the actual z value, the pixel associated with that surface point can be included in the graphic overlay. For example, if the distance is 0.08 mm and the surface point has a z value of 10.0 mm, the pixel associated with that surface point can be included in the graphic overlay.

In another embodiment not requiring a perpendicular distance, for each pixel, the video inspection device 100 (e.g., CPU 150) can determine the actual z coordinate for the surface point and the z coordinate for the corresponding projection point on the reference surface projected from that surface point, where such projection is not necessarily in a perpendicular direction. If the difference between the z value on the reference surface and the z value of the corresponding surface point is less than 1% of either z value, the pixel associated with that surface point can be included in the graphic overlay.

In view of the foregoing, embodiments of the invention allow for determining whether a reference surface is properly aligned with, and accurately represents, the physical object surface. A technical effect is to provide more accurate measurements involving the reference surface.

Figure 20:
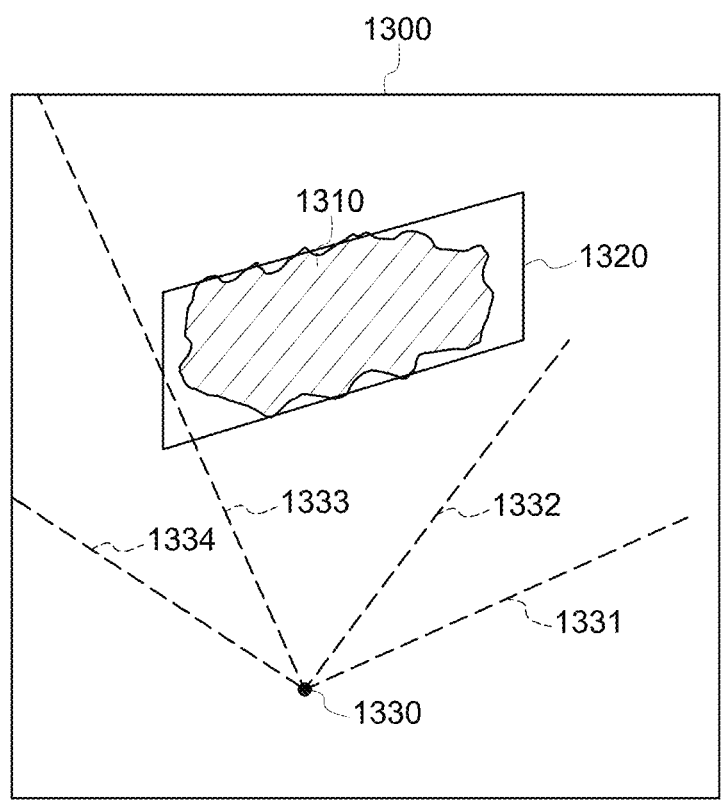
FIG. 20 shows a point cloud view of an object with field of view lines to provide a visual indication of the orientation of the tip of the probe of the video inspection device.

In some instances, it can be difficult for a user to understand the tip of a probe of a visual inspection device is oriented relative to an inspected object when looking at the two-dimensional image or even a point cloud view. For example, it may be difficult for a user to understand how to adjust the viewing perspective. FIG. 20 shows a full image point cloud view 1300 of an object 1310 displaying field of view lines 1331, 1332, 1333, 1334 extending from the field of view origin 1330 (0,0,0) to provide a visual indication of the orientation of the tip of the probe of the video inspection device 100 with respect to the object 1310. As shown in FIG. 20, the reference surface 1320 and its location may also be represented by an additional feature, such as a rectangle or square. In one embodiment, the user can turn the field of view lines 1331, 1332, 1333, 1334 on or off as desired.

In some applications involving a reference surface as described herein, it may be desirable to make a measurement on the reference surface that involves a feature that may include at least one surface point that is not located on the reference surface and that may even be a significant distance from the reference surface. When the reference surface is a reference plane, such a measurement may be described as an in-plane measurement to an out of plane surface point.

Figure 21:
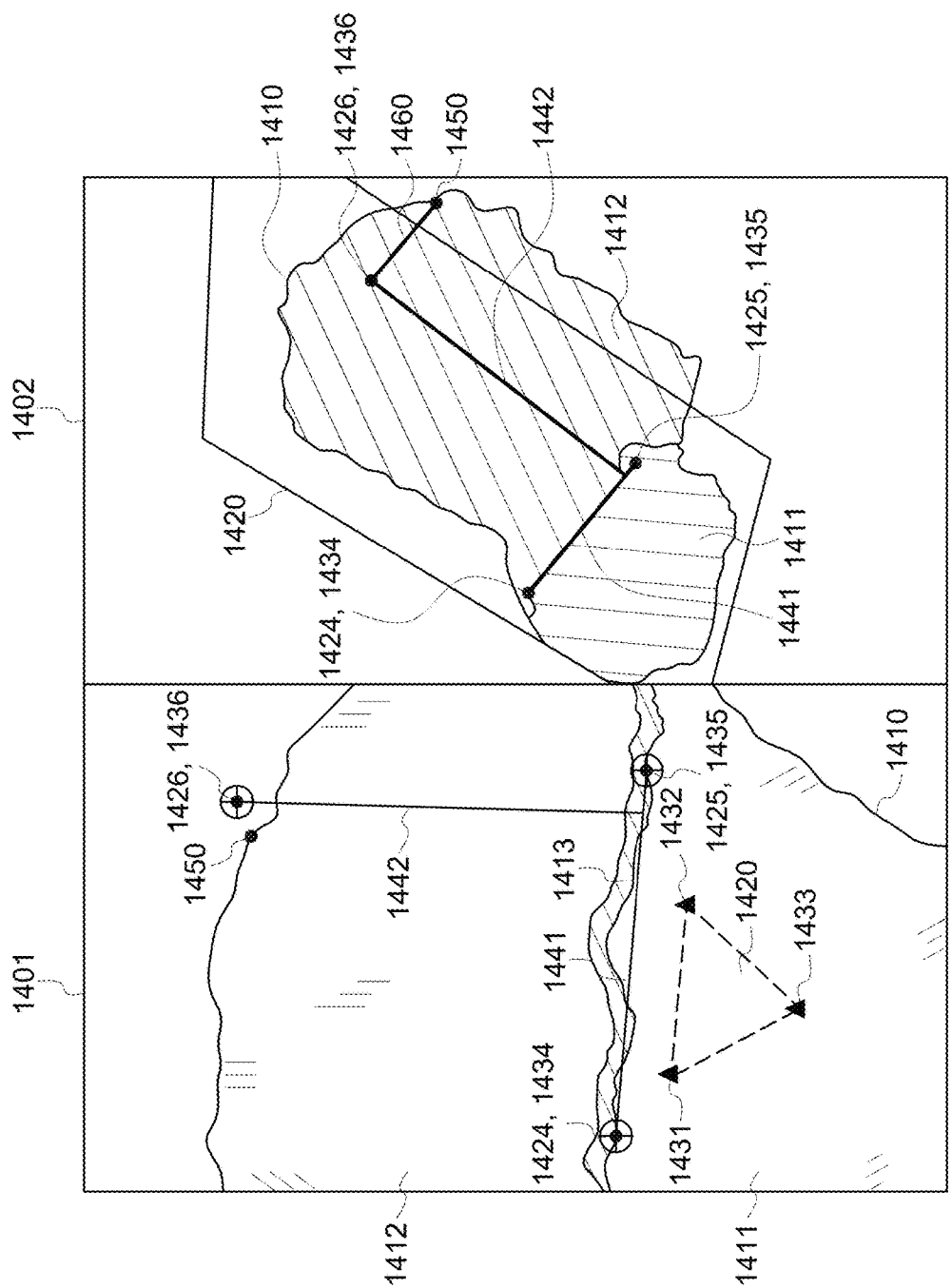
FIG. 21 shows a two dimensional image side-by-side with a three-dimensional point cloud view of an object in an exemplary embodiment.

FIG. 21 shows a two dimensional image 1401 side-by-side with a point cloud view 1402 of an object 1410 having an upper surface 1411 and a lower surface 1412. As shown in FIG. 21, a reference surface 1420 is established based on the placement of reference surface cursors 1431, 1432, 1433 on the image 1401. As explained above, through calibration, the three-dimensional trajectory associated with each pixel associated with each of the reference surface cursors 1431, 1432, 1433 is known and used to calculate where the trajectory line intersects with the reference surface 1420 in three-dimensional space to determine the projected reference surface points 1424, 1425, 1426 on the reference surface 1420. In one embodiment, a user may want to measure the distance on the reference surface 1420 from a first edge 1413 between the upper surface 1411 and the lower surface 1412 and a point of interest 1450 on the lower surface 1412 that is not on the reference surface 1420. This measurement can be performed using, e.g., a point-to-line measurement with a first measurement line 1441 (the reference line) between the first measurement cursor 1434 (reference surface point 1424) and the second measurement cursor 1435 (second reference point 1425) and a second measurement line 1442 between the first measurement line 1441 (the reference line) and the third measurement cursor 1436 (reference surface point 1426) positioned at a point on the reference surface corresponding to the location of the point of interest on the lower surface 1412.

As can be seen in the image 1401 and point cloud view 1402 of FIG. 21, based on the viewing angle and the geometry of the object 1410, the third measurement cursor 1436 (and corresponding reference surface point 1426) is visually offset (i.e., not directly above or lined up visually) from the point of interest 1450 such that finding the correct location of the third measurement cursor 1436 (and corresponding reference surface point 1426) on the reference surface 1420 that corresponds to the point of interest 1450 on the lower surface 1412 can be challenging. In order to assist the user, the video inspection device 100 (e.g., CPU 150) can provide guide lines (e.g., guide line 1460) on the point cloud view 1402 to assist the user in placing the third measurement cursor 1436.

In one embodiment, when a measurement is being performed involving a reference surface 1420 (e.g., a measurement plane), the video inspection device 100 (e.g., CPU 150) identifies points on the object surface (e.g., lower surface 1412) proximate (e.g., within 0.1 mm) lines that are perpendicular to the reference surface 1420 and passing through the projected reference surface point 1426 projected from the measurement cursor 1436. If such surface points are found, the video inspection device 100 (e.g., CPU 150) provides a guide line 1460 in the point cloud view 1402 extending in a perpendicular direction from the three-dimensional coordinate on the references surface 1420 corresponding to the measurement cursor 1436 (or corresponding reference surface point 1426). In one embodiment, a sphere is placed on the surface point (e.g., point of interest 1450 as shown in the point cloud view 1402 of FIG. 21). This guide line 1460 helps the user position the third measurement cursor 1436 on the reference surface 1420 in the two-dimensional image 1401 at the location corresponding to the point of interest 1450 to provide an accurate measurement. Accordingly, the user can move the third measurement cursor 1436 in the two-dimensional image 1401 until the guide line 1460 associated with that cursor 1436 contacts the lower surface 1412 at the point of interest 1450. In one embodiment, the guide line 1460 may be optionally hidden or shown.

Figure 22A:
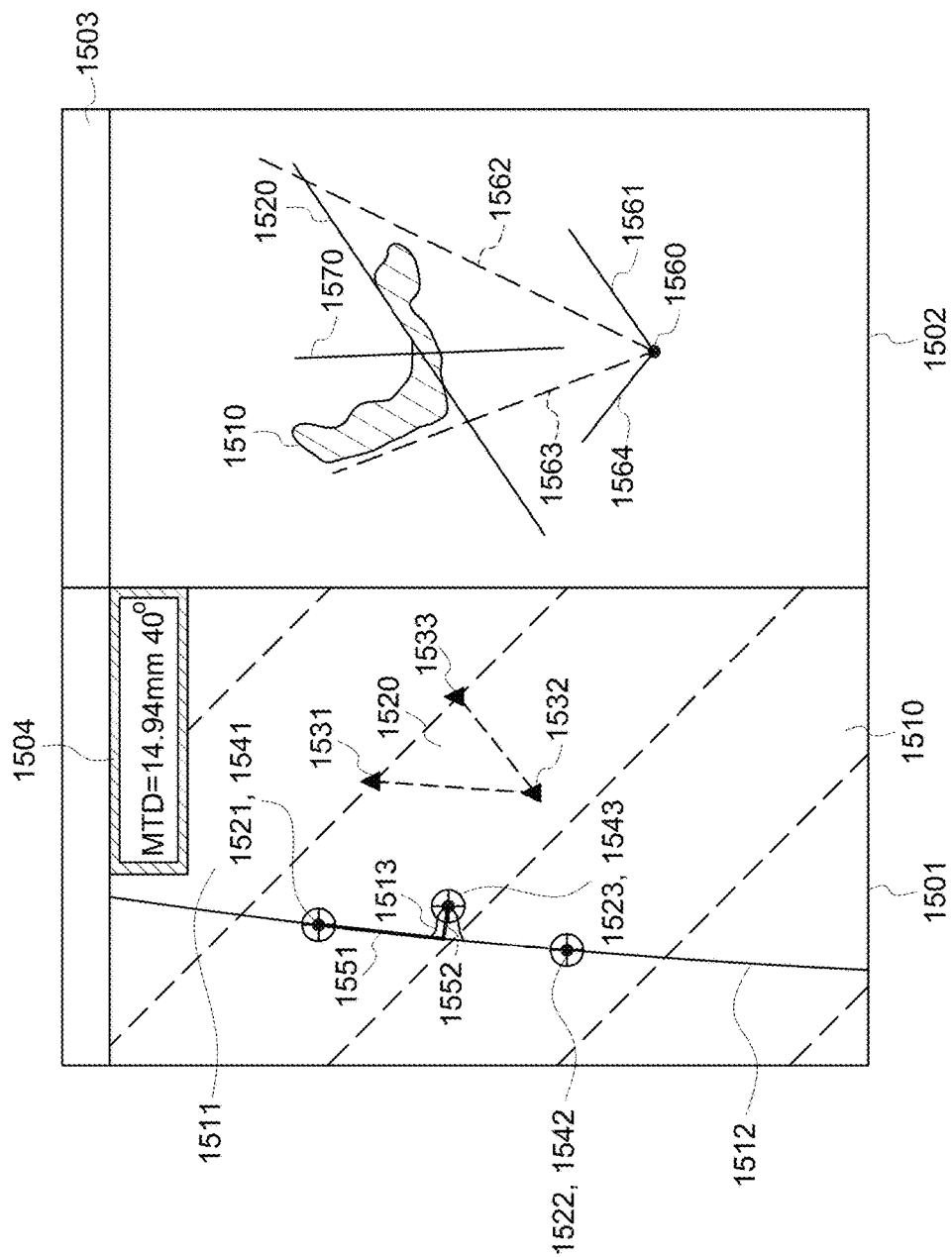
FIG. 22A shows another two dimensional image side-by-side with a point cloud view of an object in an exemplary embodiment.

In some inspections with the video inspection device 100, a user needs to place measurement cursors at the edge of an object. For example, FIG. 22A shows another two dimensional image 1501 side-by-side with a point cloud view 1502 of an object (turbine blade 1510) in an exemplary embodiment. As shown in FIG. 22A, the edge 1512 of the turbine blade 1510 has a dent 1513 that may have been caused, e.g., by a stone or other foreign object passing through the turbine engine. In one embodiment, where a user may want to measure the dimension of the dent 1513, a user can position a first measurement cursor 1541 and a second measurement cursor 1542 on the edge 1512 of the turbine blade 1510 and a third measurement cursor 1543 on the edge of the dent 1513. The three measurement cursors 1541, 1542, 1543 can be used to perform a point-to-line measurement of the depth of the dent 1513 using a first measurement line 1541 (the reference line) between the first measurement cursor 1541 and the second measurement cursor 1542 and a second measurement line 1542 between the first measurement line 1541 (the reference line) and the third measurement cursor 1543. The length of the second measurement line 1542 provides the depth of the dent 1513.

In many cases, the three-dimensional coordinates for points on the edge 1512 of the turbine blade 1510 are either not available or not highly accurate. Accordingly, as with the missing corner measurement described above, the point-to-line measurement of the dent 1513 can be performed on the reference surface (e.g., measurement plane). A reference surface 1520 is established on the surface 1511 of the turbine blade 1510 based on the placement of reference surface cursors 1531, 1532, 1533 on the image 1501 where three-dimensional coordinates are available and highly accurate. Once the reference surface 1520 is established, the point-to-line measurement of the dent 1513 can be performed on reference surface 1520 using the three-dimensional coordinates of the projected reference surface points 1521, 1522, 1523 on the reference surface 1520 associated with the measurement cursors 1541, 1542, 1543 as shown in FIGS. 22A and 22B.

The accuracy of this measurement is dependent on the accuracy of the user's placement of the first measurement cursor 1541 and the second measurement cursor 1542 on the actual edge 1512 of the turbine blade 1510. For example, the measurement is dependent on the accuracy of the user's placement of the first measurement cursor 1541 and the second measurement cursor 1542 on the actual edge 1512 of the turbine blade 1510 such that the projected reference surface points 1521, 1522 on the reference surface 1520 associated with the measurement cursors 1541, 1542 accurately reflects the geometric location of the actual edge 1512 of the turbine blade 1510. In many cases, the edge 1512 of the turbine blade 1510 is radiused or curved such that actual edge 1512 of the turbine blade 1510 curves away from the surface 1511 of the turbine blade 1510 and is not on the reference surface 1520 as shown in FIG. 22A.

Figure 22B:
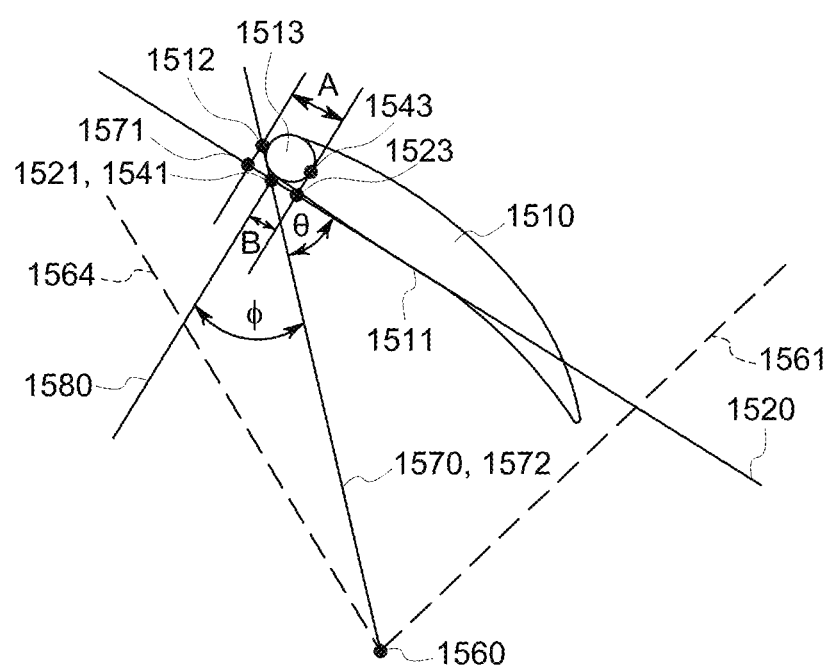
FIG. 22B shows the geometric relationship between the edge viewing angle of the video inspection device and the reference surface.

FIG. 22B shows the geometric relationship between an edge viewing angle (θ) of the video inspection device 100 and the reference surface 1520. As shown in FIGS. 22A and 22B, depending upon the edge viewing angle (θ) between the edge viewing angle line 1570 (or edge view plane 1572 described below) from the origin 1560 (coordinates (0,0,0)) of the field of view (shown by field of view lines 1561, 1562, 1563, 1564) and the reference surface 1520 or the surface 1511 of the turbine blade 1510, the user unknowingly may not be able to see the actual edge 1512 of the turbine blade 1510 when trying to place the first measurement cursor 1541 on the edge 1512 of the turbine blade 1510. For example, as shown in FIG. 22B, based on the edge viewing angle (θ), the user incorrectly places the first measurement cursor 1541, which is intended to be placed on the actual edge 1512 of the turbine blade 1510, on a point on the turbine blade 1510 that is not the edge 1512. As shown in FIG. 22B, because of the inaccurate cursor placement, the distance (B) between the projected reference surface points 1521, 1523 on the reference surface 1520 associated with the measurement cursors 1541, 1543 (i.e., the measured depth of the dent 1513) will be less than the actual depth (A) of the dent 1513 that would have been measured based on a correct projected reference surface point 1571 that would have resulted if the first measurement cursor 1541 was placed on the actual edge 1512. This error could possibly have been avoided if the edge viewing angle (θ) between the edge viewing angle line 1570 (or edge view plane 1572 described below) and the reference surface 1520 or the surface 1511 of the turbine blade 1510 were closer to 90 degrees (or if the edge viewing angle (φ) between the edge viewing angle line 1570 (or edge view plane 1572 described below) and a plane 1580 normal to the reference surface 1520 or the surface 1511 of the turbine blade 1510 were closer to 0 degrees).

In one embodiment and as shown in FIGS. 22A and 22B, the video inspection device 100 can employ a warning system where a user is given a visual or audible warning when there is an undesirable (e.g., far from perpendicular) viewing perspective at the location where a measurement cursor is being placed on an edge. In one embodiment involving a point-to-line measurement or other measurement (area, length, depth, etc.) involving the edge 1512 of an object 1510 involving two or more measurement cursors 1541, 1542 placed along the edge 1512 of the object 1510 to form a first measurement line 1551 (reference line), the video inspection device 100 (e.g., CPU 150) uses edge detection to determine whether either measurement cursor 1541, 1542 is located near an edge (e.g., the edge 1512 of the turbine blade 1510). If one or more measurement cursors 1541, 1542 are placed along the edge 1512, the video inspection device 100 (e.g., CPU 150) can determine an edge view plane 1572 based on the three-dimensional coordinates of the origin 1560 of the field of view (0,0,0) and the three-dimensional coordinates associated with the measurement cursors 1541, 1542 placed along the edge 1511 of the turbine blade 1510. In one embodiment, as shown in FIG. 22B, the video inspection device 100 (e.g., CPU 150) then determines the edge viewing angle (θ) between the edge view plane 1572 and the reference surface 1520, which would ideally be 90 degrees (perpendicular) for the best edge viewing angle for cursor placement on an edge. In another embodiment, the video inspection device 100 (e.g., CPU 150) determines the edge viewing angle (φ) between the edge view plane 1572 and a plane 1580 normal to the reference surface 1520 and including the three-dimensional coordinates associated with the measurement cursors 1541, 1542 placed along the edge 1511 of the turbine blade 1510, which would ideally be 0 degrees (parallel) for the best edge viewing angle for cursor placement on an edge. If the calculated edge viewing angle (θ or φ) is outside of an acceptable range of angles or exceeds (or falls below) a threshold) (e.g., if θ is less than 60 degrees or if φ is greater than 30 degrees), then the video inspection device 100 can display a warning message 1503 to the user (e.g., "To improve accuracy, capture with a more perpendicular view at cursors near edges"). The border of the text box 1504 showing the measurement and edge viewing angle can be illuminated in warning color (orange) and flash to warn the user. In addition, an edge view angle line 1570, which lies on the edge view plane 1570 and is perpendicular to the first measurement line 1541 (the reference line) can also be shown in a warning color (e.g., orange) on the point cloud view 1502. As shown in FIG. 22A, the point cloud view 1502 includes field of view lines 1561, 1562, 1563, 1564 and a representation of the reference plane 1520 to assist the user in repositioning the tip of the probe of the video inspection device to improve the edge viewing angle for more accurate cursor placement.

In the exemplary point-to-line measurement shown in FIGS. 22A and 22B, in addition to the first measurement cursor 1541 and the second measurement cursor 1542 being placed on the edge 1512 of the turbine blade 1510, the third measurement cursor 1543 is also placed along an edge of the dent 1513. Similarly, in FIGS. 17A and 17C, the third or fourth cursors involved in a measurement and offset from the first two measurement cursors may also be placed on another edge of the object. In one embodiment, in addition to determining an edge view plane 1572 based on the first two measurement cursors 1541, 1542 that form the first measurement line 1551 (reference line), the video inspection device 100 (e.g., CPU 150) can also determine whether the third measurement cursor 1543 is near an edge and whether that edge is parallel or perpendicular to the first measurement line 1551 (reference line). The video inspection device 100 (e.g., CPU 150) can determine a point view plane based on the three-dimensional coordinates of the origin 1560 of the field of view (0,0,0) and the three-dimensional coordinates associated with the third measurement cursor 1543 and an additional point offset from the third measurement cursor 1543 in a direction parallel or perpendicular to the first measurement line 1551 (reference line) depending on the direction of the detected edge. In one embodiment, the video inspection device 100 (e.g., CPU 150) then determines the point viewing angle between the point view plane and the reference surface 1520, which would ideally be 90 degrees (perpendicular) for the best viewing angle for cursor placement on an edge. In another embodiment, the video inspection device 100 (e.g., CPU 150) determines the point viewing angle between the point view plane and a plane normal to the reference surface 1520 and including the three-dimensional coordinates associated with the third measurement cursor 1543 and the additional point offset from the third measurement cursor 1543, which would ideally be 0 degrees (parallel) for the best viewing angle for cursor placement on an edge.

The video inspection device 100 (e.g., CPU 150) then determines a selected viewing angle between the edge viewing angle and the point viewing angle, wherein the selected viewing angle is then used to determine whether a warning needs to be provided. For example, if (i) none of the measurement cursors 1541, 1542, 1543 are near an edge or (ii) at least one of the first measurement cursor 1541 or the second measurement cursor 1542 is near an edge and the third measurement cursor 1543 is near an edge, the selected viewing angle is the larger of the edge viewing angle and the point viewing angle. If at least one of the first measurement cursor 1541 or the second measurement cursor 1542 is near an edge, but the third measurement cursor 1543 is not, then the selected viewing angle is the edge viewing angle. If neither of the first measurement cursor 1541 or the second measurement cursor 1542 is near an edge, but the third measurement cursor 1543 is near an edge, then the selected viewing angle is the point viewing angle. If the selected viewing angle ($\theta$ or $\varphi$) is outside of an acceptable range of angles or exceeds (or falls below) a threshold), then the video inspection device 100 can display a warning message 1503 to the user (e.g., "To improve accuracy, capture with a more perpendicular view at cursors near edges"). The border of the text box 1504 showing the measurement and edge viewing angle can be illuminated in warning color (orange) and flash to warn the user.

In view of the foregoing, embodiments of the invention warn the user when the viewing angle is likely to produce inaccurate cursor placements. A technical effect is to provide more accurate measurements involving cursor placements.

In some situations, a user may desire to perform measurements on or near turbines which may have blades with curved edge profiles. For instance, if damage occurs along the edge, the user may need to measure how far in from the edge the damage extends. In addition, the user may also use a grinding tool and remove material from the edge around the damage. In such a case, the user may need to measure both the damage and grinding depths from the original curved edge to ensure achievement of a profile that will not have stress concentrations that could cause failure. Point-to-line measurements that do not account for the curvature of the blade edge cannot provide the desired information.

An advantage that may be realized using the techniques presented herein, may include the use of reference profiles, go beyond point-to-line measurements, and are able to account for the curvature of objects such as the blade edge of a turbine. In one embodiment a three-dimensional reference profile is defined using points along the edge of an un-damaged blade and then recalled when measuring on an image of a damaged or repaired blade. This allows for measurements to be made from the curved original surface. In such a case, a reference surface is used to orient the reference profile to the face of the blade in three-dimensional space both when defining it and recalling it.

When the profile is recalled for use on a blade that has been damaged or blended (ground), the reference profile may be positioned to align with remaining unaltered edges of the blade in three-dimensional space. There are several ways this can be done. One example is to use the three-dimensional coordinates associated with the reference surface cursors to establish an alternate coordinate system in the original image in which the reference profile is defined and in the $2^{nd}$ image in which it is recalled and then to use this alternate coordinate system to define and then reconstruct the profile in three-dimensional space. Thus placing the reference surface cursors at the same locations on the blade in both images would position the recalled reference profile in the same location and orientation in three-dimensional space relative to the blade as it was in the first image in which it was defined regardless of changes in viewing position or angle.

Alternately, the recalled reference profile may be positioned directly in the three-dimensional view. The position of the recalled reference profile can also be shown in the two-dimensional image by identifying two-dimensional pixels that have pixel rays that pass within a maximum distance of the recalled reference profile in three-dimensional space. In another embodiment, the three-dimensional coordinates defining the reference profile may be determined using a CAD model or physical example of the blade, which can then be imported and positioned to align to the blade. In another embodiment, the system can store multiple reference profiles, and the user can recall one or more for use. In another embodiment, the system can compute geometric dimensions using a recalled reference profile. For example, the shortest distance between the recalled reference profile and a user-designated three-dimensional surface coordinate or projected three-dimensional reference surface coordinate may be computed.

Figure 18:
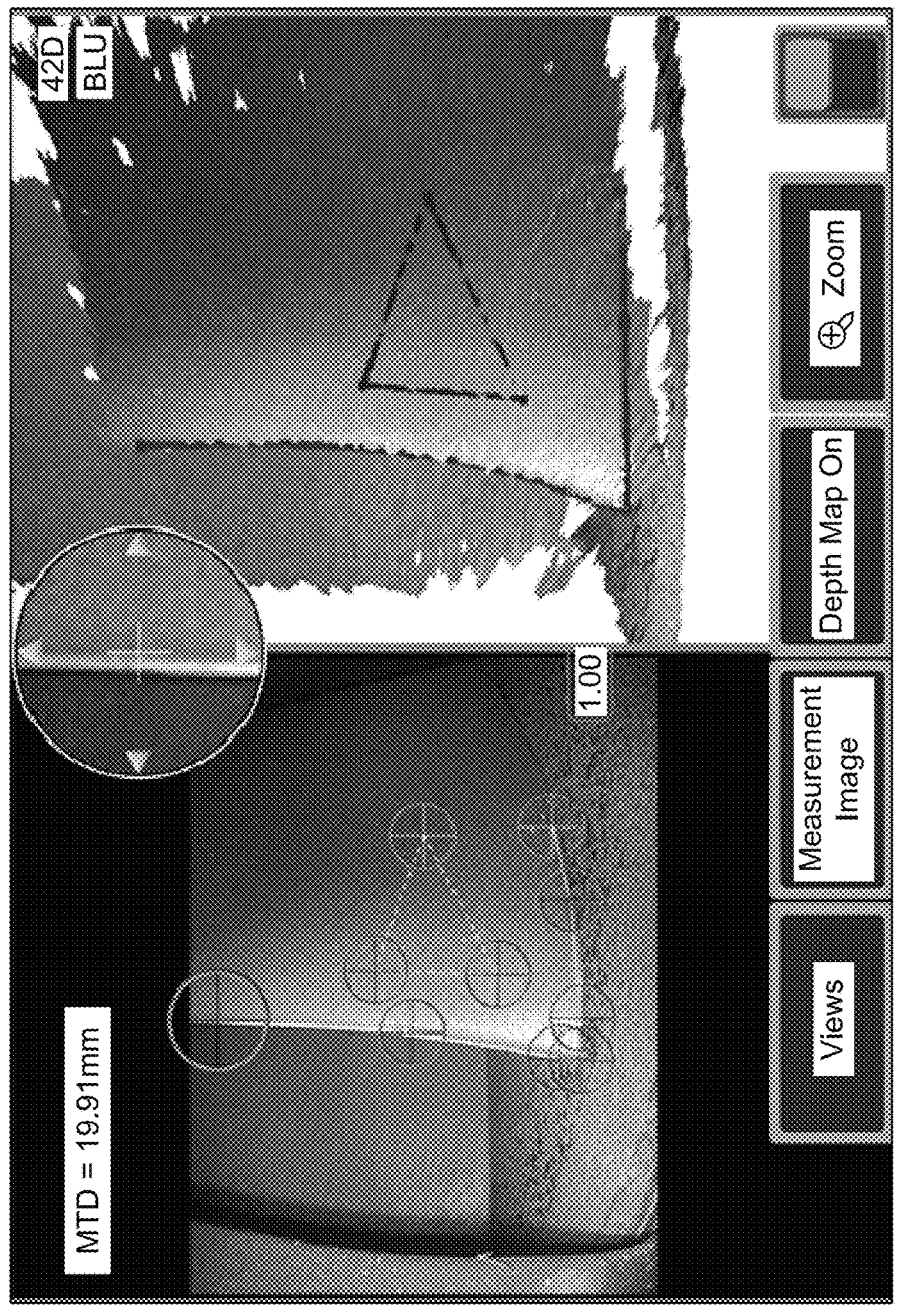
FIG. 18 shows a side by side two-dimensional/three-dimensional view of a measurement plane and a reference profile.

FIG. 18 shows a side by side two-dimensional/three-dimensional view of a measurement plane (3 connected cursors) and a reference profile defined by the other 7 cursors. The reference profile uses three-dimensional cubic spline fitting to better follow the curved edge profile with just a few cursors as is shown in the point cloud. In this case, the reference profile is defined using three-dimensional surface coordinates, though it could also be defined using projected three-dimensional measurement surface coordinates. The three-dimensional surface coordinates at the cursor locations can be saved to represent the reference profile.

Video inspection devices can be used to perform various measurements to determine the depth or height of a particular surface point or between surfaces, including measurement of blade tip to shroud gaps, depths of pits or dents, the inside diameter of a pipe, a weld height, a stator vane rock, a gap width, etc. For example, FIGS. 23A-25 show various two-dimensional and three-dimensional (point cloud) views used, which can measure the depth of a pit or dent. One of the challenges of making such a depth measurement can be accurately placing a measurement cursor at a point, for example, the deepest point of the pit or dent. As will be explained and as shown in FIGS. 23A-25, a visual indication, such as a semi-transparent depth plane graphic overlay 1650 (e.g., light blue), can be placed on pixels associated with surface points having three-dimensional surface coordinates less than a predetermined distance from a depth plane 1652 that is parallel to a reference surface (e.g., plane) 1620 and passes through the measurement point 1624 corresponding to the location of measurement cursor 1634 to help the user place the measurement cursor 1634 at the deepest point.

Figure 23A:
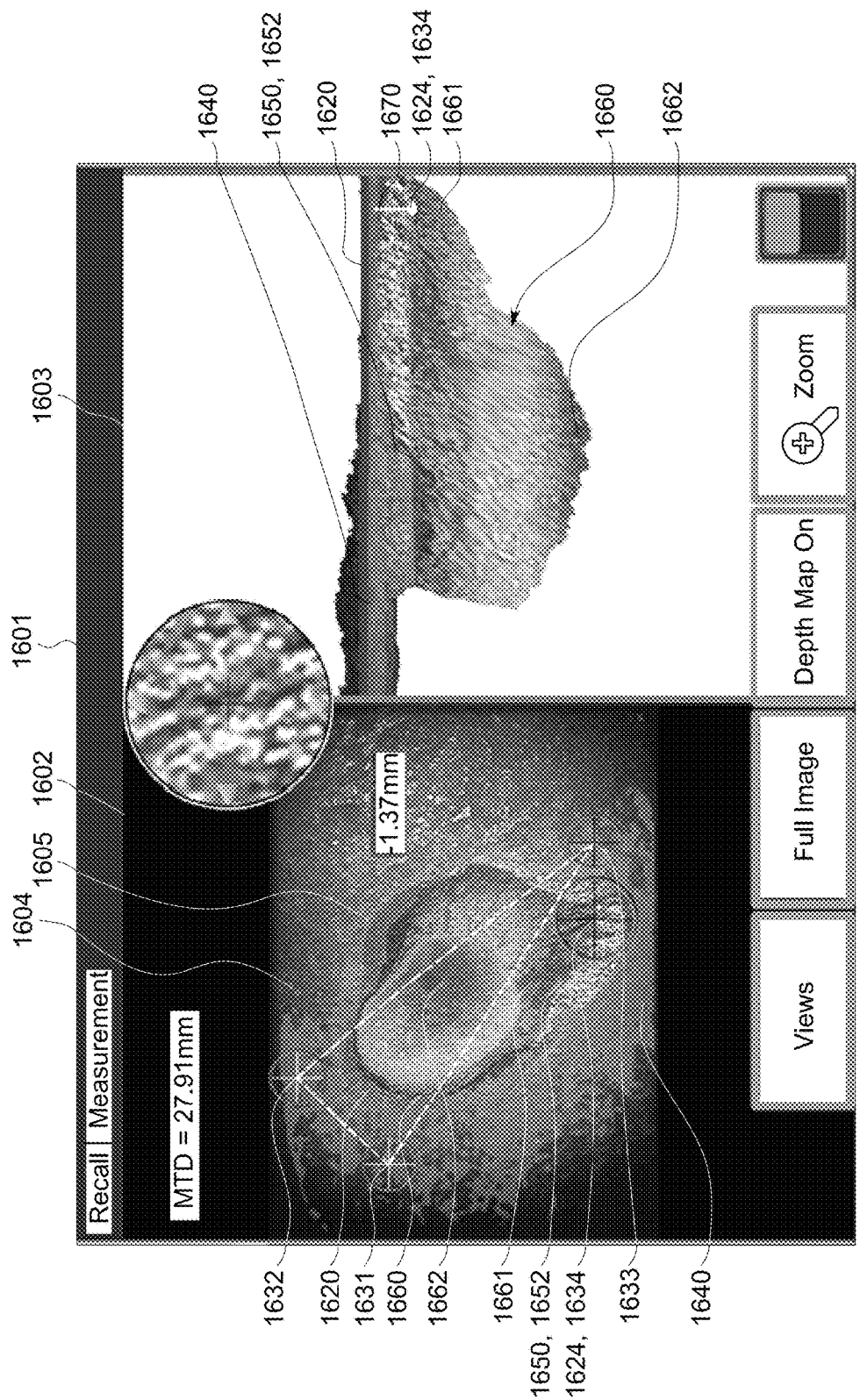
FIG. 23A is a side-by-side image displaying a two-dimensional image of the viewed object having a pit or dent and a three-dimensional point cloud view of the pit or dent illustrating a depth plane graphic overlay (or mask), where the measurement cursor is located far from the deepest point.
Figure 23B:
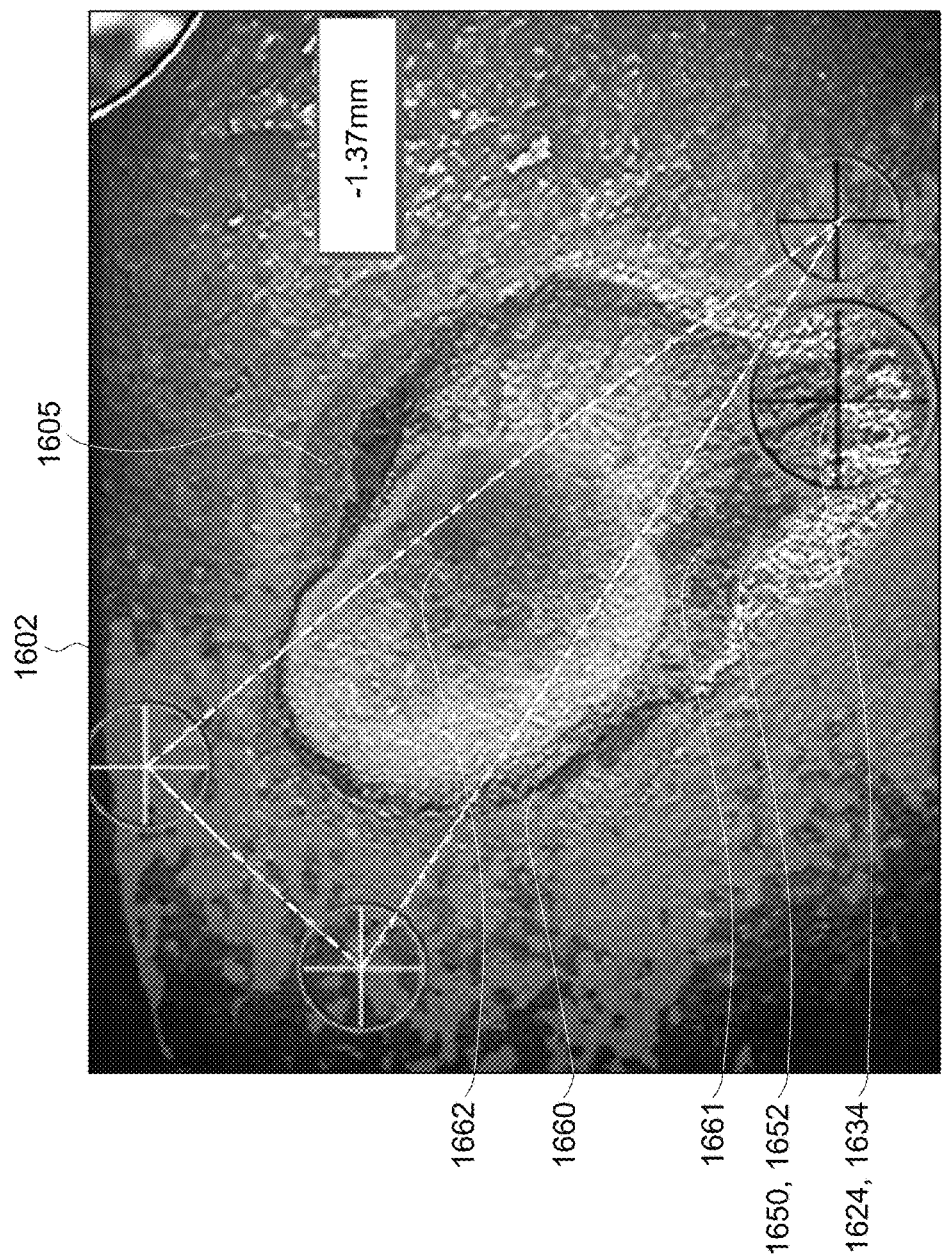
FIG. 23B is an enlarged view of the two-dimensional image of the viewed object having a pit or dent shown in FIG. 23A illustrating the depth plane graphic overlay.

FIG. 23A is a side-by-side image 1601 displaying a two-dimensional image 1602 of the viewed object 1604 having a pit or dent 1605 and a three-dimensional point cloud view 1603 of the pit or dent 1605 illustrating a depth plane graphic overlay 1650 (e.g., in a light blue color), where the measurement cursor 1634 is located far from the deepest point. FIG. 23B is an enlarged view of the two-dimensional image 1602 of the viewed object 1604 having a pit or dent 1605 shown in FIG. 23A illustrating the depth plane graphic overlay 1650.

In one embodiment and as shown in FIG. 23A, a total of three reference surface cursors 1631, 1632, 1633 (or other pointing devices) are placed on the two-dimensional image 1602 or the point cloud view 1603 to form a reference surface 1620. As explained with respect to FIGS. 19A and 19B, a reference surface overlay 1640 (e.g., in a green color) can be placed on pixels in the two-dimensional image 1602 or the point cloud view 1603 with associated surface points having three-dimensional surface coordinates less than a predetermined distance from the three-dimensional reference surface 1620 to help the user assess the matching between the reference surface 1620 and the object surface 1604.

In the depth measurement illustrated in FIGS. 23A and 23B, the measurement cursor 1634 should be placed at the deepest point of the pit or dent 1605 to accurately measure the depth 1670 of the anomaly. In order to assist the user in accurately placing the measurement cursor 1634, the video inspection device 100 (e.g., the CPU 150) can determine a depth plane 1652 that is parallel to the reference surface (e.g., plane) 1620 and passes through the measurement surface point 1624 corresponding to the location of measurement cursor 1634. The video inspection device 100 can then place a semi-transparent depth plane graphic overlay 1650 (e.g., in a light blue color) on pixels in the two-dimensional image 1602 and the point cloud view 1603 associated with surface points having three-dimensional surface coordinates less than a predetermined distance from the depth plane 1652 to help the user place the measurement cursor 1634 at the deepest point.

In order to determine whether to place a depth plane graphic overlay 1650 on a pixel in the two-dimensional image, the video inspection device 100 (e.g., CPU 150) can determine if that pixel is associated with a surface point having three-dimensional coordinates less than (or within) a predetermined distance from the depth plane 1652. In some embodiments, the distance between the surface point and the depth plane 1652 can be determined as a perpendicular distance, while in other embodiments, the distance can be a non-perpendicular distance. In one embodiment, surface points of the object proximate the depth plane 1652 may be defined by a fixed perpendicular distance (e.g., ±0.1 mm), a variable perpendicular distance, or a simplified metric such as z-value distance to allow for ease of computation. In one embodiment, the depth plane graphic overlay 1650 includes any surface point having a perpendicular distance from the depth plane 1652 of less than 0.2% of the z-value of the surface point 1624. In another embodiment, the depth plane graphic overlay 1650 includes any surface points having a perpendicular distance from the depth plane 1652 of less than 1% of the measured depth 1670.

In an embodiment, the video inspection device 100 (e.g., CPU 150) can perform a coordinate transformation such that the transformed z value for all points on the depth plane 1652 is z=0. Then for a given surface point, the video inspection device 100 (e.g., CPU 150) can compare the actual (untransformed) z value of the surface point to the transformed z value. If the absolute value of the transformed z value (which provides the perpendicular distance from the reference surface) is less than 0.2% of the actual z value, the pixel associated with that surface point can be included in the graphic overlay.

In another embodiment not requiring a coordinate transformation, for each pixel, the video inspection device 100 (e.g., CPU 150) can determine a perpendicular projection onto the depth plane 1652 and determine the distance from the surface point to the depth plane 1652 in a perpendicular direction. If that perpendicular distance is less than 0.2% of the actual z value, the pixel associated with that surface point can be included in the graphic overlay.

In another embodiment not requiring a perpendicular distance, for each pixel, the video inspection device 100 (e.g., CPU 150) can determine the actual z coordinate for the surface point and the z coordinate for the corresponding projection point on the depth plane 1652 projected from that surface point, where such projection is not necessarily in a perpendicular direction. If the difference between the z value on the depth plane 1652 and the z value of the corresponding surface point is less than 0.2% of either z value, the pixel associated with that surface point can be included in the graphic overlay.

As shown in FIGS. 23A-25, if the resultant depth measurement is negative, indicating that measurement point 1624 is below the reference surface 1620, a depth color gradient overlay 1660 can be used to highlight regions deeper than the measurement cursor 1634 and associated measurement point 1624 with a first color 1662 (e.g., red)

indicating the deepest points (farthest from the reference plane 1620) and a second color 1661 (e.g., dark blue) indicating the shallowest points (closest to the depth plane 1652). In one embodiment, the color of the depth plane graphic overlay 1650 should distinguish from the gradient colors at nearby depths (e.g., light blue overlay distinguishes from dark blue overlay used in gradient for shallowest point). In one embodiment, the depth color gradient overlay 1660 highlights surface points below the depth plane 1652 down to the deepest point of the anomaly. The color overlays may vary and may be preprogrammed and/or chosen by a user or through other means.

The video inspection device 100 (e.g., CPU 150) can conduct a flooding operation to seek out surface points to be included in the scaling of the depth color gradient overlay 1660 that are connected to the measurement point 1624 and are deeper than, e.g., a plane that is half way between the reference surface 1620 and the depth plane 1652 to avoid including undesirable or irrelevant surface points in the depth plane graphic overlay 1650. In that way, un-connected negative areas are not part of the scaling of the depth color gradient overlay 1660 to keep the depth color gradient overlay 1660 scaled to the likely area of interest instead of being overly inclusive of far-away points on other surfaces, etc. In an embodiment, the flooding operation starts with the pixel associated with the measurement surface cursor 1634 and/or measurement point 1624 and determines what pixels are connected to that pixel. If those pixels are associated with surface points that are deeper than the plane that is half way between the reference surface 1620 and the depth plane 1652, they are included as connected points in the flooding operation. Then pixels that are connected to those pixels are similarly evaluated. When the flooding operation is completed, the depth color gradient overlay 1660 can be scaled based on the deepest point(s) identified by the flooding operation.

In one example, the depth plane graphic overlay 1650 may be updated in real time as the measurement cursor 1634 is moved by the user. In other examples, e.g., with measurement types such as depth profile and area depth profile measurements, the depth plane graphic overlay 1650 may be shown when the measurement cursor 1634 is active and can be turned off when the measurement result is active. In one embodiment, when the last measurement cursor 1634 is placed and the measurement result is displayed and becomes active, the depth plane graphic overlay 1650 is briefly displayed then hidden until a cursor is activated. The real time display of the depth plane graphic overlay 1650 and the depth color gradient overlay 1660 during measurement can allow the user to more accurately place the measurement cursor 1634 on the desired surface point (e.g., the deepest point of the pit or dent 1605).

For example, as shown in FIGS. 23A and 23B, when the measurement cursor 1634 is located far from the deepest point of the pit or dent 1605, the depth plane graphic overlay 1650 and depth color gradient overlay 1660 show that there are several surface points that are deeper than the measurement point 1624, indicating that the measurement cursor 1634 should be moved toward the deepest points (e.g., shown in a first color 1662 (e.g., red) in the depth color gradient overlay 1660). This is also shown on the point cloud view 1603 of FIG. 23A, where the depth 1670 of the measurement cursor 1634 and associated measurement point 1624 are located far from the deepest point 1662 of the pit or dent 1605.

Figure 24A:
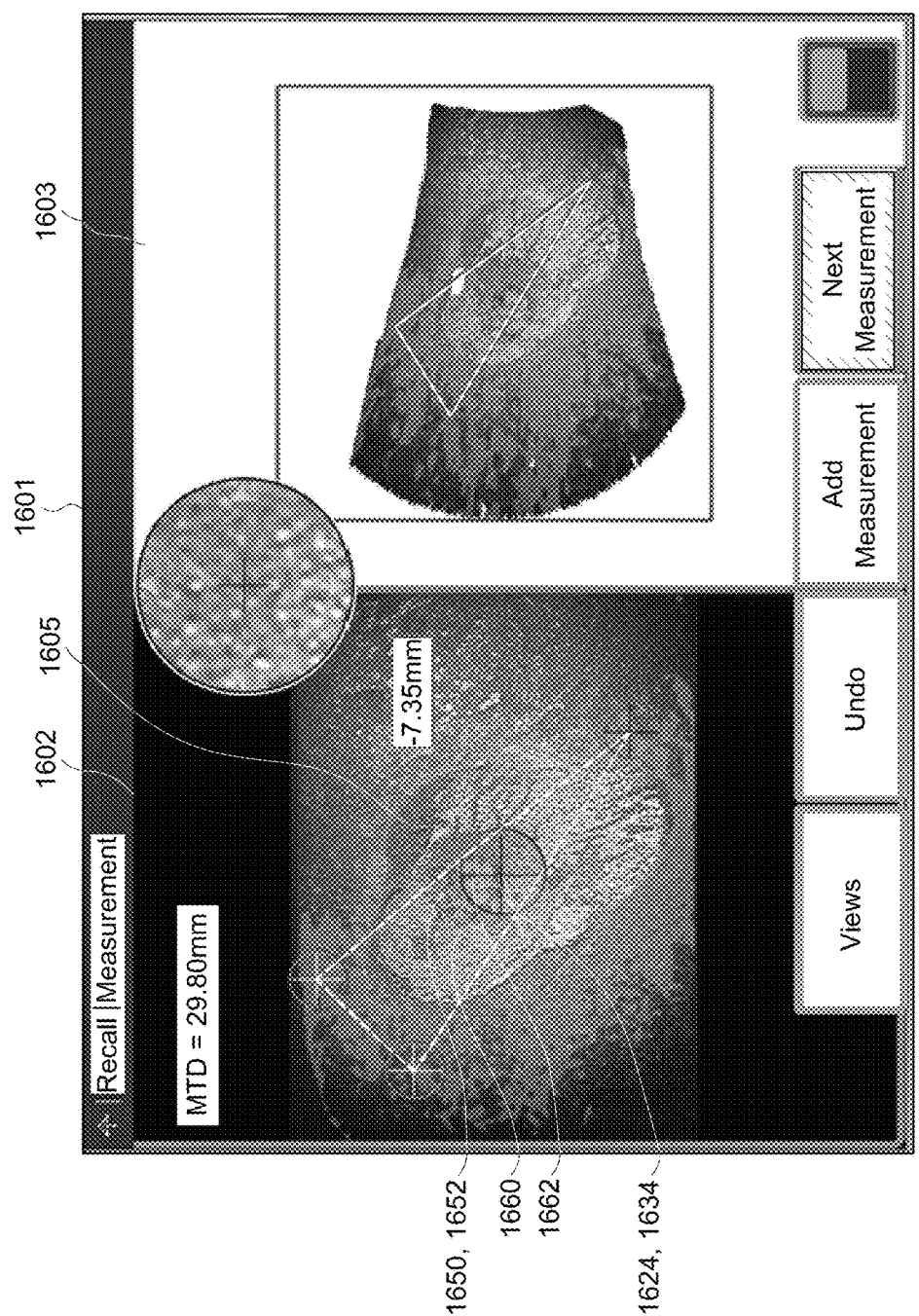
FIG. 24A is a side-by-side image displaying a two-dimensional image of the viewed object having a pit or dent and a three-dimensional point cloud view of the pit or dent illustrating a depth plane graphic overlay, where the measurement cursor is located closer to the deepest point than in FIG. 23A.
Figure 24B:
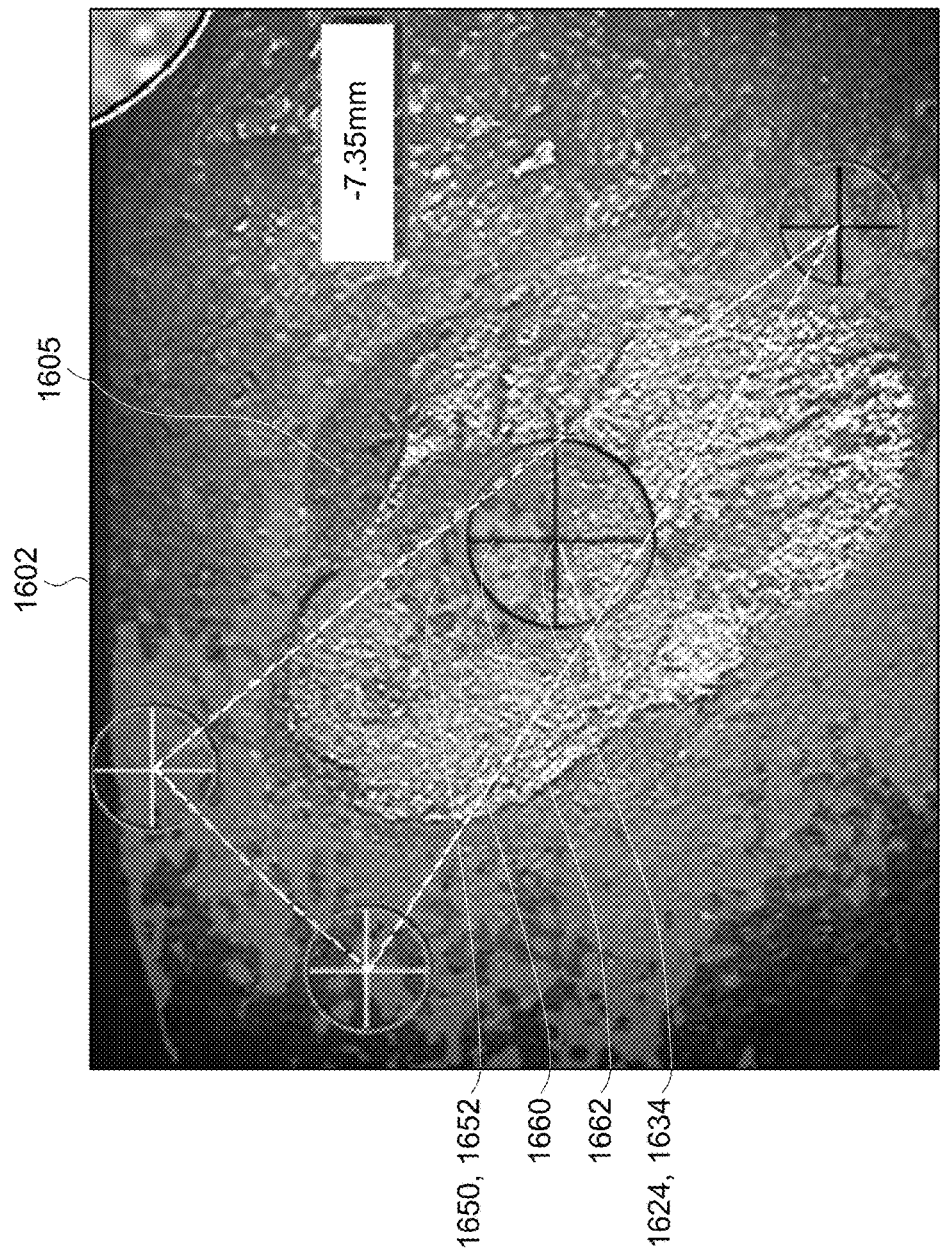
FIG. 24B is an enlarged view of the two-dimensional image of the viewed object having a pit or dent shown in FIG. 24A illustrating the depth plane graphic overlay.
Figure 25:
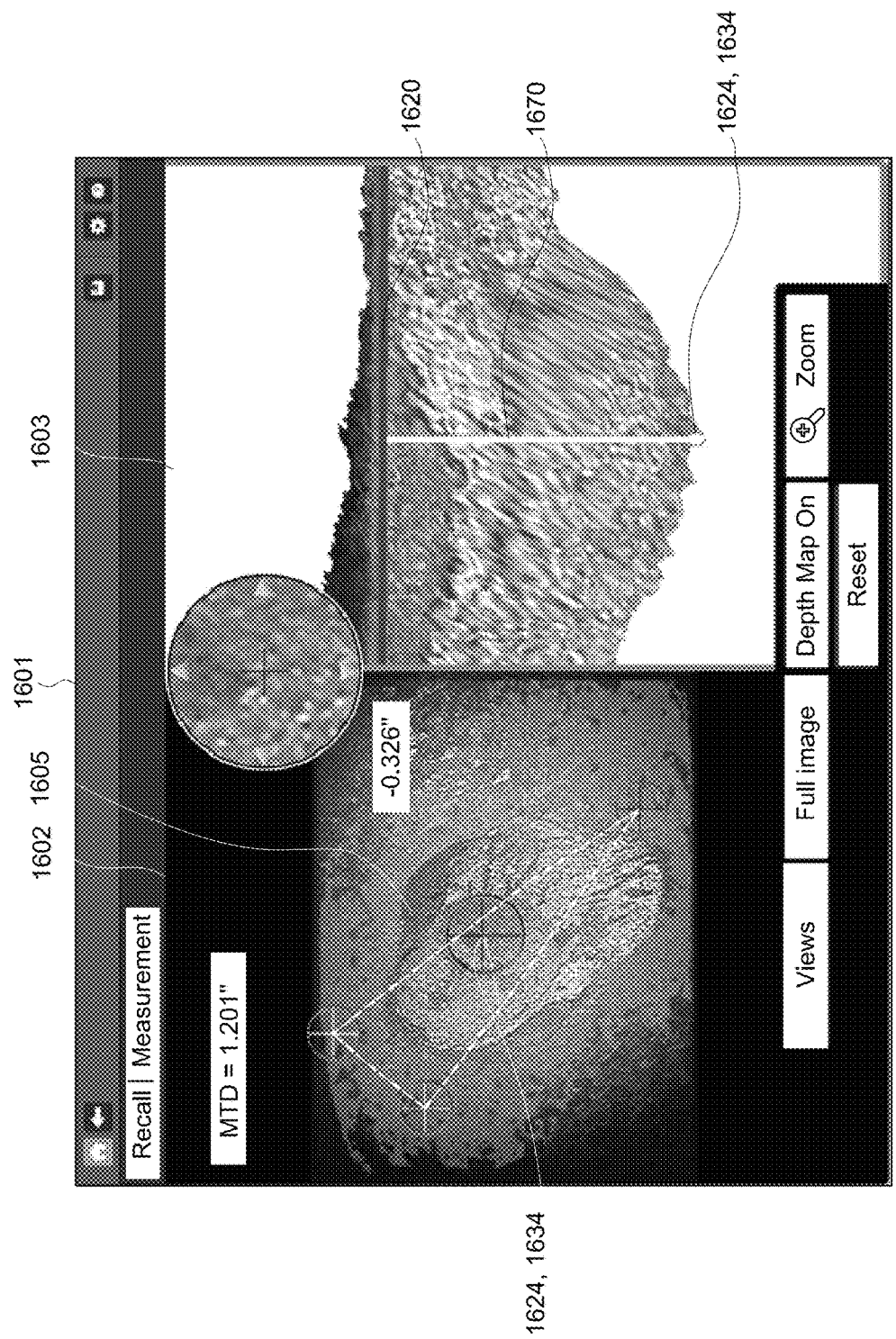
FIG. 25 is a side-by-side image displaying a two-dimensional image of the viewed object having a pit or dent and a three-dimensional point cloud view of the pit or dent illustrating a depth plane graphic overlay, where the measurement cursor is located at the deepest point.

The relatively large area of the depth color gradient overlay 1660 in FIGS. 23A and 23B indicates, for example, to the user that there are several surface points that are deeper than the measurement point 1624 associated with the measurement cursor 1634. As shown in FIGS. 24A and 24B, when the measurement cursor 1634 is moved toward the deeper points (shown in a first color 1662 (e.g., red) on the depth color gradient overlay 1660), the area of the depth color gradient overlay 1660 decreases indicating that the measurement cursor 1634 is getting closer to the deepest point. In particular, the depth color gradient overlay 1660 of FIGS. 24A and 24B shows that there are fewer surface points in the depth color gradient overlay 1660 indicating to the user that there are few surface points that are deeper than the measurement point 1624. Guided by the depth plane graphic overlay 1650 and the depth color gradient overlay 1660, in FIG. 25, the user has moved the measurement cursor 1634 to the deepest point of the pit or dent 1605 such that the measurement cursor 1634 (and associated measurement point 1624) is accurately placed at the deepest point of the pit or the dent 1605 as evidenced by the lack of any visible depth color gradient overlay 1660. The depth 1670 of the measurement point 1624 associated with the measurement cursor 1634 from the reference surface 1620 is shown in the point cloud view 1603 in FIG. 25.

Figure 26:
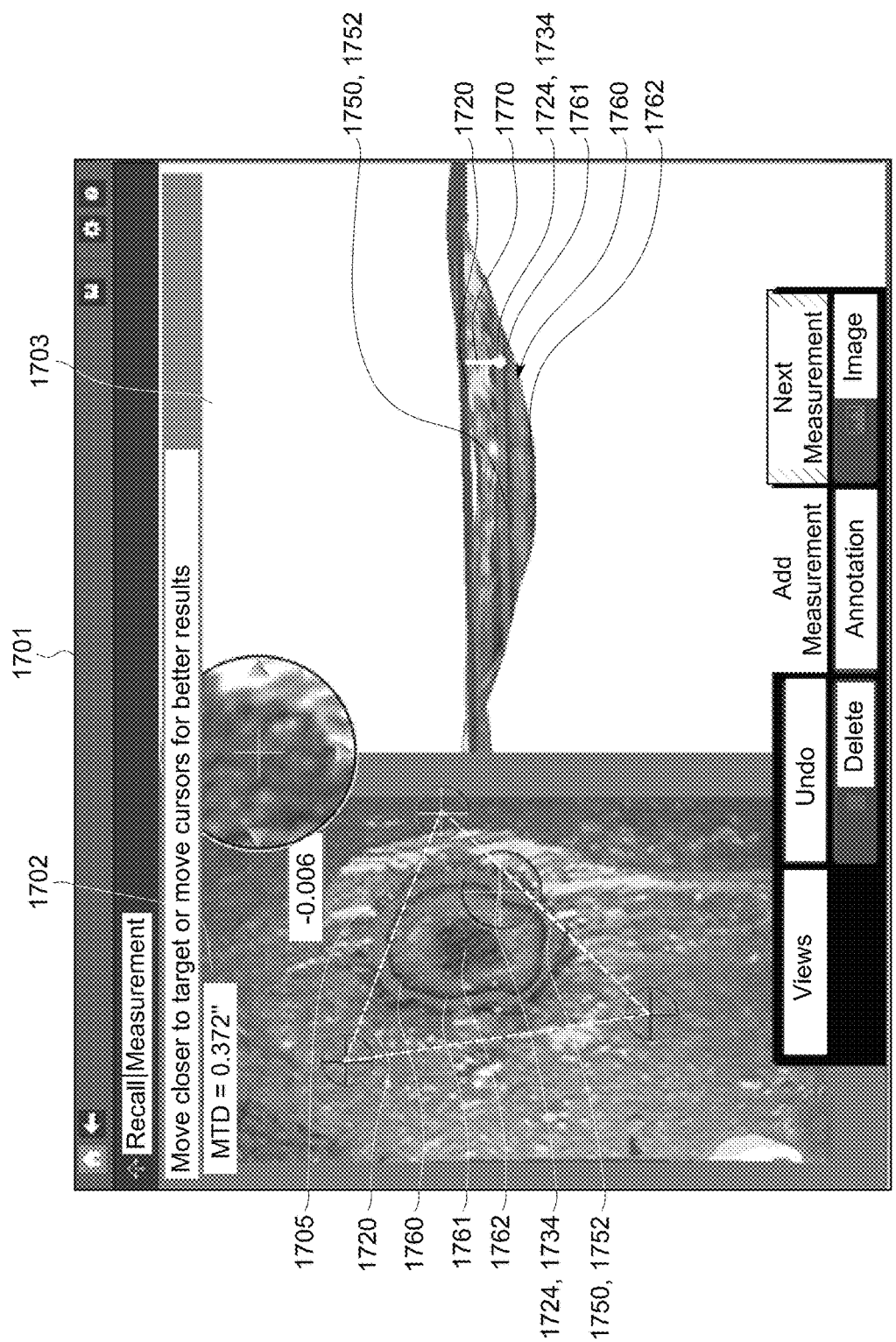
FIG. 26 is a side-by-side image displaying a two-dimensional image of the viewed object having a pit or dent and a three-dimensional point cloud view of the pit or dent illustrating a depth plane graphic overlay, where the measurement cursor is located far from the deepest point.
Figure 27:
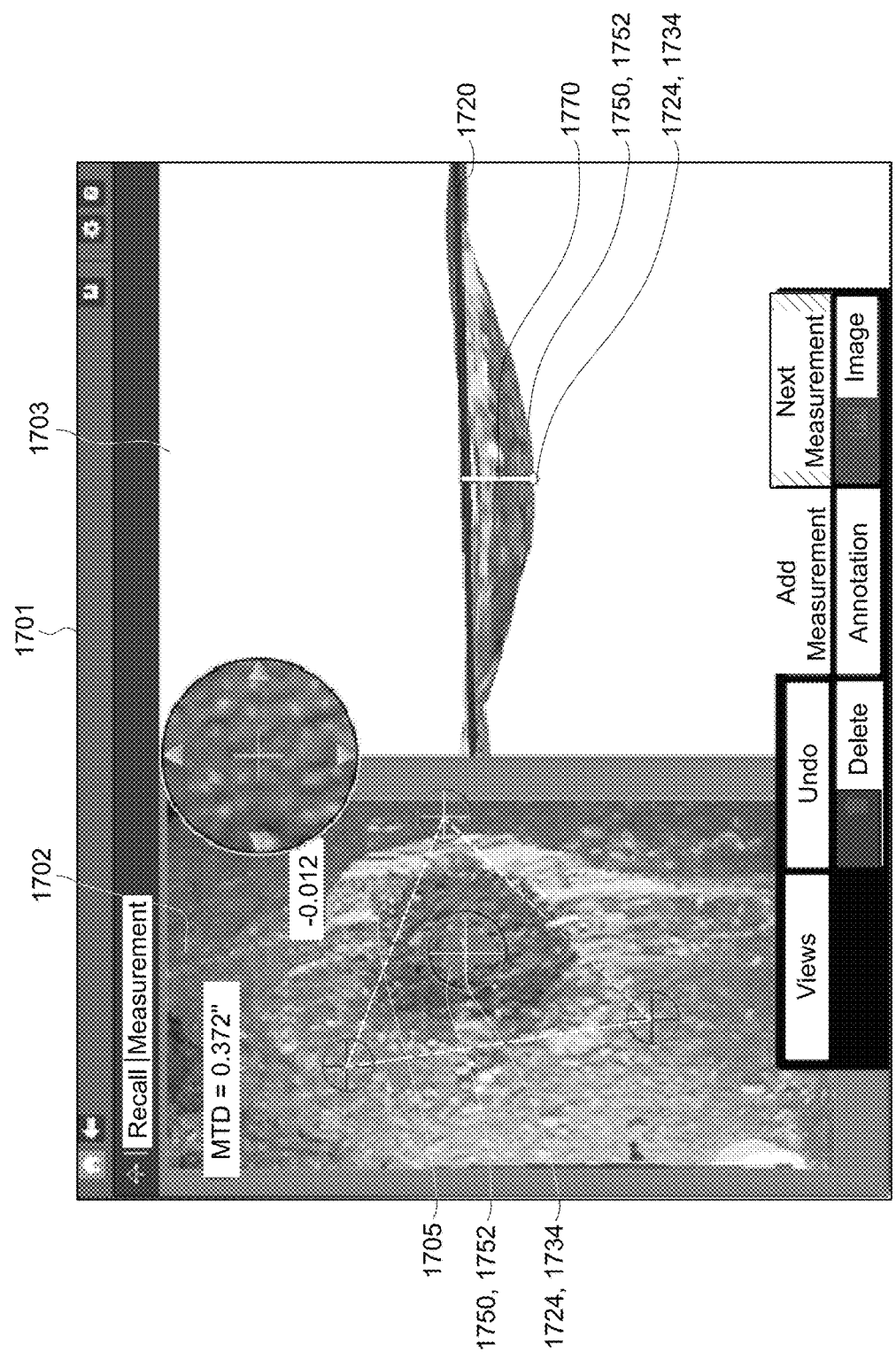
FIG. 27 is a side-by-side image displaying a two-dimensional image of the viewed object having a pit or dent and a three-dimensional point cloud view of the pit or dent illustrating a depth plane graphic overlay, where the measurement cursor is located at the deepest point.

FIGS. 26 and 27 provide another illustration of the use of a depth plane graphic overlay 1750 and depth color gradient overlay 1760 on two-dimensional 1702 and three-dimensional (point cloud) 1703 views used to measure the depth of a pit or dent 1705. As shown in FIG. 26, when the measurement cursor 1734 is located far from the deepest point of the pit or dent 1705, the depth plane graphic overlay 1750 and depth color gradient overlay 1760 (transitioning from shallow points 1761 to the deepest points 1762) show that there are several surface points that are deeper than the measurement point 1724, indicating that the measurement cursor 1734 should be moved toward the deepest points (e.g., shown in a first color 1762 (e.g., red) in the depth color gradient overlay 1760). This is also shown on the point cloud view 1703 of FIG. 26, where the depth 1770 of the measurement cursor 1734 and associated measurement point 1724 are located far from the deepest point 1762 of the pit or dent 1705.

The relatively large area of the depth color gradient overlay 1760 in FIG. 26 indicates that there are several surface points that are deeper than the measurement point 1724 associated with the measurement cursor 1734. Guided by the depth plane graphic overlay 1750 and the depth color gradient overlay 1760, in FIG. 27, the measurement cursor 1734 has been moved, for example, by a user, to the deepest point of the pit or dent 1705 such that the measurement cursor 1734 (and associated measurement point 1724) is accurately placed at the deepest point of the pit or the dent 1705 as evidenced by the lack of any visible depth color gradient overlay 1760. The depth 1770 of the measurement point 1724 associated with the measurement cursor 1734 from the reference surface 1720 is shown in the point cloud view 1703 in FIG. 27. As shown in FIGS. 26 and 27, the pit or dent 1705 being inspected has a relatively flat bottom leading to a depth plane graphic overlay 1750 at the deepest point that shows that there are several surface points at or near the maximum depth.

Figure 28:
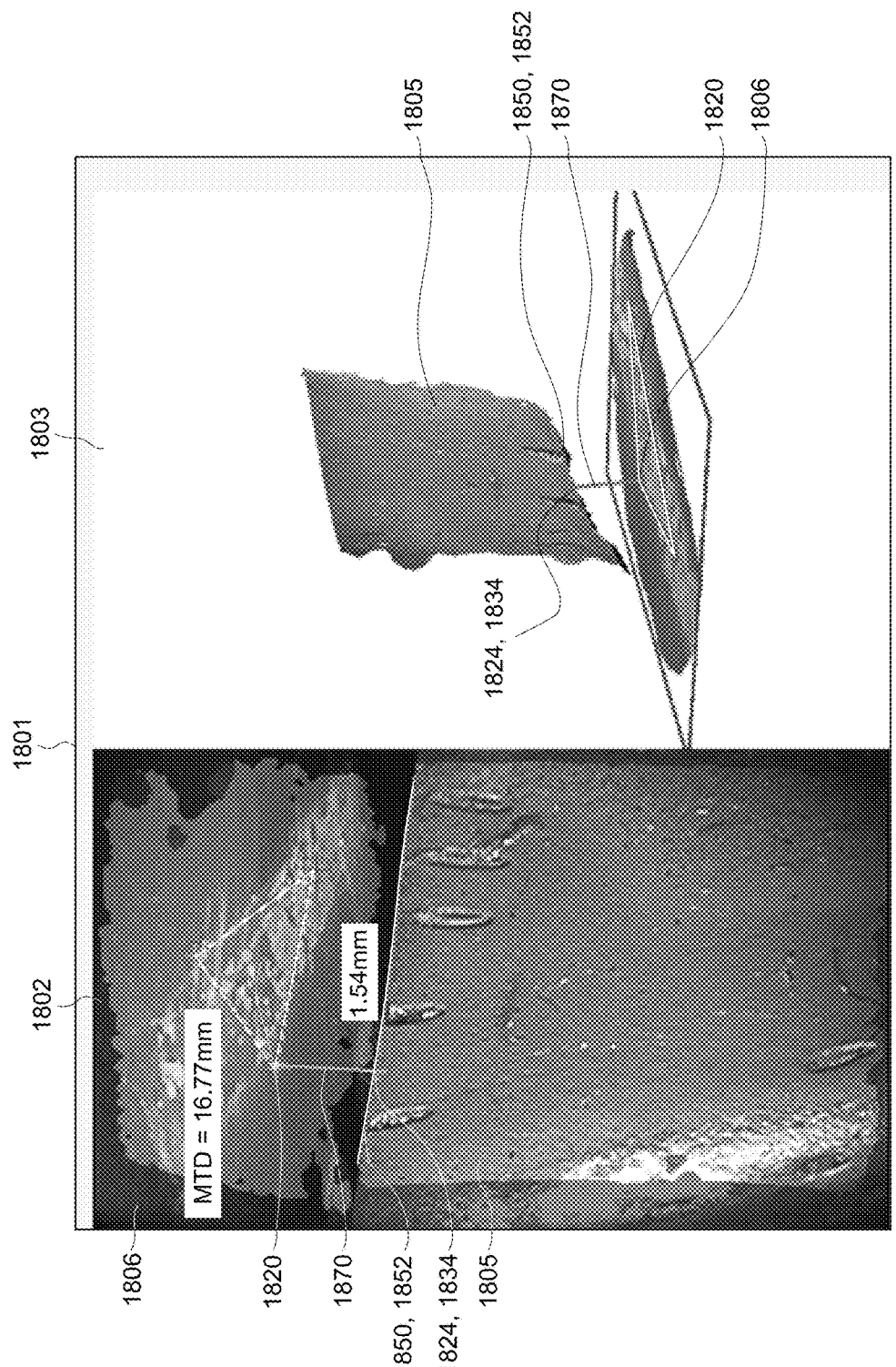
FIG. 28 is a side-by-side image displaying a two-dimensional image of the area between the tip of a turbine blade and the shroud and a three-dimensional point cloud view of the same illustrating a depth plane graphic overlay.

FIG. 28 is a side-by-side image 1801 displaying a two-dimensional image 1802 of the area between the tip of a turbine blade 1805 and the shroud 1806 and a three-dimensional point cloud view 1803 of the same illustrating a depth plane graphic overlay. This depth measurement (or height measurement) can provide the tip-to-shroud distance or clearance 1870 in a turbine inspection. As in the example of FIGS. 23A-25, a reference surface 1820 is determined based on the three reference surface cursors shown in FIG. 29. In the tip-to-shroud measurement illustrated in FIG. 29, the measurement cursor 1834 should be placed on the edge or tip of the turbine blade 1805 to accurately measure the depth (the tip-to-blade clearance 1870). In the example shown in FIG. 29, the measurement cursor 1834 is placed on the turbine blade 1805 and a depth plane graphic overlay 1850 (e.g., light blue), can be placed on pixels associated with surface points having three-dimensional surface coordinates less than a predetermined distance from a depth plane 1852 that is parallel to the reference surface (e.g., plane) 1820 and passes through the measurement point 1824 corresponding to the location of measurement cursor 1834 to help the user place the measurement cursor 1834 on the edge or tip of the turbine blade 1805. Since the depth plane graphic overlay 1850 in FIG. 29 appears to be aligned with the edge or tip of the turbine blade 1805, a user can be confident that the measurement cursor 1834 is located on a point that is representative of the tip clearance 1870 of the majority of the turbine blade 1805. In this embodiment, since the depth measurement (tip clearance 1870) is positive, there is no color gradient.

Figure 29A:
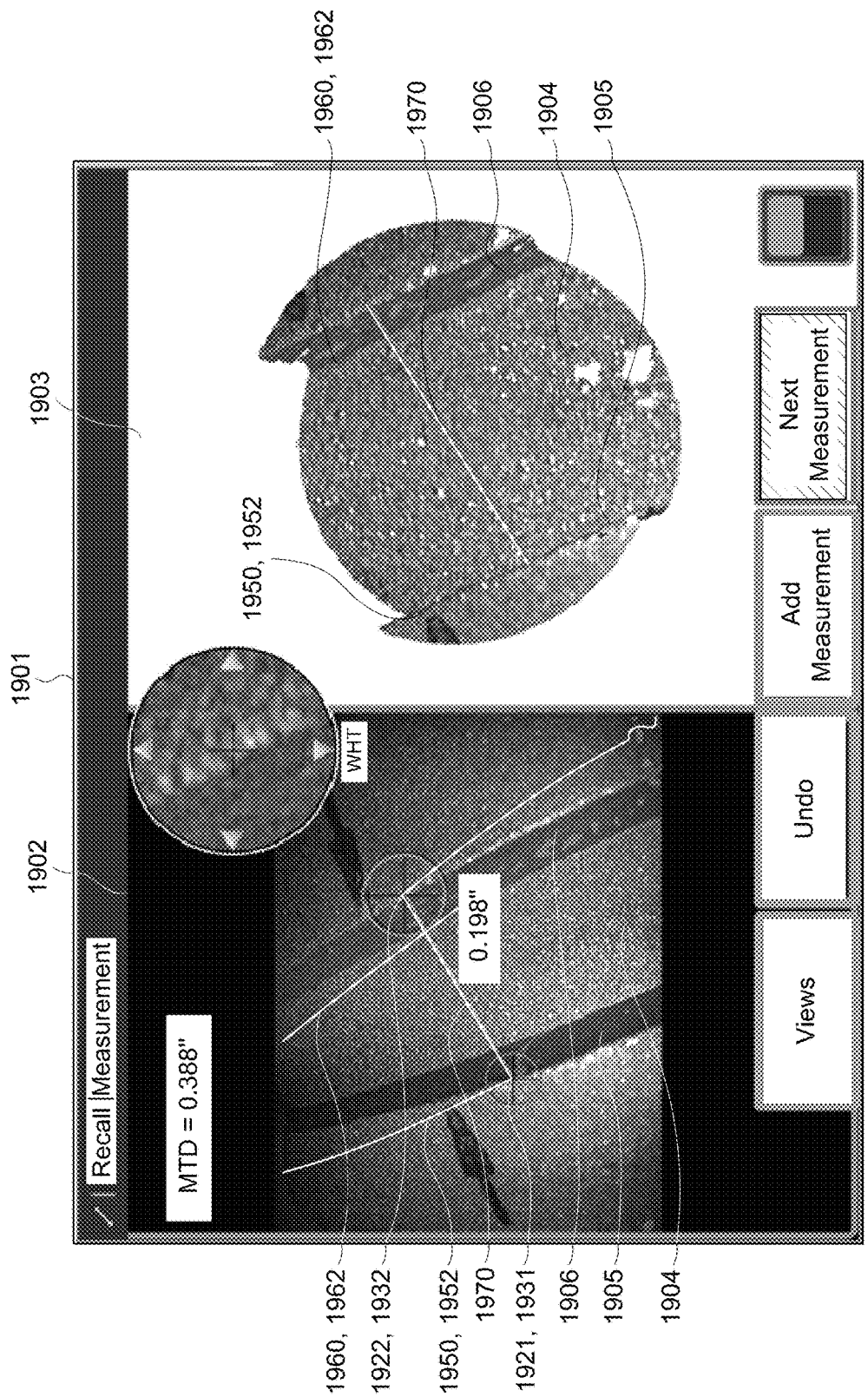
FIG. 29A is a side-by-side image displaying a two-dimensional image of a slot and a three-dimensional point cloud view of the slot illustrating edge plane graphic overlays where the measurement cursors are placed diagonally across from each other.
Figure 29B:
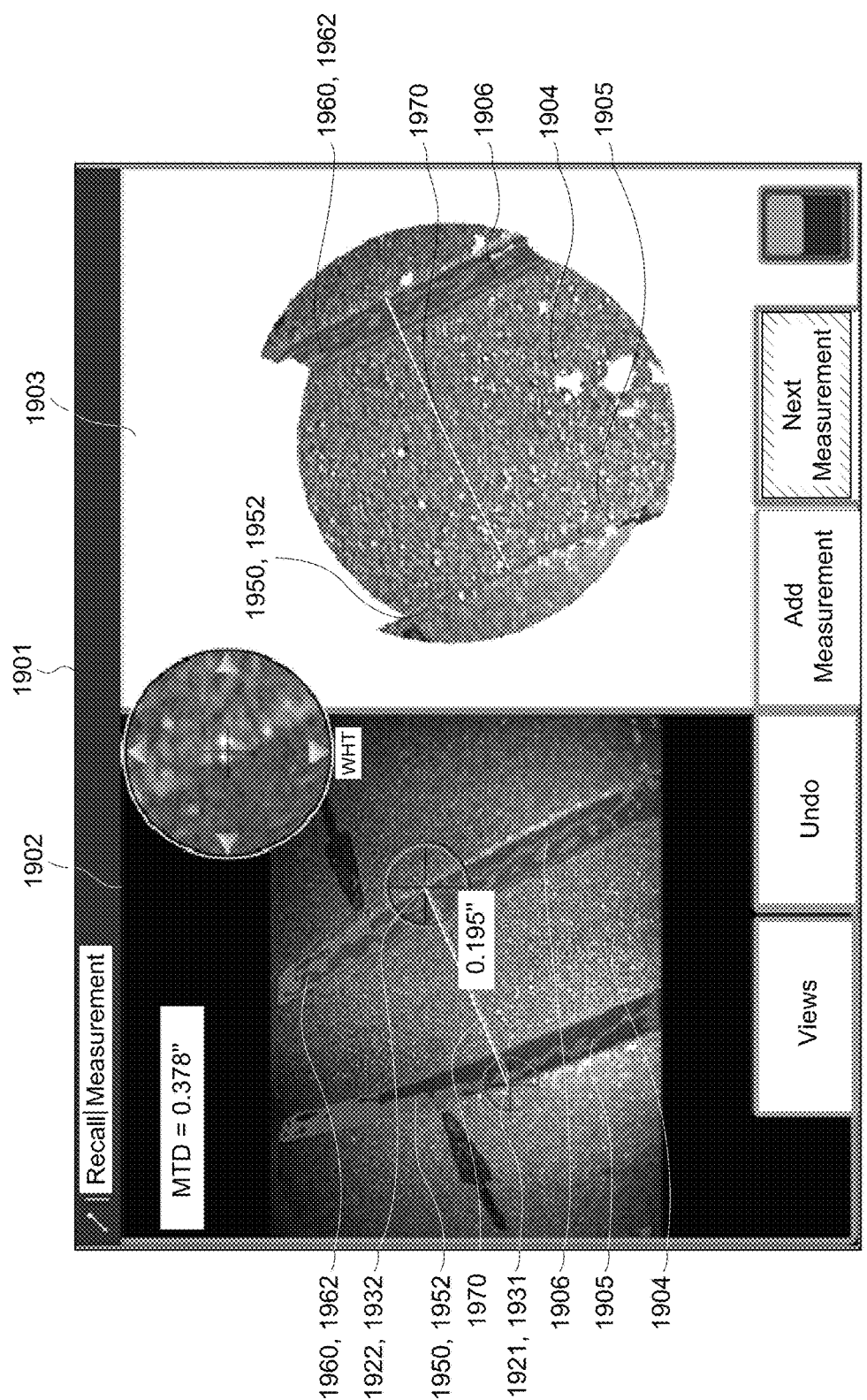
FIG. 29B is a side-by-side image displaying a two-dimensional image of a slot and a three-dimensional point cloud view of the slot illustrating edge plane graphic overlays where the measurement cursors are placed directly across from each other.

Video inspection devices can be used to perform various measurements to determine the length between surface points or surfaces, including measurement of the width of a weld or a slot. For example, FIGS. 29A-29B show various two-dimensional and three-dimensional (point cloud) views used to measure the width of a slot. In some instances, there may be a challenge in making a length measurement across a slot where it may be difficult to visually determine, and place cursors at, points on each side of the slot where the line formed between the points is normal (e.g., not diagonal) to each of the walls to provide an accurate width of the slot. As will be explained and as shown in FIGS. 29A-29B, visual indications, such as a first semi-transparent edge plane graphic overlay 1950 (e.g., light blue) and a second semi-transparent edge plane graphic overlay 1960, can be placed on pixels associated with surface points having three-dimensional surface coordinates less than a predetermined distance from a first edge plane 1952 and second edge plane 1962, respectively, that are perpendicular to the three-dimensional line 1970 between the the measurement points 1921, 1922 corresponding to the locations of measurement cursors 1931, 1932 to help the user or other placement means, place the measurement cursors 1931, 1932 on the walls 1905, 1906 of the slot 1904.

FIG. 29A is a side-by-side image 1901 displaying a two-dimensional image 1902 of a slot 1904 having a first wall 1905 and a second wall 1906 and a three-dimensional point cloud view 1903 of the slot 1904 illustrating a first semi-transparent edge plane graphic overlay 1950 (e.g., light blue) and a second semi-transparent edge plane graphic overlay 1960, where the measurement cursors 1931, 1932 are placed diagonally across from each other on the first wall 1905 and second wall 1906.

In one embodiment and as shown in FIG. 29A, a first measurement cursor 1931 is placed on the two-dimensional image 1902 or the point cloud view 1903 on a first measurement point 1921 on the first wall 1905 of the slot 1904. Similarly, a second measurement cursor 1932 is placed on the two-dimensional image 1902 or the point cloud view 1903 on a second measurement point 1922 on the second wall 1906 of the slot 1904. In the length measurement illustrated in FIG. 29A, the measurement cursors 1931, 1932 can be placed opposite of each other to accurately measure the width of the slot 1904. In some instances, the measurement cursors 1931 should be placed directly opposite of each other. In order to assist the user in accurately placing the measurement cursors 1931, 1932, the video inspection device 100 (e.g., the CPU 150) can determine a three-dimensional line 1970 between the measurement points 1921, 1922. The video inspection device 100 (e.g., the CPU 150) can then determine a first edge plane 1952 that is perpendicular (normal) to the three-dimensional line 1970 and passes through the first measurement point 1921 corresponding to the location of first measurement cursor 1931. The video inspection device 100 can then place a first semi-transparent edge plane graphic overlay 1950 (e.g., in a light blue color) on pixels in the two-dimensional image 1902 and the point cloud view 1903 associated with surface points having three-dimensional surface coordinates less than a predetermined distance from the first edge plane 1952 to help the user place the first measurement cursor 1931 on the first wall 1905 of the slot 1904. The video inspection device 100 (e.g., the CPU 150) can also determine a second edge plane 1962 that is perpendicular (normal) to the three-dimensional line 1970 (and/or parallel to the first edge plane 1952) and passes through the second measurement point 1922 corresponding to the location of second measurement cursor 1932. The video inspection device 100 can then place a second semi-transparent edge plane graphic overlay 1960 (e.g., in a light blue color) on pixels in the two-dimensional image 1902 and the point cloud view 1903 associated with surface points having three-dimensional surface coordinates less than a predetermined distance from the second edge plane 1962 to help the user place the second measurement cursor 1932 on the second wall 1906 of the slot 1904 and opposite, for example, directly opposite, the first measurement cursor 1931.

In order to determine whether to place an edge plane graphic overlay 1950, 1960 on a pixel in the two-dimensional image, the video inspection device 100 (e.g., CPU 150) can determine if that pixel is associated with a surface point having three-dimensional coordinates less than (or within) a predetermined distance from the edge planes 1952, 1962. In some embodiments, the distance between the surface point and the edge planes 1952, 1962 can be determined as a perpendicular distance, while in other embodiments, the distance can be a non-perpendicular distance. In one embodiment, the edge plane graphic overlays 1950, 1960 include any surface point having a perpendicular distance from the edge planes 1952, 1962 of less than 0.2% of the x-value of the measurement points 1921, 1922. In another embodiment, the edge plane graphic overlays 1950, 1960 include any surface points having a perpendicular distance from the edge planes 1952, 1962 of less than 1% of the measured length 1970.

In one example, the edge plane graphic overlays 1950, 1960 may be updated in real time as the measurement cursors 1931, 1932 are moved by the user. In other examples, the edge plane graphic overlays 1950, 1960 may be shown when the measurement cursors 1931, 1932 are active and can be turned off when the measurement result is active. In one embodiment, when the second measurement cursor 1932 is placed and the measurement result is displayed and becomes active, the edge plane graphic overlays 1950, 1960 are briefly displayed then hidden until a cursor is activated. The real time display of the edge plane graphic overlays 1950, 1960 during measurement can allow the user to more accurately place the measurement cursors 1931, 1932 on the desired surface points (e.g., points on each side of the slot 1904 where the three-dimensional line 1970 formed between the measurement points 1921, 1922 is normal (e.g., not diagonal) to each of the walls 1905, 1906 and can provide an accurate width of the slot 1904).

For example, as shown in FIG. 29A, when the three-dimensional line 1970 between the measurement cursors 1931, 1932 (and measurement points 1921, 1922) is not normal (e.g., it is diagonal) to the walls 1905, 1906 of the slot 1904), the edge plane graphic overlays 1950, 1960 and edge planes 1952, 1962 are not aligned with the walls 1905, 1906, indicating to the user that one or both of the measurement cursors 1931, 1932 may need to be relocated. Otherwise, the measured length of the three-dimensional line 1970, which is diagonal to the walls 1905, 1906 of the slot 1904, could provide an inaccurate measurement of the width of the slot 1904 (i.e., too wide).

As shown in FIG. 29B, when the second measurement cursor 1932 is moved such that the three-dimensional line 1970 between the cursors 1931, 1932 (and the measurement points 1921, 1922) is normal (e.g., not diagonal) to the walls 1905, 1906 of the slot 1904, the edge plane graphic overlays 1950, 1960 and edge planes 1952, 1962 are aligned with the walls 1905, 1906, indicating that the measured width of the slot 1904 is accurate.

Figure 30A:
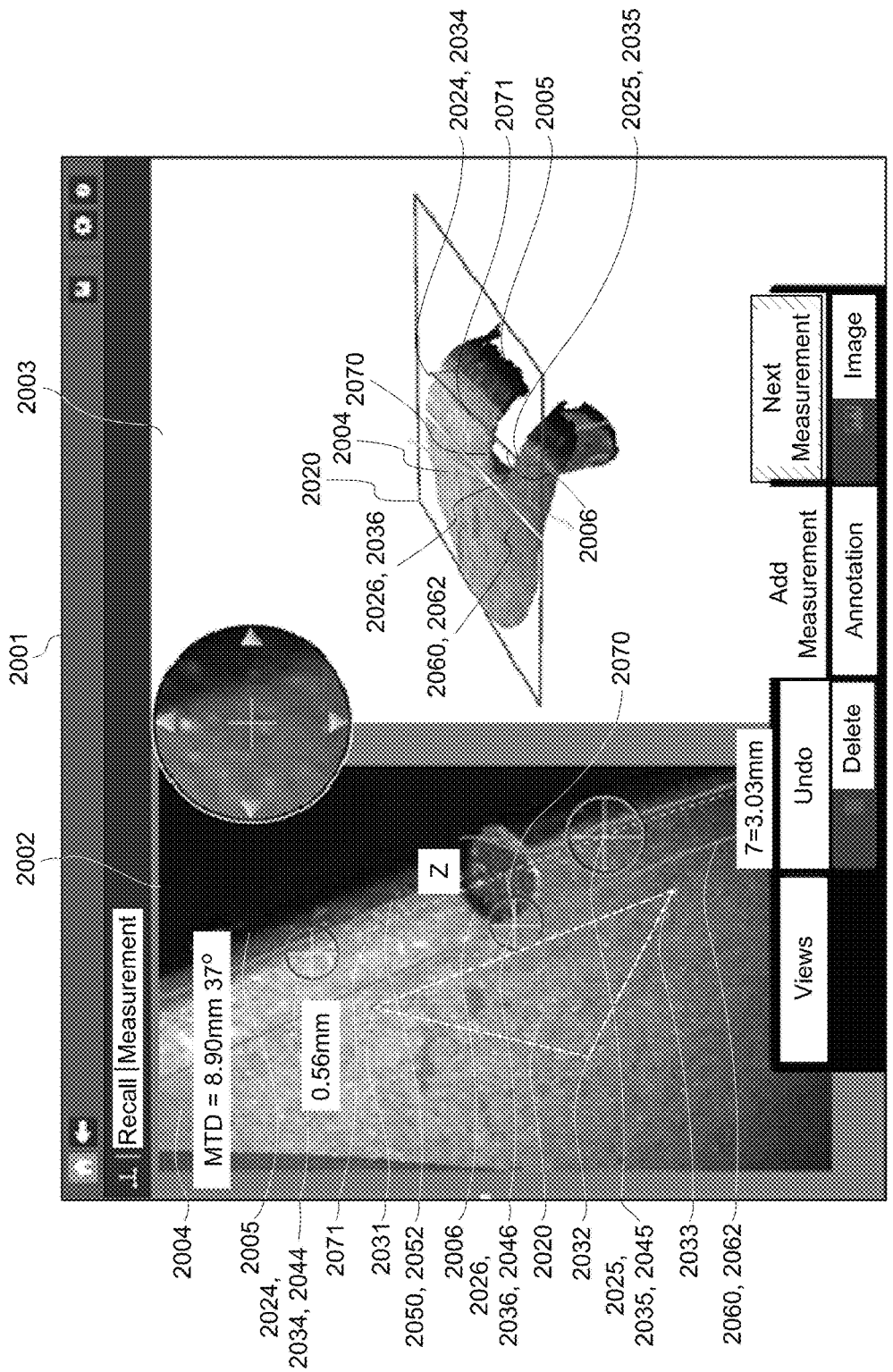
FIG. 30A is a side-by-side image displaying a two-dimensional image of an edge of a turbine blade and a three-dimensional point cloud view of the edge of the turbine blade illustrating edge plane graphic overlays where the measurement cursors are not located on the edge of the turbine blade.
Figure 30B:
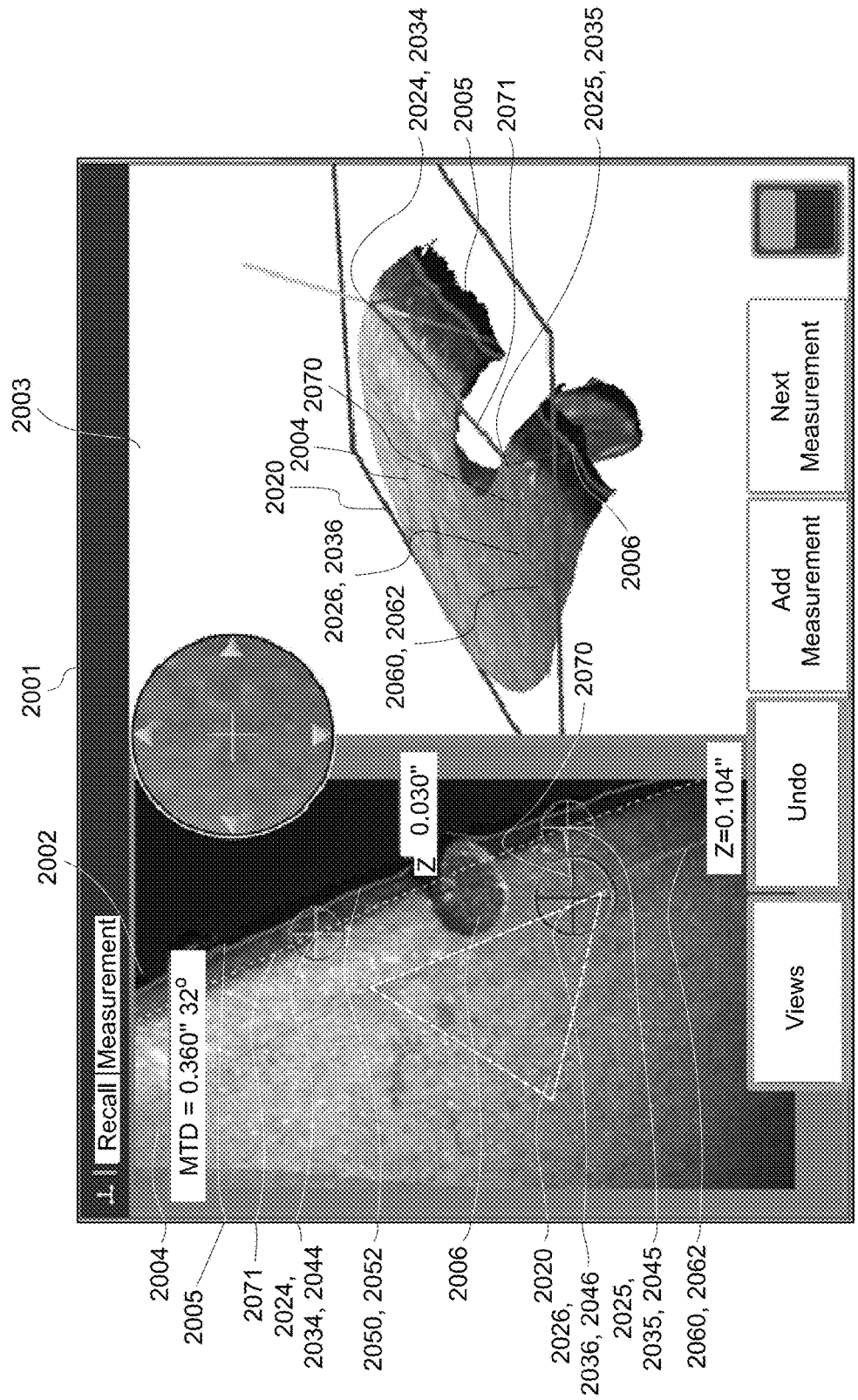

Video inspection devices can be used to perform various measurements to determine the distance from a point to a line, including measurements of turbine blade edge damage and measurements of the width/length of a gap, groove, or weld. For example, FIGS. 30A-30B show various two-dimensional and three-dimensional (point cloud) views used to measure damage to the edge of a turbine blade. In some instances, a challenge experienced in making a point to line measurement of the edge of the turbine blade is that it may be difficult to visually determine, and place cursors at, points on the actual edge of the turbine blade to provide an accurate measurement of the damaged portion. As will be explained and as shown in FIGS. 30A-30B, visual indications, such as a first semi-transparent edge plane graphic overlay 2050 (e.g., light blue) and a second semi-transparent edge plane graphic overlay 2060, can be placed on pixels associated with surface points having three-dimensional surface coordinates less than a predetermined distance from a first edge plane 2052 and second edge plane 2062, respectively. The edge planes 2052, 2062 can be perpendicular to the three-dimensional length line 2070 between the third measurement cursor 2036 and the three-dimensional reference line 2071 between the first measurement cursor 2034 and the second measurement cursor 2035 and pass through the projected reference surface points 2024, 2025, 2026 corresponding to the locations of measurement cursors 2034, 2035, 2036 to help the user place the measurement cursors 2034, 2035 on the edge 2005 of the turbine blade 2004 and on the edge of the missing portion 2006.

FIG. 30A is a side-by-side image 2001 displaying a two-dimensional image 2002 of an edge 2005 of a turbine blade 2004 having a missing portion 2006 and a three-dimensional point cloud view 2003 of the edge 2005 of the turbine blade 2004 illustrating edge plane graphic overlays 2050, 2060 where the measurement cursors 2034, 2035 are not located on the edge 2005 of the turbine blade 2004.

In one embodiment and as shown in FIG. 30A, the video inspection device 100 (e.g., the CPU 150) can determine a three-dimensional reference surface 2020 (e.g., measurement plane) formed by reference surface cursors 2031, 2032, 2033 as described above with respect to FIGS. 15A and 17. As shown in FIG. 30A, for example, a total of three measurement cursors 2034, 2035, 2036 can then positioned on measurement cursor pixels 2044, 2045, 2046 of the image 2001 to perform a point-to-line measurement. The three-dimensional trajectory associated with each two-dimensional measurement cursor pixels 2044, 2045, 2046 of the image 2001 is known and can be used to calculate where the trajectory line from each measurement cursor pixel 2044, 2045, 2046 of the image 2001 is positioned (e.g., which can be a fractional pixel position in which interpolation would be used) intersects with the reference surface 2020 in three-dimensional space to determine the projected reference surface points 2024, 2025, 2026 associated with those measurement cursor pixels 2044, 2045, 2046 on the reference surface 2020.

In order to conduct the point-to-line measurement, the video inspection device 100 (e.g., the CPU 150) can determine a reference line 2071 between the projected reference surface points 2024, 2025 corresponding to measurement cursors 2034, 2035. The video inspection device 100 (e.g., the CPU 150) can then determine a three-dimensional length line 2070 between the projected surface point 2026 corresponding to the third measurement cursor 2036 and the reference line 2071. The video inspection device 100 (e.g., the CPU 150) can determine a first edge plane 2052 that is perpendicular (normal) to the three-dimensional length line 2070 and passes through the first and second projected reference surface points 2024, 2025 corresponding to measurement cursors 2034, 2035. The video inspection device 100 can then place a first semi-transparent edge plane graphic overlay 2050 (e.g., in a light blue color) on pixels in the two-dimensional image 2002 and the point cloud view 2003 associated with surface points having three-dimensional surface coordinates less than a predetermined distance from the first edge plane 2052 to help the user place the measurement cursors 2034, 2035 such that the corresponding projected reference surface points 2024, 2025 correspond to the actual edge 2005 of the turbine blade 2004. The video inspection device 100 (e.g., the CPU 150) can also determine a second edge plane 2062 that is perpendicular (normal) to the three-dimensional length line 2070 (and/or parallel to the first edge plane 2052) and passes through the third projected reference surface point 2026 corresponding to the location of third measurement cursor 2036 to be placed at the edge of the missing portion 2006. The video inspection device 100 can then place a second semi-transparent edge plane graphic overlay 2060 (e.g., in a light blue color) on pixels in the two-dimensional image 2002 and the point cloud view 2003 associated with surface points having three-dimensional surface coordinates less than a predetermined distance from the second edge plane 2062.

In order to determine whether to place an edge plane graphic overlay 2050, 2060 on a pixel in the two-dimensional image, the video inspection device 100 (e.g., CPU 150) determines if that pixel is associated with a surface point having three-dimensional coordinates less than (or within) a predetermined distance from the edge planes 2052, 2062. In some embodiments, the distance between the surface point and the edge planes 2052, 2062 can be determined as a perpendicular distance, while in other embodiments, the distance can be a non-perpendicular distance. In one embodiment, the edge plane graphic overlays 2050, 2060 include any surface point having a perpendicular distance from the edge planes 2052, 2062 of less than 0.2% of the x-value of the surface points 2021, 2022. In another embodiment, the edge plane graphic overlays 2050, 2060 include any surface points having a perpendicular distance from the edge planes 2052, 2062 of less than of less than 1% of the three-dimensional length line 2070.

In one example, the edge plane graphic overlays 2050, 2060 may be updated in real time as the measurement cursors 2034, 2035, 2036 are moved, for example, by the user. In other examples, the edge plane graphic overlays 2050, 2060 may be shown when the measurement cursors 2034, 2035, 2036 are active and can be turned off when the measurement result is active. In one embodiment, when the third measurement cursor 2036 is placed and the measurement result is displayed and becomes active, the edge plane graphic overlays 2050, 2060 are briefly displayed then hidden until a cursor is activated. The real time display of the edge plane graphic overlays 2050, 2060 during measurement allows the user to more accurately place the measurement cursors 2034, 2035 on the actual edge 2005 of the turbine blade 2004 and on the edge of the missing portion 2006.

For example, as shown in FIG. 29A, when the measurement cursors 2034, 2035 are not placed on the actual edge 2005 of the turbine blade 2004, the first edge plane graphic overlays 2050 and first edge plane 2052 are not aligned with the edge 2005 of the turbine blade 2004, indicating that one or both of the measurement cursors 2034, 2035 should be relocated. Otherwise, the measured length of the three-dimensional length line 2070 would provide an inaccurate measurement of the length of the missing portion 2006.

As shown in FIG. 30B, when the measurement cursors 2034, 2035 are placed on the actual edge 2005 of the turbine blade 2004, the first edge plane graphic overlay 2050 and first edge plane 2052 is aligned with the actual edge 2005 of the turbine blade 2004, indicating to the user that the measured length of the missing portion 2006 is accurate.

Figure 31:
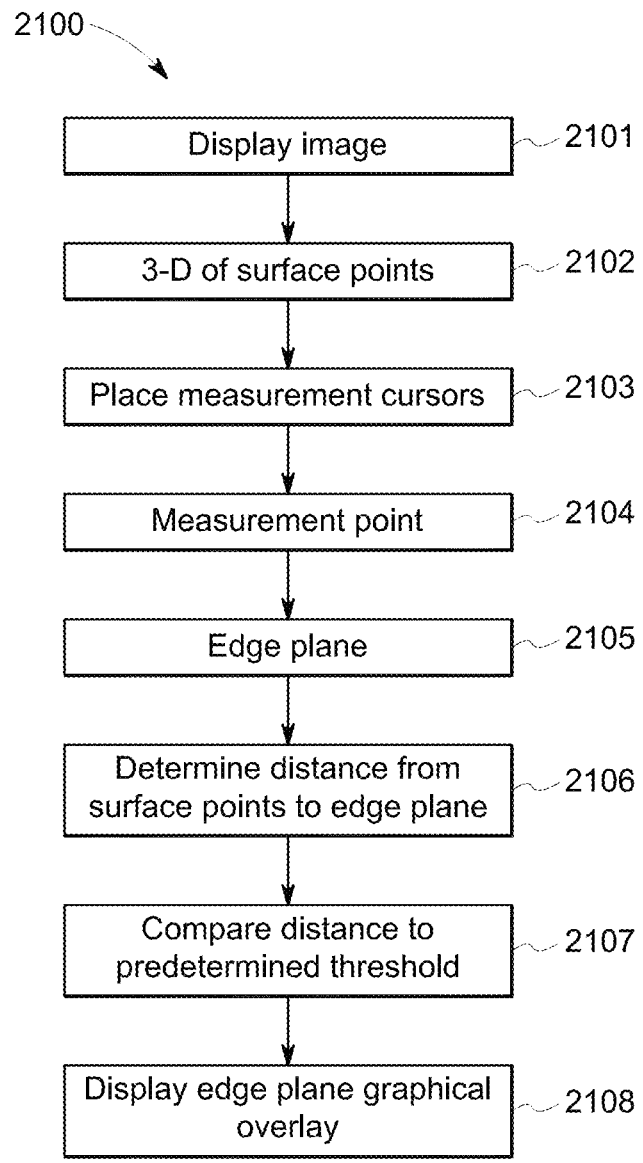
FIG. 31 illustrates an exemplary flowchart of a method for measuring a feature in an exemplary embodiment.

FIG. 31 illustrates an exemplary flowchart of a method 2100 for measuring a feature in an exemplary embodiment. At step 2101, an image of the viewed object can be displayed on a monitor. At step 2102, a central processor unit can determine three-dimensional coordinates of a plurality of points on a surface of the viewed object. At step 2103, one or measurement cursors can be placed on the image using a pointing device. At step 2104, the central processor can determine a measurement point corresponding to the location of at least one measurement cursor. At step 2105, the central processor unit can determine an edge plane, wherein the edge plane passes through the measurement point. At step 2106, the central processor unit can determine a distance between the plurality of points on a surface of the viewed object and the edge plane. At step 2107, the central processor unit can compare the distance between the plurality of points on a surface of the viewed object and the edge plane to a predetermined distance threshold. At step 2108, an edge plane graphical overlay is displayed on pixels in the image associated with the plurality of points on a surface of the viewed object having a distance to the edge plane that is below the predetermined distance threshold.

In view of the foregoing, embodiments of the invention allow for determining whether a measurement cursor is accurately located when conducting a measurement. A technical effect is to provide more accurate measurements of, e.g., an anomaly on the object. If, for example, the dimensions of the anomaly exceeds a tolerance specification or other threshold, an inspector can take preventative measures (i.e., take the machine or device out of service) until a repair is conducted.

As will be appreciated by one skilled in the art, aspects of the present invention may be embodied as a system, method, or computer program product. Accordingly, aspects of the present invention may take the form of an entirely hardware embodiment, an entirely software embodiment (including firmware, resident software, micro-code, etc.), or an embodiment combining software and hardware aspects that may all generally be referred to herein as a "service," "circuit," "circuitry," "module," and/or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

Program code and/or executable instructions embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer (device), partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described herein with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

To the extent that the claims recite the phrase "at least one of in reference to a plurality of elements, this is intended to mean at least one or more of the listed elements, and is not limited to at least one of each element. For example, "at least one of an element A, element B, and element C," is intended to indicate element A alone, or element B alone, or element C alone, or any combination thereof "At least one of element A, element B, and element C" is not intended to be limited to at least one of an element A, at least one of an element B, and at least one of an element C.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method for measuring a feature, the method comprising the steps of:
    displaying on a monitor an image of a viewed object;
    determining three-dimensional coordinates of a plurality of points on a surface of the viewed object using a central processor unit;
    placing one or more measurement cursors on the image using a pointing device;
    determining a measurement point corresponding to the location of at least one measurement cursor using the central processor unit;
    determining an edge plane using the central processor unit, wherein the edge plane passes through the measurement point;
    determining a distance between the plurality of points on a surface of the viewed object and the edge plane using a central processor unit;
    comparing the distance between the plurality of points on a surface of the viewed object and the edge plane to a predetermined distance threshold using the central processor unit; and
    displaying an edge plane graphical overlay on pixels in the image associated with the plurality of points on a surface of the viewed object having a distance to the edge plane that is below the predetermined distance threshold.

2. A method for measuring a feature, the method comprising the steps of:
    displaying on a monitor an image of a viewed object;
    determining three-dimensional coordinates of a plurality of points on a surface of the viewed object using a central processor unit;
    placing a first measurement cursor and a second measurement cursor on the image using a pointing device;
    determining a first measurement point corresponding to the location of the first measurement cursor using the central processor unit;
    determining a second measurement point corresponding to the location of the second measurement cursor using the central processor unit;
    determining a three-dimensional line between the first measurement point and the second measurement point using the central processor unit;
    determining a first edge plane using the central processor unit, wherein the first edge plane is normal to the three-dimensional line and passes through the first measurement point;
    determining a distance between the plurality of points on a surface of the viewed object and the first edge plane using a central processor unit;
    comparing the distance between the plurality of points on a surface of the viewed object and the first edge plane to a predetermined distance threshold using the central processor unit; and
    displaying a first edge plane graphical overlay on pixels in the image associated with the plurality of points on a surface of the viewed object having a distance to the first edge plane that is below the predetermined distance threshold.

3. The method of claim 2, further comprising the steps of:
    determining a second edge plane using the central processor unit, wherein the second edge plane is normal to the three-dimensional line and passes through the second measurement point;
    determining a distance between the plurality of points on a surface of the viewed object and the second edge plane using a central processor unit;
    comparing the distance between the plurality of points on a surface of the viewed object and the second edge plane to a predetermined distance threshold using the central processor unit; and
    displaying a second edge plane graphical overlay on pixels in the image associated with the plurality of points on a surface of the viewed object having a distance to the second edge plane that is below the predetermined distance threshold.

4. The method of claim 2, wherein the image of the viewed object is a two-dimensional image.

5. The method of claim 2, wherein the image of the viewed object is a three-dimensional view of the plurality of points on the surface of the viewed object.

6. The method of claim 2, wherein the first measurement point is a point on the surface of the viewed object corresponding to the location of the first measurement cursor.

7. The method of claim 2, wherein the distance between the plurality of points on a surface of the viewed object and the first edge plane is a perpendicular distance.

8. A method for measuring a feature, the method comprising the steps of:
    displaying on a monitor an image of a viewed object;
    determining three-dimensional coordinates of a plurality of points on a surface of the viewed object using a central processor unit;

placing a first measurement cursor, a second measurement cursor, and a third measurement cursor on the image using a pointing device;

determining a first measurement point corresponding to the location of the first measurement cursor using the central processor unit;

determining a second measurement point corresponding to the location of the second measurement cursor using the central processor unit;

determining a third measurement point corresponding to the location of the third measurement cursor using the central processor unit;

determining a three-dimensional reference line between the first measurement point and the second measurement point using the central processor unit;

determining a three-dimensional length line between the third measurement point and the three-dimensional reference line using the central processor unit;

determining a first edge plane using the central processor unit, wherein the first edge plane is normal to the three-dimensional length line and passes through the first measurement point and the second measurement point;

determining a distance between the plurality of points on a surface of the viewed object and the first edge plane using a central processor unit;

comparing the distance between the plurality of points on a surface of the viewed object and the first edge plane to a predetermined distance threshold using the central processor unit; and displaying a first edge plane graphical overlay on pixels in the image associated with the plurality of points on a surface of the viewed object having a distance to the first edge plane that is below the predetermined distance threshold.

9. The method of claim 8, further comprising the steps of:

determining a second edge plane using the central processor unit, wherein the second edge plane is normal to the three-dimensional length line and passes through the third measurement point;

determining a distance between the plurality of points on a surface of the viewed object and the second edge plane using a central processor unit;

comparing the distance between the plurality of points on a surface of the viewed object and the second edge plane to a predetermined distance threshold using the central processor unit; and displaying a second edge plane graphical overlay on pixels in the image associated with the plurality of points on a surface of the viewed object having a distance to the second edge plane that is below the predetermined distance threshold.

10. The method of claim 8, wherein the image of the viewed object is a two-dimensional image.

11. The method of claim 8, wherein the image of the viewed object is a three-dimensional view of the plurality of points on the surface of the viewed object.

12. The method of claim 8, further comprising the steps of:

selecting one or more reference surface points from the plurality of points on the surface of the viewed object using a pointing device; and determining a reference surface using the central processor unit, wherein the reference surface is determined based on the one or more of the reference surface points;

wherein the first measurement point is a point on the reference surface corresponding to the location of the first measurement cursor.

13. The method of claim 8, wherein the distance between the plurality of points on a surface of the viewed object and the first edge plane is a perpendicular distance.

14. A method for measuring a feature, the method comprising the steps of:

displaying on a monitor an image of a viewed object;

determining three-dimensional coordinates of a plurality of points on a surface of the viewed object using a central processor unit;

selecting one or more reference surface points from the plurality of points on the surface of the viewed object using a pointing device;

determining a reference surface using the central processor unit, wherein the reference surface is determined based on the one or more of the reference surface points;

placing a measurement cursor on the image using the pointing device;

determining a measurement point corresponding to the location of the measurement cursor using the central processor unit;

determining a depth plane using the central processor unit, wherein the depth plane is parallel to the reference surface and passes through the measurement point;

determining a distance between the plurality of points on a surface of the viewed object and the depth plane using the central processor unit;

comparing the distance between the plurality of points on a surface of the viewed object and the depth plane to a predetermined distance threshold using the central processor unit; and displaying a depth plane graphical overlay on pixels in the image associated with the plurality of points on a surface of the viewed object having a distance to the depth plane that is below the predetermined distance threshold.

15. The method of claim 14, further comprising the step of displaying a depth color gradient overlay on pixels in the image associated with the plurality of points on a surface of the viewed object that are deeper than the depth plane, wherein a color of the pixel for a point on the surface is based on the distance between the point on the surface of the viewed object and the depth plane.

16. The method of claim 14, further comprising the steps of:

determining a distance between the plurality of points on a surface of the viewed object and the reference surface using a central processor unit;

comparing the distance between the plurality of points on a surface of the viewed object and the reference surface to a predetermined reference surface distance threshold using the central processor unit; and displaying a reference surface graphical overlay on pixels in the image associated with the plurality of points on a surface of the viewed object having a distance to the reference surface that is below the predetermined reference surface distance threshold.

17. The method of claim 14, wherein the image of the viewed object is a two-dimensional image.

18. The method of claim 14, wherein the image of the viewed object is a three-dimensional view of the plurality of points on the surface of the viewed object.

19. The method of claim 14, wherein the measurement point is a point on the surface of the viewed object corresponding to the location of the measurement cursor.

20. The method of claim 14, wherein the distance between the plurality of points on a surface of the viewed object and the depth plane is a perpendicular distance.

* * * * *